United States Patent
Bok et al.

(10) Patent No.: US 10,000,556 B2
(45) Date of Patent: Jun. 19, 2018

(54) SINGLE-DOMAIN V$_H$H ANTIBODIES DIRECTED TO NOROVIRUS GI.1 AND GII.4 AND THEIR USE

(71) Applicants: THE UNITED STATES OF AMERICA, AS REPRESENTED BY THE SECRETARY, DEPART OF HEALTH AND HUMAN SERVICES, Bethesda, MD (US); INSTITUTO NACIONAL DE TECNOLOGIA AGROPECUARIA, Ciudad Autonoma de Buenos Aires (AR)

(72) Inventors: Karin Bok, Bethesda, MD (US); Lorena Laura Garaicoechea, Buenos Aires (AR); Viviana Parreno, Buenos Aires (AR); Andrea Pamela Aguilar, Buenos Aires (AR); Marina Bok, Buenos Aires (AR); Lisbeth Kim Green, Olney, MD (US); Stanislav Vladimirovich Sosnovtsev, North Potomac, MD (US)

(73) Assignees: THE UNITED STATES OF AMERICA, as represented by the Secretary, Dept. of Health and Human Services, Washington, DC (US); INSTITUTO NACIONAL DE TECHNOLOGIA AGROPECUARIA, Buenos Aires (AR)

( * ) Notice: Subject to any disclaimer, the term of this patent is extended or adjusted under 35 U.S.C. 154(b) by 26 days.

(21) Appl. No.: 14/889,774

(22) PCT Filed: May 9, 2014

(86) PCT No.: PCT/US2014/037520
§ 371 (c)(1),
(2) Date: Nov. 6, 2015

(87) PCT Pub. No.: WO2014/183052
PCT Pub. Date: Nov. 13, 2014

(65) Prior Publication Data
US 2016/0102136 A1    Apr. 14, 2016

Related U.S. Application Data

(60) Provisional application No. 61/821,354, filed on May 9, 2013.

(51) Int. Cl.
*C07K 16/10*    (2006.01)
*G01N 33/569*   (2006.01)
*A61K 39/00*    (2006.01)

(52) U.S. Cl.
CPC ....... *C07K 16/10* (2013.01); *G01N 33/56983* (2013.01); *A61K 2039/505* (2013.01); *C07K 2317/22* (2013.01); *C07K 2317/24* (2013.01); *C07K 2317/33* (2013.01); *C07K 2317/34* (2013.01); *C07K 2317/565* (2013.01); *C07K 2317/569* (2013.01); *C07K 2317/76* (2013.01); *C07K 2317/92* (2013.01); *C12N 2770/16011* (2013.01); *C12N 2770/16034* (2013.01); *G01N 2333/08* (2013.01)

(58) Field of Classification Search
CPC .......... A61K 39/395; G01N 33/56983; G01N 2333/08
See application file for complete search history.

(56) References Cited

FOREIGN PATENT DOCUMENTS

| | | |
|---|---|---|
| EP | 2 757 111 A1 | 7/2014 |
| WO | WO 2006/056306 A2 | 6/2006 |
| WO | WO 2008/005880 A2 | 1/2008 |

OTHER PUBLICATIONS

Rudikoff et al. Proc Natl Acad. Sci. USA 1982 vol. 79 p. 1979-83.*
Garaicoechea et al., "Llama nanoantibodies with therapeutic potential against human norovirus diarrhea," *PLoS One* 10(8):e0133665, 33 pages. (Aug. 12, 2015).
Dai et al., "Evaluation of anti-norovirus IgY from egg yolk of chickens immunized with norovirus P particles," *Journal of Virological Methods* 186(1-2):126-131 (Dec. 1, 2012).
Florescu et al., "Is there a role for oral human immunoglobulin in the treatment for norovirus enteritis in immunocompromised patients?," *Pediatric Transplantation* 15(7):718-21 (Nov. 23, 2011).
Harmsen et al., "Selection and optimization of proteolytically stable llama single-domain antibody fragments for oral immunotherapy," *Appl. Microbiol. Biotechnol.* 72(3):544-551 (Feb. 1, 2006).
Hussack et al., "Neutralization of Clostridium difficile toxin A with single-domain antibodies targeting the cell receptor binding domain," *Journal of Biological Chemistry* 286(11):8961-8976 (Mar. 18, 2011).
International Search Report from parent PCT Application No. PCT/US2014/037520, 6 pages (dated Aug. 14, 2014).
Written Opinion from parent PCT Application No. PCT/US2014/037520, 6 pages (dated Aug. 14, 2014).
Garaicoechea et al., "Development of VHH nanobody libraries against norovirus G1.I and GII.4," *Congreso: 31 American Society for Virology Annual Meeting*, Abstract (meeting dates Jul. 21-25, 2012, catalog date Mar. 19, 2015).

* cited by examiner

*Primary Examiner* — Bao Li
(74) *Attorney, Agent, or Firm* — Klarquist Sparkman, LLP

(57) ABSTRACT

Isolated V$_H$H monoclonal antibodies are disclosed that specifically bind to a Norovirus polypeptide. In some embodiments, the Norovirus is a Genogroup I Norovirus or a Genogroup II Norovirus. In other embodiments, the Norovirus is Norwalk or MD2004 virus. In some embodiments, the monoclonal antibodies specifically bind VP1. Also disclosed are compositions including the disclosed antibodies, nucleic acids encoding these antibodies, expression vectors including the nucleic acids, and isolated host cells that express the nucleic acids. The antibodies and compositions disclosed herein can be used for detecting the presence of a Norovirus in a biological sample, or detecting a Norovirus infection. Also disclosed are methods of treating and/or preventing a NoV infection.

32 Claims, 9 Drawing Sheets a - GI specific VHHs a - GII specific VHHs

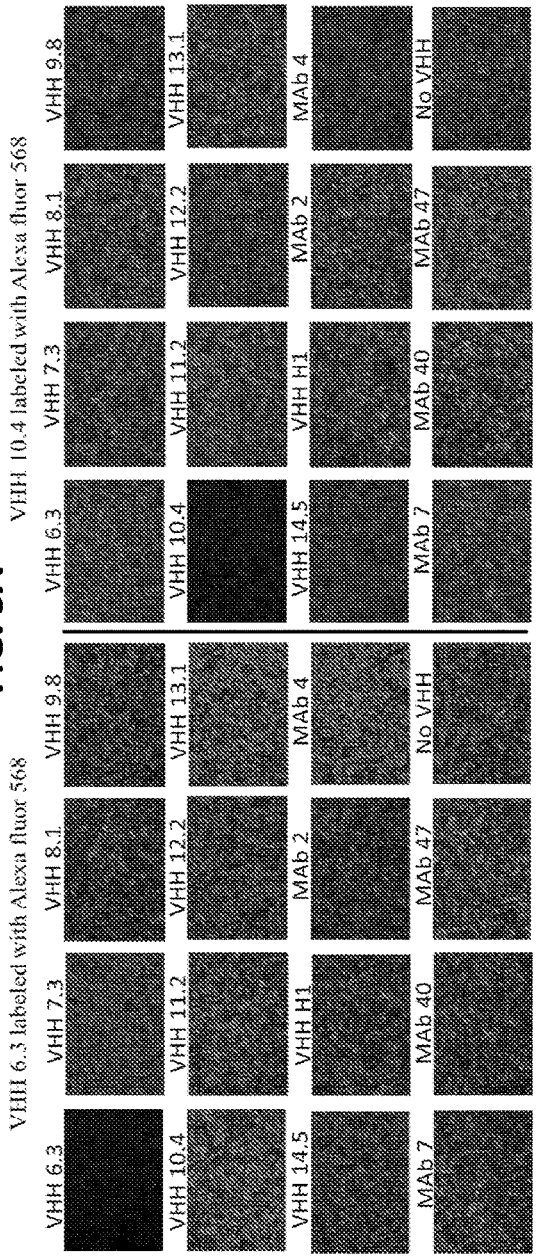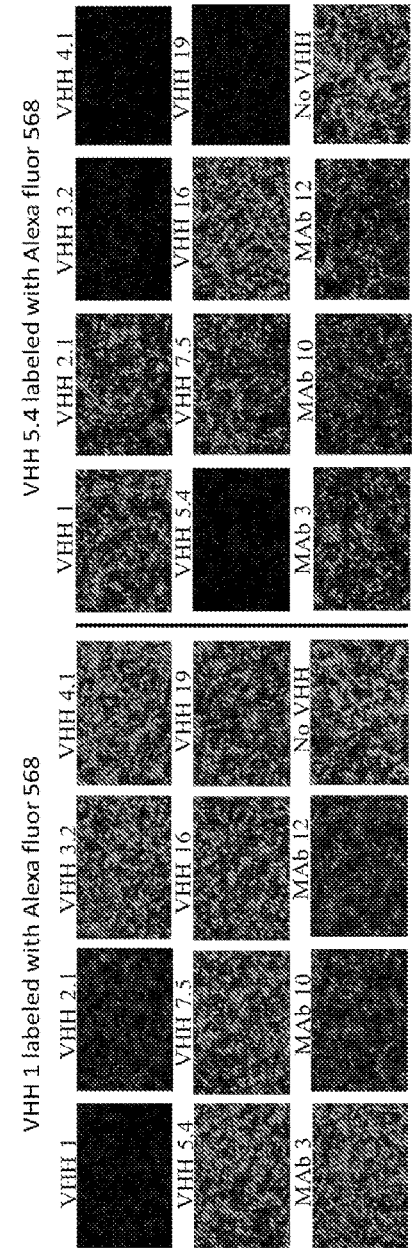
FIG. 5A
FIG. 5B

VP1 dimer of GII.4 NoV

FIG. 7A

MD2004 VP1 mutant

G340A    E376Q    N368 T    V389I    V340/E376

TV20

VHH 16

TV20                          VHH 16

No transfection   MD2004   WT      No transfection   MD2004   WT

FIG. 7B carbohydrates
aa 376
aa 340

VP1 dimer of GII.4 NoV

FIG. 8

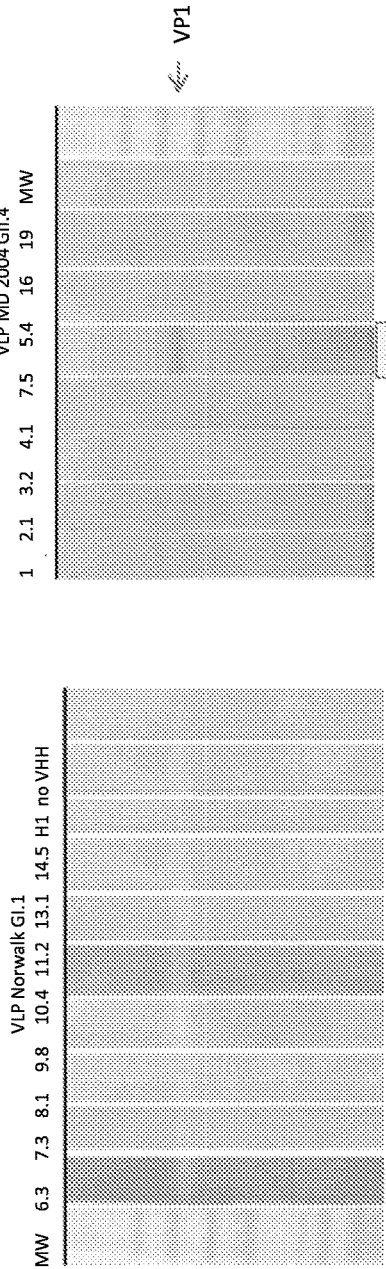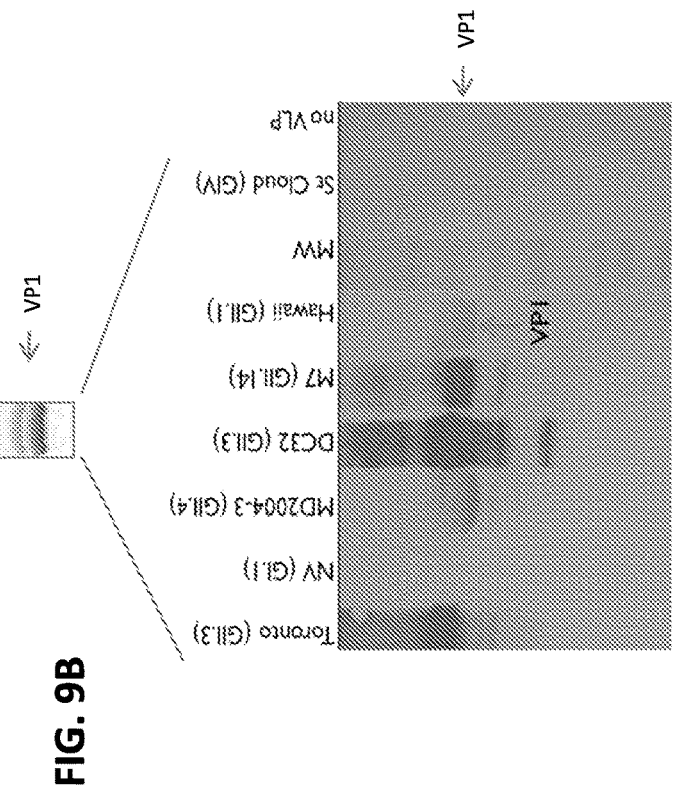
FIG. 9A
FIG. 9B

SINGLE-DOMAIN V$_H$H ANTIBODIES DIRECTED TO NOROVIRUS GI.1 AND GII.4 AND THEIR USE

CROSS REFERENCE TO RELATED APPLICATION

This is the U.S. National Stage of International Application No. PCT/US2014/037520, filed May 9, 2014, which was published in English under PCT Article 21(2), which claims the benefit of U.S. Provisional Application No. 61/821,354, filed May 9, 2013, which is incorporated by reference herein in its entirety.

FIELD OF THE DISCLOSURE

This relates to the field of antibodies, specifically to single-domain antibodies that specifically bind a Norovirus polypeptide, such as a Norwalk or MD2004 virus polypeptide, and their use.

BACKGROUND

Norovirus (NoV) is a non-enveloped virus that belongs to the family Caliciviridae. It constitutes the mayor cause of epidemic gastroenteritis in close settings (Green, Caliciviridae: The Noroviruses. Fields Virology, 6$^{th}$ edition. H. P. Knipe, et al. (eds), published by Philadelphia: Lippincott Williams & Wilkins: 582-608, (ISBN-13: 978-1451105636), 2013) and since the introduction of rotavirus vaccines, norovirus has become the leading cause of medically attended acute gastroenteritis in U.S. children, associated with nearly 1 million health care visits annually (Payne, et al., N Engl J Med 368(12): 1121-30, 2013). A gastroenteritis episode due to NoV is incapacitating during the acute phase that usually lasts from 1 to 3 days and includes explosive vomiting, stomach cramps and diarrhea Immunocompetent patients usually recover completely from the illness but the gastroenteritis may be severe in young children, the elderly and immunocompromised, increasing the risk for morbidity and mortality (Kaufman et al., Antiviral Res 105C: 80-91, 2014). It was estimated that around 200,000 children die annually because of NoV gastroenteritis, especially in developing countries (Patel et al., Emerg Infect Dis 14(8): 1224-3, 2008; Patel et al., J Clin Virol 44(1):1-8, 2009). In immunocompromised patients, NoV is recognized as an important cause of chronic gastroenteritis, with long-term virus shedding and increased morbidity in this population (Ludwig, et al., J Med Virol 80(8): 1461-7, 2008; Henke-Gendo et al., J Clin Microbiol 47(9): 2855-62, 2009; Florescu et al., Pediatr Transplant 15(7): 718-21, 2011). In immunocompetent patients the virus shedding after infection lasts for approximately 30 days, while in immunocompromised patients virus shedding has been detected for up to 3 years (Bok and Green, N Engl J Med 367(22): 2126-32, 2012; Payne et al., N Engl J Med 368(12): 1121-30, 2013; Kirby et al., J Med Virol, PubMed PMID: 24531909, 2014). It has been proposed that long term virus shedding may contribute to the spread of the virus (Debbink et al., PLoS Pathog 8(10): e1002921, 2014; Debbink et al., J Virol., Mar. 19, 2014).

The NoV genome is composed of a single-stranded positive-sense RNA molecule that contains three open reading frames. The genome is surrounded by a non-enveloped capsid composed of the major capsid protein, VP1, encoded by ORF2, and a minor structural protein, VP2, encoded by ORFS (Green, Caliciviridae: The Noroviruses, Fields Virology, 6th edition Knipe et al. (eds), published by Philadelphia: Lippincott Williams & Wilkins: 582-608, (ISBN-13: 978-1451105636), 2013). Crystallographic analysis showed that the NoV capsid is formed by 180 molecules of VP1, organized into 90 dimers. Each VP1 monomer is divided into two domains designated shell (S) and protruding (P), linked by a flexible hinge. The P domain is further divided into P1 and P2 subdomains, with P2 as the outermost domain exposed on the surface (Prasad et al., Science 286(5438): 287-90, 1999).

Noroviruses are divided into six major genogroups designated Genogroup (G)I through GVI. GI and GII contain the majority of NoV strains associated with human disease and are further divided into 9 and 21 genotypes, respectively (Kroneman et al., Arch Virol 158(10): 2059-68, 2013). The NoV GI.1 was the first genotype described, the GII.4 genotype has been associated with the majority of global outbreaks since the mid-1990s, when active surveillance with molecular diagnostic techniques was initiated (Zakikhany et al., PLoS One 7(7): e41625, 2012; Zheng et al., Virology 346(2): 312-23, 2006; Allen et al., Virol J 6: 150, 2009; Bok et al., J Virol 83(22): 11890-901, 2009; Patel et al., J Clin Virol 44(1): 1-8, 2009; Lindesmith et al., J Virol 85(1): 231-42, 2011; Lindesmith et al., J Virol 87(5): 2803-13, 2013). A need remains for reagents that can be used to detect and treat NoV infections.

SUMMARY OF THE DISCLOSURE

Isolated monoclonal antibodies, such as V$_H$H monoclonal antibodies, are disclosed that specifically bind to a NoV polypeptide. NoVs include Genogroup I and Genogroup II NoVs. NoVs include, for example, Norwalk virus (NV) and MD2004 virus. The monoclonal antibodies can specifically bind Genogroup I or a Genogroup II NoV polypeptide. In specific non-limiting examples, the monoclonal antibodies specifically bind VP1. The monoclonal antibodies can be neutralizing.

In some embodiments, the V$_H$H monoclonal antibody is a llama monoclonal antibody. In some embodiments, the monoclonal antibody is humanized. In some embodiments, the monoclonal antibody is chimeric.

In additional embodiments, disclosed are an isolated monoclonal antibody comprising a heavy chain domain, wherein the heavy chain variable domain comprises a heavy chain complementarity determining region (HCDR)1, an HCDR2 and an HCDR3, wherein the CDR3 comprises the amino acid sequence set forth as one of: a) amino acids 96-109 of SEQ ID NO: 1; b) amino acids 96-109 of SEQ ID NO: 2; c) amino acids 96-109 of SEQ ID NO: 3; d) amino acids 96-109 of SEQ ID NO: 4; e) amino acids 97-110 of SEQ ID NO: 5; f) amino acids 97-111 of SEQ ID NO: 6; g) amino acids 97-111 of SEQ ID NO: 7; h) amino acids 97-111 of SEQ ID NO: 8; i) amino acids 96-112 of SEQ ID NO: 9; j) amino acids 96-112 of SEQ ID NO: 10; k) amino acids 96-114 of SEQ ID NO: 11; l) amino acids 96-112 of SEQ ID NO: 12; m) amino acids 97-113 of SEQ ID NO: 13; n) amino acids 97-113 of SEQ ID NO: 14; o) amino acids 97-114 of SEQ ID NO: 15; p) amino acids 96-107 of SEQ ID NO: 16; q) amino acids 97-113 of SEQ ID NO: 17; r) amino acids 97-114 of SEQ ID NO: 18; s) amino acids 97-113 of SEQ ID NO: 19; t) amino acids 96-111 of SEQ ID NO: 20; u) amino acids 96-102 of SEQ ID NO: 21; v) amino acids 96-110 of SEQ ID NO: 22; w) amino acids 95-104 of SEQ ID NO: 23; x) amino acids 96-107 of SEQ ID NO: 24; y) amino acids 100-110 of SEQ ID NO: 25; z) amino acids 96-117 of SEQ ID NO: 26; aa) amino acids 97-108 of SEQ ID NO: 27; bb) amino acids 96-112 of SEQ ID NO: 28; cc)

amino acids 97-115 of SEQ ID NO: 29; dd) amino acids 97-121 of SEQ ID NO: 30, and wherein the monoclonal antibody specifically binds a Norovirus polypeptide. The monoclonal antibody can be a $V_HH$ monoclonal antibody.

Some embodiments provide nucleic acids encoding these antibodies, expression vectors including the nucleic acids, and isolated host cells that express the nucleic acids.

In further embodiments, methods are also disclosed for detecting the presence of a NoV in a biological sample, such as Genogroup I and Genogroup II NoVs. These methods can detect a NoV infection in a subject. In a specific non-limiting example, NoV infection is a Norwalk virus infection or an MD2004 virus infection. These methods include contacting a biological sample of interest with an antibody disclosed herein, or an antigen binding fragment, and detecting binding of the antibody to the biological sample.

In other embodiments, methods are disclosed for treating and/or preventing a NoV infection and/or disease. The methods can be used to treat and or prevent a Genogroup I and Genogroup II NoV infection, such as a NV infection or a MD2004 virus infection in a subject. These methods include administering to the subject a therapeutically effective amount of an antibody disclosed herein or antigen binding fragment thereof, or a nucleic acid encoding the antibody or antigen binding fragment, thereby treating or preventing the infection and/or disease.

The foregoing and other features and advantages of the invention will become more apparent from the following detailed description of several embodiments which proceeds with reference to the accompanying figures.

BRIEF DESCRIPTION OF THE FIGURES

FIG. 1A. Antibody titers and number of ASC specific to VLPs of Norwalk strain (GI.1) detected in the blood of the immunized llamas. FIG. 1B. Antibody titers and number of ASC specific to VLPs of MD2004 strain (G114) detected in the blood of the immunized llamas. Antibody titers were measured by ELISA (lines) and the number of ASC were measured by ELISPOT (bars) using recombinant NoV VLPs Norwalk and MD2004.

FIG. 2A. Carbohydrate blockade assay. Synthetic carbohydrates H1 for Norwalk VLPs (GI.1) or H3 for MD145 VLPs (GII.4). FIG. 2B. PGM type III blockade assay. PGM type III for Norwalk or MD2004 VLPs (GII.4). FIG. 2C. Saliva (antigen Ly+) blockade assay. Saliva for Norwalk or MD145 VLPs. Sigmoidal curves were fit to the mean percent control binding calculated by comparing the amount of VLP bound to each source of carbohydrate in the presence of $V_HH$ pretreatment to the amount of VLP bound in the absence of pretreatment.

FIG. 4A. GI specific $V_HH$s. FIG. 4B. GII specific $V_HH$s.

FIGS. 5A-5B. Competition assay between $V_HH$s. The images show immunofluorescence staining of Vero cells expressing NoV VP1 from Norwalk strain (FIG. 5A, GI specific $V_HH$s 6.3 and 10.4) or MD2004 strain (FIG. 5B, GII specific $V_HH$s 1 and 5.4). Ten µg of an unlabeled $V_HH$ together with 1 µl of Alexa Fluor 568 labeled $V_HH$ were incubated onto the fixed cells. A decrease in the fluorescent signal indicates the impaired binding of the labeled $V_HH$.

FIG. 6B. Linear epitope of $V_HH$ 7.5 within the VP1 dimer. Light grey color corresponds to P1 subdomain, dark grey corresponds to P2 subdomain of VP1 and the putative epitope is shown in lower left and right corner in very dark grey.

FIGS. 7A-7B. Epitope mapping of clone 16 specific for MD2004 strain. FIG. 7A. Immunofluorescence assay. Expression of MD2004 VP1 mutants in Vero cells. The images show immunofluorescence staining of Vero cells transfected with DNA constructs pCI carrying VP1 from wild type MD2004 and 5 P domain mutants: E376Q; G340A, N368T, V389I, V340/E376. $V_HH$ 16 binding was detected with rabbit anti-$V_HH$ polyclonal serum and anti-rabbit IgG labeled with ALEXA FLUOR® 488. Labeled MAb TV20 directed to the S domain was used as positive control. FIG. 7B. Schematic diagram of the amino acids involved in $V_HH$ 16 epitope: Light grey color corresponds to P1 subdomain, dark grey corresponds to P2 subdomain of VP1 and the amino acids involved in the epitope are shown in dark grey.

FIG. 8. $V_HH$s specific to GI or GII NoV VP1. Protein sequence of the $V_HH$ antibody fragments selected by phage display. The four framework regions (FR) and the three complementary determining regions (CDR) are indicated with brackets; the two canonical cysteines are boxed. The sequences shown are SEQ ID NOs: 1-30. The top bracket shows the sequences of antibodies that bind GII, and the bottom bracket shows the sequences of antibodies that bind GI.

FIG. 9A-9B. Western blots. FIG. 9A. Detection of NoV VLPs by Western Blot by the $V_HH$s. FIG. 9B. Western Blot detection of GII NoV VLPs by the 7.5 $V_HH$.

SEQUENCE LISTING

Figure 1A:
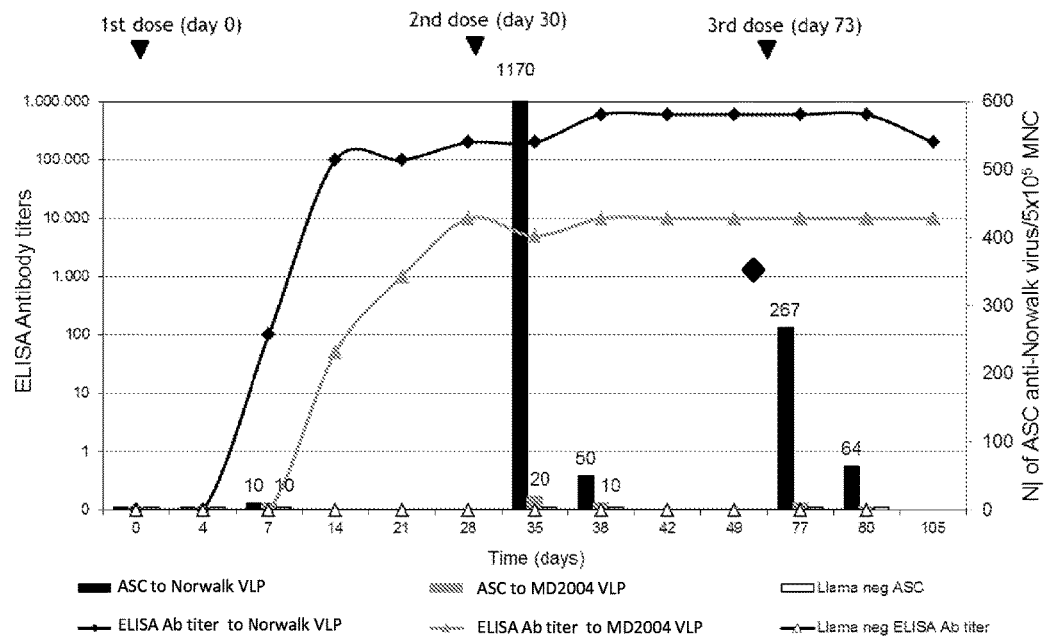
FIGS. 1A-1B. Llama immunization and immune response to NoV VLPs Norwalk (GI.1) and MD2004 (GII.4). The schedule for immunization (▼), sample collection and final bleeding (♦) is shown. The evaluation of NoV Ab response in serum during the time course of immunization is depicted.

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file in the form of the file named "4239-92920-05_Sequence_Listing.txt" (~55.5 KB), which was created on Nov. 5, 2015, and is incorporated by reference herein. In the accompanying Sequence Listing:

DETAILED DESCRIPTION OF SEVERAL EMBODIMENTS

Camelid monoclonal antibodies, specifically a $V_HH$, or nanobody that specifically binds a NoV and/or a NoV protein are disclosed herein. In certain embodiments, the monoclonal V$_H$H antibody or nanobody is produced by the camelid, such as a llama, following immunization with a NoV, a NoV protein, or a peptide fragment thereof. Alternatively, the camelid V$_H$H monoclonal antibody is engineered, i.e., produced by selection for example from a library of phage displaying appropriately mutagenized V$_H$H monoclonal antibodies using panning procedures with a NoV and/or a protein component thereof as a target. Engineered V$_H$H antibodies can further be customized by genetic engineering to have a half-life in a recipient subject, such as to increase half-life from 45 minutes to two weeks. In a specific embodiment, the CDRs of a V$_H$H monoclonal antibody are grafted onto human framework sequences to produced human antibody with the specificity of the V$_H$H.

A region of the camelid antibody which is the small single variable domain identified as V$_H$H can be obtained by genetic engineering to yield a small protein having high affinity for a target, resulting in a low molecular weight antibody-derived protein known as a "camelid nanobody" or a "V$_H$H." See U.S. Pat. No. 5,759,808, issued Jun. 2, 1998; see also Stijlemans, et al., J Biol Chem 279: 1256-61, 2004; Dumoulin et al., Nature 424: 783-8, 2003; Pleschberger et al., Bioconjugate Chem 14: 440-8, 2003; Cortez-Retamozo et al., Int J Cancer 89: 456-62, 2002; and Lauwereys et al., EMBO J 17: 3512-3520, 1998. Without being bound by theory, a V$_H$H monoclonal antibody has a molecular weight approximately one-tenth that of a human IgG molecule, and the protein has a physical diameter of only a few nanometers. One consequence of the small small size is the ability of the V$_H$H monoclonal antibody to bind to antigenic sites that are functionally invisible to larger antibody proteins, such that V$_H$H monoclonal antibodies are useful as reagents to detect antigens that are otherwise cryptic using classical immunological techniques, and thus are of use as therapeutic agents. Thus yet another consequence of small size is that a camelid V$_H$H monoclonal antibody can inhibit as a result of binding to a specific site in a groove or narrow cleft of a target protein, and hence can serve in a capacity that more closely resembles the function of a classical low molecular weight drug than that of a classical antibody.

Without being bound by theory, low molecular weight and compact size further result in camelid V$_H$H monoclonal antibodies being extremely thermostable, stable to extreme pH and to proteolytic digestion, and poorly antigenic. Another consequence is that camelid nanobodies readily move from the circulatory system into tissues, and even cross the blood-brain barrier and can treat disorders that affect nervous tissue. Nanobodies can further facilitate drug transport across the blood brain barrier (see U.S. Patent Application No. 20040161738). Further, these molecules can be fully expressed in prokaryotic cells such as *E. coli* and are expressed as fusion proteins with bacteriophage and are functional. Thus, the presently disclosed V$_H$H monoclonal antibodies and antigen binding fragments are of use both as therapeutics and in diagnostic assays for a NoV.

Terms

Unless otherwise noted, technical terms are used according to conventional usage. Definitions of common terms in molecular biology may be found in Lewin, Genes V, published by Oxford University Press, (ISBN 0-19-854287-9), 1994; Kendrew et al. (eds.), The Encyclopedia of Molecular Biology, published by Blackwell Science Ltd., (ISBN 0-632-02182-9), 1994; and Meyers (ed.), Molecular Biology and Biotechnology: a Comprehensive Desk Reference, published by VCH Publishers, Inc., (ISBN 1-56081-569-8, 1995). Unless otherwise explained, all technical and scientific terms used herein have the same meaning as commonly understood by one of ordinary skill in the art to which this disclosure belongs.

Administration: The introduction of a composition into a subject by a chosen route. Administration can be local or systemic. For example, if the chosen route is intravenous, the composition is administered by introducing the composition into a vein of the subject. The chosen route can, in some examples, be oral administration. In some examples a disclosed V$_H$H monoclonal antibody specific for a NoV, such as a Norwalk virus, is administered to a subject.

Agent: Any substance or any combination of substances that is useful for achieving an end or result; for example, a substance or combination of substances useful for inhibiting a NoV infection in a subject. Agents include, and are not limited to, proteins, nucleic acid molecules, compounds, small molecules, organic compounds, inorganic compounds, or other molecules of interest. An agent can include a therapeutic agent (such as an anti-viral agent), a diagnostic agent or a pharmaceutical agent. In some embodiments, the agent is a polypeptide agent (such as a neutralizing antibody), or an anti-viral agent. The skilled artisan will understand that particular agents may be useful to achieve more than one result.

Amino acid substitution: The replacement of one amino acid in peptide with a different amino acid.

Amplification: A technique that increases the number of copies of a nucleic acid molecule (such as an RNA or DNA). An example of amplification is the polymerase chain reaction, in which a biological sample is contacted with a pair of oligonucleotide primers, under conditions that allow for the hybridization of the primers to a nucleic acid template in the sample. The primers are extended under suitable conditions, dissociated from the template, and then re-annealed, extended, and dissociated to amplify the number of copies of the nucleic acid. The product of amplification can be characterized by electrophoresis, restriction endonuclease cleavage patterns, oligonucleotide hybridization or ligation, and/or nucleic acid sequencing using standard techniques. Other examples of amplification include strand displacement amplification, as disclosed in U.S. Pat. No. 5,744,311; transcription-free isothermal amplification, as disclosed in U.S. Pat. No. 6,033,881; repair chain reaction amplification, as disclosed in PCT Publication No. WO 90/01069; ligase chain reaction amplification, as disclosed in European Patent Publication EP-A-320 308; gap filling ligase chain reaction amplification, as disclosed in U.S. Pat. No. 5,427,930; and NASBA™ RNA transcription-free amplification, as disclosed in U.S. Pat. No. 6,025,134.

Animal: Living multi-cellular vertebrate organisms, a category that includes, for example, mammals and birds. The term mammal includes both human and non-human mammals, such as camelids. Similarly, the term "subject" includes both human and veterinary subjects.

Antibody: A polypeptide substantially encoded by an immunoglobulin gene or immunoglobulin genes, or antigen binding fragments thereof, which specifically binds and recognizes an analyte (antigen) such as, but not limited to, a NoV polypeptide, such as a NV polypeptide. The antibody can specifically bind VP1, or an immunogenic fragment thereof, for example the P1 or P2 domain Immunoglobulin genes include the kappa, lambda, alpha, gamma, delta, epsilon and mu constant region genes, as well as the myriad immunoglobulin variable region genes.

In several embodiments, in primates such as humans, a heavy and the light chain variable domain of an antibody combine to specifically bind the antigen. Generally, a naturally occurring primate (e.g., human) or murine immunoglobulin has heavy (H) chains and light (L) chains interconnected by disulfide bonds. There are two types of light chain, lambda (λ) and kappa (κ). There are five main heavy chain classes (or isotypes) which determine the functional activity of an antibody molecule: IgM, IgD, IgG, IgA and IgE. Primate antibodies can be class switched.

In some embodiments, only the heavy chain variable domain is required for antigen binding. For example, naturally occurring camelid antibodies consisting of a heavy chain only are functional and stable in the absence of light chain (see, e.g., Hamers-Casterman et al., Nature, 363:446-448, 1993; Sheriff et al., Nat. Struct. Biol., 3:733-736, 1996). Specifically, antibody proteins obtained from members of the camel and dromedary (*Camelus bactrianus* and *Calelus dromaderius*) family including new world members such as llama species (*Lama paccos, Lama glama* and *Lama vicugna*) have been characterized with respect to size, structural complexity and antigenicity for human subjects. Certain IgG antibodies from this family of mammals as found in nature lack light chains, and are thus structurally distinct from the typical four chain quaternary structure having two heavy and two light chains, for antibodies from other animals. See PCT/EP93/02214 (WO 94/04678 published 3 Mar. 1994).

Light and heavy chain variable domains contain a "framework" region interrupted by three hypervariable regions, also called "complementarity-determining regions" or "CDRs" (see, e.g., Kabat et al., *Sequences of Proteins of Immunological Interest*, U.S. Department of Health and Human Services, 1991). The sequences of the framework regions of different light or heavy chains are relatively conserved within a species. The framework region of an antibody, that is the combined framework regions of the constituent light and heavy chains, serves to position and align the CDRs in three-dimensional space. The CDRs are primarily responsible for antigen binding.

References to "$V_H$" or "VH" refer to the variable region of an immunoglobulin heavy chain, including that of an antibody fragment. References to "$V_L$" or "VL" refer to the variable region of an immunoglobulin light chain, such as in a primate antibody. References to "$V_HH$" or "VHH" refer to the variable region of a "heavy chain immunoglobulin."

The CDRs are typically referred to as CDR1, CDR2, and CDR3 (from the N-terminus to C-terminus), and are also typically identified by the chain in which the particular CDR is located. Thus, a $V_H$ CDR3 is located in the variable domain of the heavy chain of the antibody in which it is found, whereas a $V_L$ CDR1 is the CDR1 from the variable domain of the light chain of the antibody in which it is found. Light chain CDRs are sometimes referred to as CDR L1, CDR L2, and CDR L3. Heavy chain CDRs are sometimes referred to as CDR H1, CDR H2, and CDR H3. $V_HH$ monoclonal antibodies have only a heavy chain, and thus include only one CDR1, CDR2 and CDR3. Generally, the CDR3 is primarily responsible for antigen specificity. The sequences of the framework regions of different light or heavy chains are relatively conserved within a species. The framework region of an antibody, that is the combined framework regions of the constituent light and heavy chains, serves to position and align the CDRs in three-dimensional space.

Camelids produce a unique antibody molecule. Some IgG subtypes of the llamas lack the light chains and the $CH_1$ domain and are called heavy chain antibodies.

Each light and heavy chain of any antibody, contains constant domains and variable domains. Light and heavy chain variable domains, are named $V_L$ and $V_H$ respectively, while the variable domain of a heavy chain antibody is called $V_HH$. The $V_HH$ is composed of only one polypeptide chain of 15 kDa and is considered the smallest known natural domain with full antigen-binding capacity.

Any variable domain includes in an N- to C-direction, the following structural regions: N-FR1-CDR1-FR2-CDR2-FR3-CDR3-FR4-C, wherein FR denotes a framework region amino acid sequence and CDR denotes a complementary determining region amino acid sequence (see, e.g., Kabat et al., Sequences of Proteins of Immunological Interest, U.S. Department of Health and Human Services, 1991). In specific non-limiting examples, the CDR3 comprises a llama CDR3 $V_HH$ domain amino acid sequence; and wherein the antibody binds to Norovirus.

The extent of the framework region and CDRs have been defined (see, Kabat et al., Sequences of Proteins of Immunological Interest, U.S. Department of Health and Human Services, 1991, which is hereby incorporated by reference in its entirety). The CDRs of the heavy chain variable domain are located at residues 31-35 (CDR-HD, residues 50-65 (CDR-H2) and residues 95-102 (CDR-H3) according to the Kabat numbering system. However, according to Chothia (Chothia and Lesk, J. Mol. Biol., 196: 901-17, 1987), the loop equivalent to CDR-H1 extends from residue 26 to residue 32. Thus "CDR-H1", as used herein, comprises residues 26 to 33, as described by a combination of the Kabat numbering system and Chothia's topological loop definition. In antibodies (such as primate antibodies) that include a light chain, such as a primate antibody, the CDRs of the light chain variable domain are located at residues 24-34 (CDR-L1), residues 50-56 (CDR-L2) and residues 89-97 (CDR-L3) according to the Kabat numbering system. Lefranc, et al. ("IMGT unique numbering for immunoglobulin and T cell receptor variable domains and Ig superfamily V-like domains," Dev. Comp. Immunol., 27:55-77, 2003) discloses the "IMGT" numbering scheme for CDRs. The Kabat database is now maintained online. The location of camelid CDRs can also be determined (see, for example, Sircar et al., J. Immunol. 186: 6357-6367, 2011); a program to determine camelid antibody structure, the RosettaAntibody program, is available on the internet.

A "monoclonal antibody" is an antibody produced by a single clone of B-lymphocytes or by a cell into which the heavy chain gene (and optionally a light chain gene, such as for a primate antibody) of a single antibody have been transfected.

In some embodiments, the $V_HH$ molecules can be produced as recombinant monoclonal antibodies or antigen binding fragments in different expression platforms, avoiding the use of hybridomas and mice. $V_HH$ monoclonal antibodies can be humanized monoclonal antibodies. In some embodiments, monoclonal antibodies can be chimeric antibodies.

A "chimeric" antibody is an antibody which includes sequences from two different antibodies, which typically are of different species. In some examples, a chimeric antibody includes one or more CDRs and/or framework regions from one llama $V_HH$ and CDRs and/or framework regions from another llama $V_HH$. In some embodiments, a chimeric antibody comprises heavy and/or light chain variable regions derived from a first species and heavy and/or light chain constant regions derived from a second species. In some embodiments, the variable and constant regions of the light chain are derived from a first species (for example, a primate, such as a human) while the variable region of the heavy chain is derived from a second species (for example, a llama) and the constant region of the heavy chain is derived from the first species.

A "humanized" antibody is an antibody including a human framework region and one or more CDRs from a non-human (such as a camelid, chimpanzee, mouse, rat, llama or synthetic) immunoglobulin. The non-human antibody providing the CDRs is termed a "donor," and the human antibody providing the framework is termed an "acceptor." In one embodiment, all the CDRs are from the donor antibody in a humanized antibody. Constant regions need not be present, but if they are, they must be substantially identical to human antibody constant regions, such as at least about 85-90%, such as about 95% or more identical. Hence, all parts of a humanized antibody, except possibly the CDRs, are substantially identical to corresponding parts of natural human antibody sequences. A "humanized antibody" can include a humanized light chain and a humanized heavy chain. A humanized antibody binds to the same antigen as the donor antibody that provides the CDRs. The acceptor framework of a humanized antibody may have a limited number of substitutions by amino acids taken from the donor framework. Humanized or other monoclonal antibodies can have additional conservative amino acid substitutions which have substantially no effect on antigen binding or other immunoglobulin functions. Humanized immunoglobulins can be constructed by means of genetic engineering (for example, see U.S. Pat. No. 5,585,089).

A $V_HH$ antibody is easily humanized, although camelid antibodies have high homology with the human VH domain. In some embodiments, a humanized $V_HH$ has amino acid mutations in specific sites of the FRs regions, for example, see PCT Publication No, WO2013030604 A1, incorporated by reference herein).

A "neutralizing antibody" is an antibody which reduces the infectious titer of an infectious agent by binding to a specific antigen on the infectious agent. In some examples the infectious agent is a virus. In some examples, an antibody that is specific for a NoV, such as a Norwalk virus, neutralizes the infectious titer of the virus or demonstrates ability to block norovirus VLPs binding to ligands in a surrogate neutralization assays.

Two chain antibodies, such as primate antibodies exist, for example, as intact immunoglobulins and as a number of well-characterized fragments produced by digestion with various peptidases. For instance, with regard to two-chain antibodies, such as primate (e.g., human) and murine antibodies, Fabs, Fvs, scFvs that specifically bind to a NoV polypeptide, for example VP1, or fragments of this polypeptide, are specific binding agents. A scFv protein is a fusion protein in which a light chain variable region of an immunoglobulin and a heavy chain variable region of an immunoglobulin are bound by a linker, while in dsFvs, the chains have been mutated to introduce a disulfide bond to stabilize the association of the chains. The term also includes genetically engineered forms such as chimeric antibodies and heteroconjugate antibodies such as bispecific antibodies. See also, Pierce Catalog and Handbook, 1994-1995 (Pierce Chemical Co., Rockford, Ill.); Kuby, Immunology, $3^{rd}$ Ed., W.H. Freeman & Co., New York, 1997.

Conventional antibody fragments of two chain molecules include, but are not limited to, the following: (1) Fab, the fragment which contains a monovalent antigen-binding fragment of an antibody molecule produced by digestion of whole antibody with the enzyme papain to yield an intact light chain and a portion of one heavy chain; (2) Fab', the fragment of an antibody molecule obtained by treating whole antibody with pepsin, followed by reduction, to yield an intact light chain and a portion of the heavy chain; two Fab' fragments are obtained per antibody molecule; (3) (Fab')$_2$, the fragment of the antibody obtained by treating whole antibody with the enzyme pepsin without subsequent reduction; (4) F(ab')$_2$, a dimer of two Fab' fragments held together by two disulfide bonds; (5) Fv, a genetically engineered fragment containing the variable region of the light chain and the variable region of the heavy chain expressed as two chains; and (6) single chain antibody ("SCA"), a genetically engineered molecule containing the variable region of the light chain, the variable region of the heavy chain, linked by a suitable polypeptide linker as a genetically fused single chain molecule.

Camelids produce a unique antibody molecule. Some IgG subtypes of the llamas lack the light chain and are called heavy chain antibodies; the variable domain of these antibodies is called $V_HH$ and is comprised of only one polypeptide chain. The $V_HH$ domain is a molecule of 15 kDa that is considered the smallest known natural domain with full antigen-binding capacity. The DNA encoding the $V_HH$ region can be obtained and modified by genetic engineering to yield a small protein having high affinity for a target, resulting in a low molecular weight antibody-derived protein known as a camelid "nanoantibody" or "nanobody". There is no Fc region nor $V_L$ domain in a recombinant $V_HH$. See U.S. Pat. No. 5,759,808 issued Jun. 2, 1998; see also Stijlemans et al., J Biol Chem 279: 1256-1261, 2004; Dumoulin et al., Nature 424: 783-788, 2003; Pleschberger et al., Bioconjugate Chem 14: 440-448, 2003; Cortez-Retamozo et al. Int J Cancer 89: 456-62, 2002; and Lauwereys et al., EMBO J 17: 3512-3520, 1998.

Antigen binding fragments of an antibody can be produced by the modification of whole antibodies or those synthesized de novo using recombinant DNA methodologies. In some examples, the term antibody includes the amino acid sequences of one or more of the CDRs from the antibody grafted onto a scaffold.

Antigen: A compound, composition, or substance that can stimulate the production of antibodies or a T cell response in an animal, including compositions that are injected or absorbed into an animal. An antigen reacts with the products of specific humoral or cellular immunity, including those induced by heterologous antigens, such as the disclosed antigens. "Epitope" or "antigenic determinant" refers to the region of an antigen to which B and/or T cells respond. In one embodiment, T cells respond to the epitope, when the epitope is presented in conjunction with an MHC molecule. Epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5, about 9, or about 8-10 amino acids in a unique spatial conformation. Methods of determining spatial conformation of epitopes include, for example, x-ray crystallography and nuclear magnetic resonance.

Examples of antigens include, but are not limited to, peptides, lipids, polysaccharides, and nucleic acids containing antigenic determinants, such as those recognized by an immune cell. In some examples, antigens include peptides derived from a pathogen of interest. Exemplary pathogens include bacteria, fungi, viruses and parasites. In some embodiments, an antigen is derived from a NoV, such as a Norwalk virus or a MD2004 virus. In some embodiments, the antigen is a NoV VP1 polypeptide or antigenic fragment thereof, such as a P1 or P2 domain.

A "target epitope" is a specific epitope on an antigen that specifically binds an antibody of interest, such as a monoclonal antibody. In some examples, a target epitope includes the amino acid residues that contact the antibody of interest, such that the target epitope can be selected by the amino acid residues determined to be in contact with the antibody.

Binding affinity: Affinity of an antibody, such as a $V_HH$ monoclonal antibody, or antigen binding fragment thereof for an antigen. In one embodiment, affinity is calculated by a modification of the Scatchard method described by Frankel et al., *Mol. Immunol.*, 16:101-106, 1979. In another embodiment, binding affinity is measured by an antigen/antibody dissociation rate. In yet another embodiment, a high binding affinity is measured by a competition radioimmunoassay or by Plasmon resonance in a BIOCORE. In several examples, a high binding affinity is at least about $1 \times 10^{-8}$ M. In other embodiments, a high binding affinity is at least about $1.5 \times 10^{-8}$, at least about $2.0 \times 10^{-8}$, at least about $2.5 \times 10^{-8}$, at least about $3.0 \times 10^{-8}$, at least about $3.5 \times 10^{-8}$, at least about $4.0 \times 10^{-8}$, at least about $4.5 \times 10^{-8}$, or at least about $5.0 \times 10^{-8}$ M.

The antigen specificity and affinity of $V_HH$ antibodies from immune libraries are of good quality. Kinetick (k)on and koff rate constants are generally in the range of $10^5$ to $10^6$ $M^{-1}s^{-1}$ and $10^{-2}$ to $10^{-4}$ $s^{-1}$, respectively, such that low nanomolar or even picomolar equilibrium dissociation constants are obtained. Such affinity parameters are excellent for most applications (Muyldermans, Annu. Rev. Biochem. 2013. 82:775-97, 2013).

Capsid protein (VP1): A capsid polypeptide that is encoded by open reading frame (ORF) 2 of the NoV genome; the polypeptide itself assembles to form an icosahedral capsid. When the protein is 530 amino acids in length, the shell (S) domain (amino acids 1-225) contains elements necessary for the formation of the icosahedron. The Protruding domain (P, amino acids 225-530) is divided into sub-domains P1 (amino acids 226-278 (P1 subdomain 1) and 406-530 (P1 subdomain 2) and P2 (amino acids 279-405). The P domain interacts in dimeric contacts that increase the stability of the capsid and form the protrusions on the virion. The P2 domain is hypervariable. An exemplary VP1 is provided in UNIPROT Accession No. Q83884 (for example, CAPSD_NVN68, Oct. 3, 2012), which is incorporated herein by reference.

Clonal variant: Any sequence, which differs by one or more nucleotides or amino acids, in presence of V region with identical mutations compared to the germline, identical VDJ or VJ gene usage, and identical D and J length. The "germline" sequence is intended to be the sequence coding for the antibody/immunoglobulin (or of any fragment thereof) deprived of mutations, for example somatic mutations. The percentage of homology represents an indication of the mutational events which any type of heavy chain portion undergoes after contact with an antigen.

Computer readable media: Any medium or media, which can be read and accessed directly by a computer, so that the media is suitable for use in a computer system. Such media include, but are not limited to: magnetic storage media such as floppy discs, hard disc storage medium and magnetic tape; optical storage media such as optical discs or CD-ROM; electrical storage media such as RAM and ROM; and hybrids of these categories such as magnetic/optical storage media.

Conjugate: A complex of two molecules linked together, for example, linked together by a covalent bond. In one embodiment, an antibody is linked to an effector molecule; for example, an antibody, such as a $V_HH$ monoclonal antibody, that specifically binds to a NoV polypeptide, such as a NV polypeptide, covalently linked to an effector molecule or to a toxin. The linkage can be by chemical or recombinant means. In one embodiment, the linkage is chemical, wherein a reaction between the antibody moiety and the effector molecule has produced a covalent bond formed between the two molecules to form one molecule. A peptide linker (short peptide sequence) can optionally be included between the antibody and the effector molecule. Because conjugates can be prepared from two molecules with separate functionalities, such as an antibody and an effector molecule, they are also sometimes referred to as "chimeric molecules." In one embodiment, an antibody linked to an effector molecule is further joined to a lipid or other molecule to a protein or peptide to increase its half-life in the body.

Contacting: Placement in direct physical association; includes both in solid and liquid form, which can take place either in vivo or in vitro. Contacting includes contact between one molecule and another molecule, for example the amino acid on the surface of one polypeptide, such as an antigen, that contacts another polypeptide, such as an antibody. Contacting can also include contacting a cell for example by placing an antibody in direct physical association with a cell.

Control: A reference standard. In some embodiments, the control is a sample obtained from a healthy patient. In other embodiments, the control is a tissue sample obtained from a patient diagnosed with a NoV infection, such as a Norwalk virus infection that serves as a positive control. In still other embodiments, the control is a historical control or standard reference value or range of values (such as a previously tested control sample, such as a group of infected patients with known prognosis or outcome, or group of samples that represent baseline or normal values).

A difference between a test sample and a control can be an increase or conversely a decrease. The difference can be a qualitative difference or a quantitative difference, for example a statistically significant difference. In some examples, a difference is an increase or decrease, relative to a control, of at least about 5%, such as at least about 10%, at least about 20%, at least about 30%, at least about 40%, at least about 50%, at least about 60%, at least about 70%, at least about 80%, at least about 90%, at least about 100%, at least about 150%, at least about 200%, at least about 250%, at least about 300%, at least about 350%, at least about 400%, at least about 500%, or greater than 500%.

Detectable marker: A detectable molecule (also known as a label) that is conjugated directly or indirectly to a second molecule, such as an antibody, to facilitate detection of the second molecule. For example, the detectable marker can be capable of detection by ELISA, spectrophotometry, flow cytometry, microscopy or diagnostic imaging techniques (such as CT scans, MRIs, ultrasound, fiberoptic examination, and laparoscopic examination). Non-limiting examples of detectable markers include fluorophores, fluorescent proteins, chemiluminescent agents, enzymatic linkages, radioactive isotopes and heavy metals or compounds (for example super paramagnetic iron oxide nanocrystals for detection by MRI). In one example, a "labeled antibody" refers to incorporation of another molecule in the antibody. For example, the label is a detectable marker, such as the incorporation of a radiolabeled amino acid or attachment to a polypeptide of biotinyl moieties that can be detected by marked avidin (for example, streptavidin containing a fluorescent marker or enzymatic activity that can be detected by optical or colorimetric methods). Various methods of labeling polypeptides and glycoproteins are known in the art and may be used. Examples of labels for polypeptides include, but are not limited to, the following: radioisotopes or radionuclides (such as $^{35}$S or $^{131}$I), fluorescent labels (such as fluorescein isothiocyanate (FITC), rhodamine, lanthanide phosphors. ALEXA FLUOR®), enzymatic labels (such as horseradish peroxidase, beta-galactosidase, luciferase, alkaline phosphatase), chemiluminescent markers, biotinyl groups, predetermined polypeptide epitopes recognized by a secondary reporter (such as a leucine zipper pair sequences, binding sites for secondary antibodies, metal binding domains, epitope tags), or magnetic agents, such as gadolinium chelates. In some embodiments, labels are attached by spacer arms of various lengths to reduce potential steric hindrance. Methods for using detectable markers and guidance in the choice of detectable markers appropriate for various purposes are discussed for example in Sambrook et al. (Molecular Cloning: A Laboratory Manual, Cold Spring Harbor, N.Y., 1989) and Ausubel et al. (In Current Protocols in Molecular Biology, John Wiley & Sons, New York, 1998).

Detecting: To identify the existence, presence, or fact of something. General methods of detecting are known to the skilled artisan (see, for example, U.S. Pat. No. 7,635,476) and may be supplemented with the protocols and reagents disclosed herein. For example, included herein are methods of detecting a cell that expresses a NoV polypeptide, such as a Norwalk virus polypeptide, for example, VP1, in a subject. In some embodiments, the peptide can be VP1.

Effector molecule: The portion of a chimeric molecule that is intended to have a desired effect on a cell to which the chimeric molecule is targeted. Effector molecule is also known as an effector moiety, therapeutic agent, or diagnostic agent, or similar terms.

Epitope: An antigenic determinant. These are particular chemical groups or peptide sequences on a molecule that are antigenic, i.e. that elicit a specific immune response. An antibody specifically binds a particular antigenic epitope on a polypeptide. In some examples a disclosed antibody specifically binds to an epitope on the surface of VP1 from a NoV, such as the P2 subdomain.

Framework Region: Amino acid sequences interposed between CDRs. The term includes variable light and variable heavy framework regions. The framework regions serve to hold the CDRs in an appropriate orientation for antigen binding.

Fc polypeptide: The polypeptide comprising the constant region of an antibody excluding the first constant region immunoglobulin domain. Fc region generally refers to the last two constant region immunoglobulin domains of IgA, IgD, and IgG, and the last three constant region immunoglobulin domains of IgE and IgM. An Fc region may also include part or all of the flexible hinge N-terminal to these domains. For IgA and IgM, an Fc region may or may not comprise the tailpiece, and may or may not be bound by the J chain. For IgG, the Fc region comprises immunoglobulin domains Cgamma2 and Cgamma3 (Cγ2 and Cγ3) and the lower part of the hinge between Cgamma1 (Cγ1) and Cγ2. Although the boundaries of the Fc region may vary, the human IgG heavy chain Fc region is usually defined to comprise residues C226 or P230 to its carboxyl-terminus, wherein the numbering is according to the EU index as in Kabat. For IgA, the Fc region comprises immunoglobulin domains Calpha2 and Calpha3 (Cα2 and Cα3) and the lower part of the hinge between Calphal (Cα1) and Cα2. Encompassed within the definition of the Fc region are functionally equivalent analogs and variants of the Fc region. A functionally equivalent analog of the Fc region may be a variant Fc region, comprising one or more amino acid modifications relative to the wild-type or naturally existing Fc region. Variant Fc regions will possess at least 50% homology with a naturally existing Fc region, such as about 80%, and about 90%, or at least about 95% homology. Functionally equivalent analogs of the Fc region may comprise one or more amino acid residues added to or deleted from the N- or C-termini of the protein, such as no more than 30 or no more than 10 additions and/or deletions. Functionally equivalent analogs of the Fc region include Fc regions operably linked to a fusion partner. Functionally equivalent analogs of the Fc region must comprise the majority of all of the Ig domains that compose Fc region as defined above; for example IgG and IgA Fc regions as defined herein must comprise the majority of the sequence encoding $CH_2$ and the majority of the sequence encoding $CH_3$. Thus, the $CH_2$ domain on its own, or the $CH_3$ domain on its own, are not considered Fc region. The Fc region may refer to this region in isolation, or this region in the context of an Fc fusion polypeptide.

Heavy chain antibody: Antibodies obtained from members of the camel and dromedary (*Camelus bactrianus* and *Calelus dromaderius*) family including new world members such as llama species (*Lama pacos, Lama glama* and *Lama vicugna*), specifically certain IgG antibodies (of the $IgG_2$ and $IgG_3$ isotypes) that lack light chains and are thus structurally distinct from the typical four chain quaternary structure having two heavy and two light chains (See PCT Publication No. WO 94/04678, incorporated herein by reference). Naturally occurring camelid antibodies composed only by heavy chains are functional and stable in the absence of light chains (see, e.g., Hamers-Casterman et al., Nature, 363:446-448, 1993; Sheriff et al., Nat. Struct. Biol., 3:733-736, 1996). The heavy chain antibodies are composed of two constant domains in the Fc and one variable domain called $V_HH$. These antibodies lack the $CH_1$ domain of conventional antibodies (Muyldermans, Annu. Rev. Biochem. 2013. 82:775-97, 2013).

Hemagglutination: Human erythrocytes are a natural source of human histo-blood group antigens (HBGA) ligands. NoV recombinant VLPs have hemagglutination activity through binding of HBGAs present in the surface of human red blood cells. Antibodies directed to the HBGA binding sites of the virus can inhibit hemagglutination (hemagglutination inhibition activity, HAI). An HAI assay can be used as an alternative to the HBGA blocking assay in order to quantitate neutralizing antibodies in a sample (Czako et al. Clinical and Vaccine Immunology, 19(2), 284-7, 2012).

Host cells: Cells in which a vector can be propagated and its DNA expressed, for example a disclosed antibody can be expressed in a host cell. The cell may be prokaryotic or eukaryotic. The term also includes any progeny of the subject host cell. It is understood that all progeny may not be identical to the parental cell since there may be mutations that occur during replication. However, such progeny are included when the term "host cell" is used.

IgG: A polypeptide belonging to the class or isotype of antibodies that are substantially encoded by a recognized immunoglobulin gamma gene. In humans, this class comprises $IgG_1$, $IgG_2$, $IgG_3$, and $IgG_4$. In camelids, this class comprises $IgG_1$, $IgG_2$, and $IgG_3$.

Immune complex: The binding of antibody to a soluble antigen forms an immune complex. The formation of an immune complex can be detected through conventional methods known to the skilled artisan, for instance immunohistochemistry, immunoprecipitation, flow cytometry, immunofluorescence microscopy, ELISA, immunoblotting (for example, Western blot), magnetic resonance imaging, CT scans, X-ray and affinity chromatography Immunological binding properties of selected antibodies may be quantified using methods well known in the art.

Immunoadhesin: A molecular fusion of a protein with the Fc region of an immunoglobulin, wherein the immunoglobulin retains specific properties, such as Fc receptor binding and increased half-life. An Fc fusion combines the Fc region of an immunoglobulin with a fusion partner, which in general can be any protein, polypeptide, peptide, or small molecule. In one example, an immunoadhesin includes the hinge, $CH_2$, and $CH_3$ domains of the immunoglobulin gamma 1 heavy chain constant region. In another example, the immunoadhesin includes the $CH_2$, and $CH_3$ domains of an IgG.

Immunologically reactive conditions: Includes reference to conditions which allow an antibody raised against a particular epitope to bind to that epitope to a detectably greater degree than, and/or to the substantial exclusion of, binding to substantially all other epitopes. Immunologically reactive conditions are dependent upon the format of the antibody binding reaction and typically are those utilized in immunoassay protocols or those conditions encountered in vivo. See Harlow & Lane, supra, for a description of immunoassay formats and conditions. The immunologically reactive conditions employed in the methods are "physiological conditions" which include reference to conditions (e.g., temperature, osmolarity, pH) that are typical inside a living mammal or a mammalian cell. While it is recognized that some organs are subject to extreme conditions, the intra-organismal and intracellular environment normally lies around pH 7 (e.g., from pH 6.0 to pH 8.0, more typically pH 6.5 to 7.5), contains water as the predominant solvent, and exists at a temperature above 0° C. and below 50° C. Osmolarity is within the range that is supportive of cell viability and proliferation.

Inhibiting or treating a disease: Inhibiting the full development of a disease or condition, for example, in a subject who is at risk for a disease such a NoV infection. "Treatment" refers to a therapeutic intervention that ameliorates a sign or symptom of a disease or pathological condition after it has begun to develop. The term "ameliorating," with reference to a disease or pathological condition, refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, a reduction in the viral load, an improvement in the overall health or well-being of the subject, or by other parameters well known in the art that are specific to the particular disease. A "prophylactic" treatment is a treatment administered to a subject who does not exhibit signs of a disease or exhibits only early signs for the purpose of decreasing the risk of developing pathology.

Isolated: An "isolated" biological component (such as a cell, for example a B-cell, a nucleic acid, peptide, protein, heavy chain domain or antibody) has been substantially separated, produced apart from, or purified away from other biological components in the cell of the organism in which the component naturally occurs, such as, other chromosomal and extrachromosomal DNA and RNA, and proteins. Nucleic acids, peptides and proteins which have been "isolated" thus include nucleic acids and proteins purified by standard purification methods. The term also embraces nucleic acids, peptides, and proteins prepared by recombinant expression in a host cell as well as chemically synthesized nucleic acids. In some examples an antibody, such as an antibody specific for a NoV polypeptide can be isolated, for example isolated from a subject infected with the virus.

$K_d$: The dissociation constant for a given interaction, such as a polypeptide ligand interaction or an antibody antigen interaction. For example, for the bimolecular interaction of an antibody (such as any of the antibodies disclosed herein) and an antigen (such as a NoV polypeptide, for example a Norwalk virus polypeptide) it is the concentration of the individual components of the bimolecular interaction divided by the concentration of the complex.

Label: A detectable compound or composition that is conjugated directly or indirectly to another molecule, such as an antibody or a protein, to facilitate detection of that molecule. Specific, non-limiting examples of labels include fluorescent tags, enzymatic linkages, and radioactive isotopes. In some examples, a disclosed antibody is labeled.

Neutralizing antibody: An antibody which reduces the infectious titer of an infectious agent by binding to a specific antigen on the infectious agent. In some examples the infectious agent is a virus, such as a NoV, for example a Genogroup I or Genogroup II NoV, such as a Norwalk virus or MD2004 virus. In some examples, an antibody that is specific for a NoV polypeptide neutralizes the infectious titer of the virus. In some examples, an antibody specific for NoV VP1 neutralizes the infectious titer of the virus. In vitro assays for neutralization are known in the art. Thus, in some non-limiting examples, an assay for neutralization activity is blocking the binding of NoV-like particles (VLPs) to HBGA synthetic carbohydrates, for example H1 or H3 type HBGA, in a dose dependent manner. In other non-limiting examples an assay for neutralization activity is blocking the binding of NoV-VLPs to pig gastric mucin or saliva, in a dose dependent manner. In other non-limiting examples, an assay for neutralization is the inhibition of hemagglutination activity.

With regard to an antigen from a pathogen, such as a virus, a "broadly neutralizing" antibody can bind to and inhibit the function of an antigen from more than one class and/or subclass of the pathogen. For example, with regard to a NoV, the antibody can bind to and inhibit the function of an antigen, such as a viral protein, from more than one genotype of NoV, including, but not limited to, NV (GI.1), P7-587(GI.1), Desert Shield virus (GI.3), Hawaii virus (GII.1), Snow Mountain virus (GII.2), Henryton virus (GII.2), CHDC2005 virus (GII.3), Toronto 24 virus (GII.3), CHDC5261 virus (GII.3), CHDC4031 virus (GII.3), Maizuru2000 virus (GII.3), Aus2001, Aus2007 and Aus2008 virus (GII.3), CHDC32 virus (GII.3), CHDC4871 virus (GII.4), Rockville virus (GII.4), MD145 virus (GII.4), MD2004 virus (GII.4), HS191 virus (GII.4), Bethesda virus (GII.6), DC119 virus (GII.7), M7 virus (GII.14) or viruses from more than one genogroup (GI-GV). In one embodiment, broadly neutralizing antibodies to NoVs are distinct from other antibodies in that they neutralize a high percentage of the many types of NoVs.

Nanoantibody or nanobody: The variable domain of a heavy chain antibody, called $V_HH$. A nanobody is comprised of only one polypeptide chain and is considered the smallest known natural domain with full antigen-binding capacity (15 kDa). The DNA encoding the $V_HH$ region may be obtained and modified by genetic engineering to yield a small recombinant protein having high affinity for a target, resulting in a low molecular weight antibody-derived protein known as a camelid "nanoantibody" or "nanobody" due to the small size. See U.S. Pat. No. 5,759,808 issued Jun. 2, 1998; see also Stijlemans et al., J Biol Chem 279: 1256-1261, 2004; Dumoulin et al., Nature 424: 783-788, 2003; Pleschberger et al., Bioconjugate Chem 14: 440-448, 2003; Cortez-Retamozo et al. Int J Cancer 89: 456-62, 2002; and Lauwereys et al., EMBO J 17: 3512-3520, 1998.

As noted above, a $V_HH$ includes in an N- to C-direction, the following structural domains regions: N-FR1-CDR1-FR2-CDR2-FR3-CDR3-FR4-C, wherein FR denotes a framework region amino acid sequence and CDR denotes a complementary determining region amino acid sequence (see, e.g., Kabat et al., Sequences of Proteins of Immunological Interest, U.S. Department of Health and Human Services, 1991). In specific non-limiting examples, the CDR3 comprises a llama CDR3 $V_HH$ domain amino acid sequence; and wherein the antibody binds to NoV. $V_HH$ monoclonal antibodies have only a heavy chain (they do not include a light chain), and thus include only one CDR1, CDR2 and CDR3. Generally, the CDR3 is primarily responsible for antigen specificity.

Nucleic acid: A polymer composed of nucleotide units (ribonucleotides, deoxyribonucleotides, related naturally occurring structural variants, and synthetic non-naturally occurring analogs thereof) linked via phosphodiester bonds, related naturally occurring structural variants, and synthetic non-naturally occurring analogs thereof. Thus, the term includes nucleotide polymers in which the nucleotides and the linkages between them include non-naturally occurring synthetic analogs, such as, for example and without limitation, phosphorothioates, phosphoramidates, methyl phosphonates, chiral-methyl phosphonates, 2-O-methyl ribonucleotides, peptide-nucleic acids (PNAs), and the like. Such polynucleotides can be synthesized, for example, using an automated DNA synthesizer. The term "oligonucleotide" typically refers to short polynucleotides, generally no greater than about 50 nucleotides. It will be understood that when a nucleotide sequence is represented by a DNA sequence (i.e., A, T, G, C), this also includes an RNA sequence (i.e., A, U, G, C) in which "U" replaces "T."

Conventional notation is used herein to describe nucleotide sequences: the left-hand end of a single-stranded nucleotide sequence is the 5'-end; the left-hand direction of a double-stranded nucleotide sequence is referred to as the 5'-direction. The direction of 5' to 3' addition of nucleotides to nascent RNA transcripts is referred to as the transcription direction. The DNA strand having the same sequence as an mRNA is referred to as the "coding strand;" sequences on the DNA strand having the same sequence as an mRNA transcribed from that DNA and which are located 5' to the 5'-end of the RNA transcript are referred to as "upstream sequences;" sequences on the DNA strand having the same sequence as the RNA and which are 3' to the 3' end of the coding RNA transcript are referred to as "downstream sequences."

"cDNA" refers to a DNA that is complementary or identical to an mRNA, in either single stranded or double stranded form.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA produced by that gene produces the protein in a cell or other biological system. Both the coding strand, the nucleotide sequence of which is identical to the mRNA sequence and is usually provided in sequence listings, and non-coding strand, used as the template for transcription, of a gene or cDNA can be referred to as encoding the protein or other product of that gene or cDNA. Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

"Recombinant nucleic acid" refers to a nucleic acid having nucleotide sequences that are not naturally joined together. This includes nucleic acid vectors comprising an amplified or assembled nucleic acid which can be used to transform a suitable host cell. A host cell that comprises the recombinant nucleic acid is referred to as a "recombinant host cell." The gene is then expressed in the recombinant host cell to produce, e.g., a "recombinant polypeptide." A recombinant nucleic acid may serve a non-coding function (e.g., promoter, origin of replication, ribosome-binding site, etc.) as well.

A first sequence is an "antisense" with respect to a second sequence if a polynucleotide whose sequence is the first sequence specifically hybridizes with a polynucleotide whose sequence is the second sequence.

Terms used to describe sequence relationships between two or more nucleotide sequences or amino acid sequences include "reference sequence," "selected from," "comparison window," "identical," "percentage of sequence identity," "substantially identical," "complementary," and "substantially complementary."

For sequence comparison of nucleic acid sequences, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters are used. Methods of alignment of sequences for comparison are well known in the art. Optimal alignment of sequences for comparison can be conducted, e.g., by the local homology algorithm of Smith and Waterman, Adv. Appl. Math. 2:482, 1981, by the homology alignment algorithm of Needleman and Wunsch, J. Mol. Biol. 48:443, 1970, by the search for similarity method of Pearson & Lipman, Proc. Nat'l. Acad. Sci. USA 85:2444, 1988, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds 1995 supplement)).

One example of a useful algorithm is PILEUP. PILEUP uses a simplification of the progressive alignment method of Feng & Doolittle, J. Mol. Evol. 35:351-360, 1987. The method used is similar to the method described by Higgins & Sharp, CABIOS 5:151-153, 1989. Using PILEUP, a reference sequence is compared to other test sequences to determine the percent sequence identity relationship using the following parameters: default gap weight (3.00), default gap length weight (0.10), and weighted end gaps. PILEUP can be obtained from the GCG sequence analysis software package, e.g., version 7.0 (Devereaux et al., Nuc. Acids Res. 12:387-395, 1984.

Another example of algorithms that are suitable for determining percent sequence identity and sequence similarity are the BLAST and the BLAST 2.0 algorithm, which are described in Altschul et al., J. Mol. Biol. 215:403-410, 1990 and Altschul et al., Nucleic Acids Res. 25:3389-3402, 1977. Software for performing BLAST analyses is publicly available through the National Center for Biotechnology Information (ncbi.nlm.nih.gov). The BLASTN program (for nucleotide sequences) uses as defaults a word length (W) of 11, alignments (B) of 50, expectation (E) of 10, M=5, N=−4, and a comparison of both strands. The BLASTP program (for amino acid sequences) uses as defaults a word length (W) of 3, and expectation (E) of 10, and the BLOSUM62 scoring matrix (see Henikoff & Henikoff, Proc. Natl. Acad. Sci. USA 89:10915, 1989). An oligonucleotide is a linear polynucleotide sequence of up to about 100 nucleotide bases in length.

ClustalW is a program that aligns three or more sequences in a computationally efficient manner. Aligning multiple sequences highlights areas of similarity which may be associated with specific features that have been more highly conserved than other regions. Thus, this program can classify sequences for phylogenetic analysis, which aims to model the substitutions that have occurred over evolution and derive the evolutionary relationships between sequences. The ClustalW multiple sequence alignment web form is available on the internet from EMBL-EBI (ebi.ac.uk/Tools/msa/clustalw2/), see also Larkin et al., Bioinformatics 23(21): 2947-2948, 2007.

A polynucleotide or nucleic acid sequence refers to a polymeric form of nucleotide at least 10 bases in length. A recombinant polynucleotide includes a polynucleotide that is not immediately contiguous with both of the coding sequences with which it is immediately contiguous (one on the 5' end and one on the 3' end) in the naturally occurring genome of the organism from which it is derived. The term therefore includes, for example, a recombinant DNA which is incorporated into a vector; into an autonomously replicating plasmid or virus; or into the genomic DNA of a prokaryote or eukaryote, or which exists as a separate molecule (e.g., a cDNA) independent of other sequences. The nucleotides can be ribonucleotides, deoxyribonucleotides, or modified forms of either nucleotide. The term includes single- and double-stranded forms of DNA.

Pharmaceutically acceptable carriers: The pharmaceutically acceptable carriers of use are conventional. Remington's Pharmaceutical Sciences, by E. W. Martin, Mack Publishing Co., Easton, Pa., 19th Edition, 1995, describes compositions and formulations suitable for pharmaceutical delivery of the antibodies herein disclosed.

In general, the nature of the carrier will depend on the particular mode of administration being employed. For instance, parenteral formulations usually comprise injectable fluids that include pharmaceutically and physiologically acceptable fluids, which include, but are not limited to, water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Pharmaceutical agent: A chemical compound or composition capable of inducing a desired therapeutic or prophylactic effect when properly administered to a subject or a cell. In some examples a pharmaceutical agent includes one or more of the disclosed antibodies.

Polypeptide: Any chain of amino acids, regardless of length or post-translational modification (e.g., glycosylation or phosphorylation). In one embodiment, the polypeptide is NoV polypeptide, such as a capsid polypeptide. In one embodiment, the polypeptide is a disclosed antibody or a fragment thereof. A "residue" refers to an amino acid or amino acid mimetic incorporated in a polypeptide by an amide bond or amide bond mimetic. A polypeptide has an amino terminal (N-terminal) end and a carboxy terminal end. Conservative amino acid substitution tables providing functionally similar amino acids are well known to one of ordinary skill in the art. The following six groups are examples of amino acids that are considered to be conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

Purified: The term purified does not require absolute purity; rather, it is intended as a relative term. Thus, for example, a purified peptide preparation is one in which the peptide or protein (such as an antibody) is more enriched than the peptide or protein is in its natural environment within a cell. In one embodiment, a preparation is purified such that the protein or peptide represents at least 50%, 60%, 70%, 80%, 90%, 95%, 96%, 97%, 98%, or 99% of the total peptide or protein content of the preparation.

Recombinant: A recombinant nucleic acid is one that has a sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, e.g., by genetic engineering techniques.

Sequence identity: The similarity between amino acid sequences is expressed in terms of the similarity between the sequences, otherwise referred to as sequence identity. Sequence identity is frequently measured in terms of percentage identity (or similarity or homology); the higher the percentage, the more similar the two sequences are. Homologs or variants of a polypeptide will possess a relatively high degree of sequence identity when aligned using standard methods.

Methods of alignment of polypeptide sequences for comparison are well known in the art. Various programs and alignment algorithms are described in: Smith and Waterman, Adv. Appl. Math. 2:482, 1981; Needleman and Wunsch, J. Mol. Biol. 48:443, 1970; Pearson and Lipman, Proc. Natl. Acad. Sci. U.S.A. 85:2444, 1988; Higgins and Sharp, Gene 73:237, 1988; Higgins and Sharp, CABIOS 5:151, 1989; Corpet et al., Nucleic Acids Research 16:10881, 1988; and Pearson and Lipman, Proc. Natl. Acad. Sci. U.S.A. 85:2444, 1988. Altschul et al., Nature Genet. 6:119, 1994, presents a detailed consideration of sequence alignment methods and homology calculations. The NCBI Basic Local Alignment Search Tool (BLAST) (Altschul et al., J. Mol. Biol. 215:403, 1990) is available from several sources, including the National Center for Biotechnology Information (NCBI, Bethesda, Md.) and on the internet (along with a description of how to determine sequence identity using this program).

Homologs and variants of a $V_L$ or a $V_H$ of an antibody, or a $V_HH$ monoclonal antibody, that specifically binds a polypeptide are typically characterized by possession of at least about 75%, for example at least about 80%, 85%, 90%, 91%, 92%, 93%, 94%, 95%, 96%, 97%, 98% or 99% sequence identity counted over the full length alignment with the amino acid sequence of interest. Proteins with even greater similarity to the reference sequences will show increasing percentage identities when assessed by this method, such as at least 80%, at least 85%, at least 90%, at least 95%, at least 98%, or at least 99% sequence identity. When less than the entire sequence is being compared for sequence identity, homologs and variants will typically possess at least 80% sequence identity over short windows of 10-20 amino acids, and may possess sequence identities of at least 85% or at least 90% or 95% depending on their similarity to the reference sequence. One of skill in the art will appreciate that these sequence identity ranges are provided for guidance only; it is entirely possible that strongly significant homologs could be obtained that fall outside of the ranges provided.

Nucleic acids that "selectively hybridize" or "selectively bind" do so under moderately or highly stringent conditions that excludes non-related nucleotide sequences. In nucleic acid hybridization reactions, the conditions used to achieve a particular level of stringency will vary, depending on the nature of the nucleic acids being hybridized. For example, the length, degree of complementarity, nucleotide sequence composition (for example, GC v. AT content), and nucleic acid type (for example, RNA versus DNA) of the hybridizing regions of the nucleic acids can be considered in selecting hybridization conditions. An additional consideration is whether one of the nucleic acids is immobilized, for example, on a filter.

A specific example of progressively higher stringency conditions is as follows: 2×SSC/0.1% SDS at about room temperature (hybridization conditions); 0.2×SSC/0.1% SDS at about room temperature (low stringency conditions); 0.2×SSC/0.1% SDS at about 42° C. (moderate stringency conditions); and 0.1×SSC at about 68° C. (high stringency conditions). One of skill in the art can readily determine variations on these conditions (e.g., Molecular Cloning: A Laboratory Manual, 2nd ed., vol. 1-3, ed. Sambrook et al., Cold Spring Harbor Laboratory Press, Cold Spring Harbor, N.Y., 1989). Washing can be carried out using only one of these conditions, e.g., high stringency conditions, or each of the conditions can be used, e.g., for 10-15 minutes each, in the order listed above, repeating any or all of the steps listed. However, as mentioned above, optimal conditions will vary, depending on the particular hybridization reaction involved, and can be determined empirically.

Specifically bind: When referring to an antibody, refers to a binding reaction which determines the presence of a target protein, peptide, or polysaccharide in the presence of a heterogeneous population of proteins and other biologics. Thus, under designated conditions, an antibody binds preferentially to a particular target protein, peptide or polysaccharide (such as an antigen present on the surface of a pathogen, for example VP1 or any other NoV polypeptide) and do not bind in a significant amount to other proteins or polysaccharides present in the sample or subject. Specific binding can be determined by methods known in the art. With reference to an antibody antigen complex, specific binding of the antigen and antibody has a $K_d$ of less than about $10^{-7}$ Molar, such as less than about $10^{-7}$ Molar, $10^{-8}$ Molar, $10^{-9}$, or even less than about $10^{-10}$ Molar for a primate antibody. The antigen specificity and affinity of $V_HH$ from immune libraries Kinetickon and koff rate constants in the ranges of $10^5$ to $10^6$ $M^{-1}s^{-1}$ and $10^{-2}$ to $10^{-4}$ $s^{-1}$, respectively, are routinely obtained so that low nanomolar or even picomolar equilibrium dissociation constants are obtained. Such affinity parameters are excellent for most applications (Muyldermans, Annu. Rev. Biochem. 2013. 82:775-97, 2013).

Therapeutic agent: Used in a generic sense, it includes treating agents, prophylactic agents, and replacement agents.

Therapeutically effective amount or effective amount: A quantity of a specific substance, such as a disclosed antibody, sufficient to achieve a desired effect in a subject being treated. For instance, this can be the amount necessary to inhibit NoV replication or NV replication, or to treat an infection with the virus. In several embodiments, a therapeutically effective amount is the amount necessary to reduce a sign or symptom of the infection, and/or to decrease viral titer in a subject. When administered to a subject, a dosage will generally be used that will achieve target tissue concentrations that has been shown to achieve a desired in vitro effect.

Vector: A nucleic acid molecule as introduced into a host cell, thereby producing a transformed host cell. A vector may include nucleic acid sequences that permit it to replicate in a host cell, such as an origin of replication. A vector may also include one or more selectable marker genes and other genetic elements known in the art.

$V_HH$: The variable domain of a camelid heavy chain antibody is called $V_HH$, and is comprised of only one polypeptide chain. A naturally occurring $V_HH$ has a molecular weight of approximately 15 kDa. There is no Fc region in a $V_HH$. DNA encoding a $V_HH$ can be modified by genetic engineering to yield a small recombinant protein having high affinity for a target, resulting in a low molecular weight antibody-derived protein known as a camelid "nanoantibody" or "nanobody". See U.S. Pat. No. 5,759,808 issued Jun. 2, 1998; see also Stijlemans et al., J Biol Chem 279: 1256-1261, 2004; Dumoulin et al., Nature 424: 783-788, 2003; Pleschberger et al., Bioconjugate Chem 14: 440-448, 2003; Cortez-Retamozo et al. Int J Cancer 89: 456-62, 2002; and Lauwereys et al., EMBO J 17: 3512-3520, 1998.

A $V_HH$ includes in an N- to C-direction, the following structural domains: N-FR1-CDR1-FR2-CDR2-FR3-CDR3-FR4-C, wherein FR denotes a framework region amino acid sequence and CDR denotes a complementary determining region amino acid sequence (see, e.g., Kabat et al., Sequences of Proteins of Immunological Interest, U.S. Department of Health and Human Services, 1991). In specific non-limiting examples, the CDR3 comprises a llama CDR3 $V_HH$ domain amino acid sequence; and wherein the antibody binds to Norovirus (NoV). $V_HH$ monoclonal antibodies have only a heavy chain, and thus include only one CDR1, CDR2 and CDR3. Generally, the CDR3 is primarily responsible for antigen specificity.

Virus: Microscopic infectious organism that reproduces inside living cells. A virus consists essentially of a core of a single nucleic acid surrounded by a protein coat, and has the ability to replicate only inside a living cell. "Viral replication" is the production of additional virus by the occurrence of at least one viral life cycle. A virus may subvert the host cells' normal functions, causing the cell to behave in a manner determined by the virus. For example, a viral infection may result in a cell producing a cytokine, or responding to a cytokine, when the uninfected cell does not normally do so.

The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below. The term "comprises" means "includes." All publications, patent applications, patents, and other references mentioned herein are incorporated by reference in their entirety. In case of conflict, the present specification, including explanations of terms, will control. In addition, the materials, methods, and examples are illustrative only and not intended to be limiting.

$V_HH$ Monoclonal Antibodies that Specifically Bind NoV

Isolated single domain monoclonal antibodies, $V_HH$, and antigen binding fragments thereof that specifically bind a NoV polypeptide, and specifically bind a NoV, are disclosed herein. In some embodiments, the antibody specifically binds a NoV Genogroup I or a NoV Genogroup II recombinant virus like particles (VLPs). In some embodiments, the antibody specifically binds a Norwalk virus VLP or a MD2004 virus VLP. The antibody can specifically bind a viral structural capsid protein (VP) 1. In some examples, the monoclonal antibody specifically binds a P1 or P2 subdomain of VP1. The monoclonal antibody can specifically bind the NoV polypeptide and/or VLPs.

In some embodiments the monoclonal antibodies or antigen binding fragment thereof specifically bind a NoV VPLs with an equilibrium constant ($K_d$) of 1 nM or less. In several embodiments, the antibodies and antigen binding fragments bind the NoV polypeptide, such as a Norwalk virus polypeptide or an MD2004 virus polypeptide, with a binding affinity of $1 \times 10^{-9}$ M, at least about $1.5 \times 10^{-9}$M, at least about $2 \times 10^{-9}$M, at least about $3 \times 10^{-9}$M, at least about $3 \times 10^{-9}$ M, at least about $5 \times 10^{-9}$M, at least about $6 \times 10^{-9}$M, at least about $7 \times 10^{-9}$M, at least about $8 \times 10^{-9}$M, at least about $9 \times 10^{-9}$M, or at least about $1 \times 10^{-10}$ M.

In some embodiments, the antibody is neutralizing. In further embodiments the antibody is broadly neutralizing, such as for all or many Genogroup I or Genogroup II NoV. In other embodiments, the antibody inhibits the binding of NoV VLPs to HBGA synthetic carbohydrates, for example H1 or H3 type HBGA, in a dose dependent manner. In other embodiments the antibody inhibits the binding of NoV-VLPs to pig gastric mucin or saliva, in a dose dependent manner. In additional embodiments, the antibody is inhibitory in a hemagglutination assay.

The monoclonal antibody can be of any isotype. The single domain monoclonal antibody can be, for example, an IgG antibody. The class of an antibody can be switched with another. In one aspect, a nucleic acid molecule encoding the $V_HH$ is isolated using methods well-known in the art, such that it does not include any nucleic acid sequences encoding the constant region. The nucleic acid molecule encoding the $V_HH$ can be operatively linked to a nucleic acid sequence encoding a $C_H$ from a different class of immunoglobulin molecule. This can be achieved using a vector or nucleic acid molecule that comprises a $C_H$ chain, as known in the art. For example, an antibody can be class switched to an IgG. Class switching can be used to convert one IgG subclass to another, such as, but not limited to, from $IgG_1$ to $IgG_2$ or $IgG_3$.

The monoclonal antibodies disclosed herein can be llama antibodies, and can include a llama framework region. In some embodiments, the antibodies are humanized, and thus include one or more human framework regions. Exemplary framework regions are disclosed, for example, in PCT Publication No. WO 2011/038290 and Published U.S. Patent Application No. 2012/0244166A1, which are incorporated by reference herein. In some embodiments, the antibodies disclosed herein are chimeric antibodies. In some embodiments, the antibodies include llama and human regions.

In some embodiments, the monoclonal antibody includes only a heavy chain variable ($V_HH$) domain, in the absence of a light chain domain. Each VH is composed of three CDRs and four FWRs, arranged from amino-terminus to carboxy-terminus in the following order: FWR1, CDR1, FWR2, CDR2, FWR3, CDR3, and FWR4. In humans, the heavy chain constant region is comprised of three domains, $CH_1$, $CH_2$ and $CH_3$, while llamas do not have a $CH_1$ domain.

CDRs and FWRs may be defined according to Kabat (Sequences of Proteins of Immunological Interest (National Institutes of Health, Bethesda, Md., 1987 and 1991) Amino acid numbering of antibodies or antigen binding fragments is also according to that of Kabat. Each CDR can include amino acid residues from a complementarity determining region as defined by Kabat (i.e. about residues 31-35 (CDR-H1), 50-65 (CDR-H2) and 95-102 (CDR-H3) in the heavy chain variable domain (SEQ ID NO:2). However, in some antibodies the CDRs include those residues from a hypervariable loop (i.e. about residues 26-32 (CDR-H1), 53-55 (CDR-H2) and 96-101 (CDR-H3) in the heavy chain variable domain (SEQ ID NO:2); Chothia and Lesk J. Mol. Biol. 196:901-917 (1987)). In some instances, a complementarity determining region can include amino acids from both a CDR region defined according to Kabat and a hypervariable loop. In a wild type antibody, each variable domain typically has four FWRs identified as FWR1, FWR2, FWR3 and FWR4. If the CDRs are defined according to Kabat, the heavy chain FWR residues are positioned about at residues 1-30 (HCFR1), 36-49 (HCFR2), 66-94 (HCFR3), and 103-113 (HCFR4) of SEQ ID NO:2. If the CDRs comprise amino acid residues from hypervariable loops, the heavy chain FWR residues are positioned about at residues 1-25 (HCFR1), 33-52 (HCFR2), 56-95 (HCFR3), and 102-113 (HCFR4) in the heavy chain (SEQ ID NO:2). In some instances, when the CDR comprises amino acids from both a CDR as defined by Kabat and those of a hypervariable loop, the FWR residues are adjusted accordingly.

Figure 8:
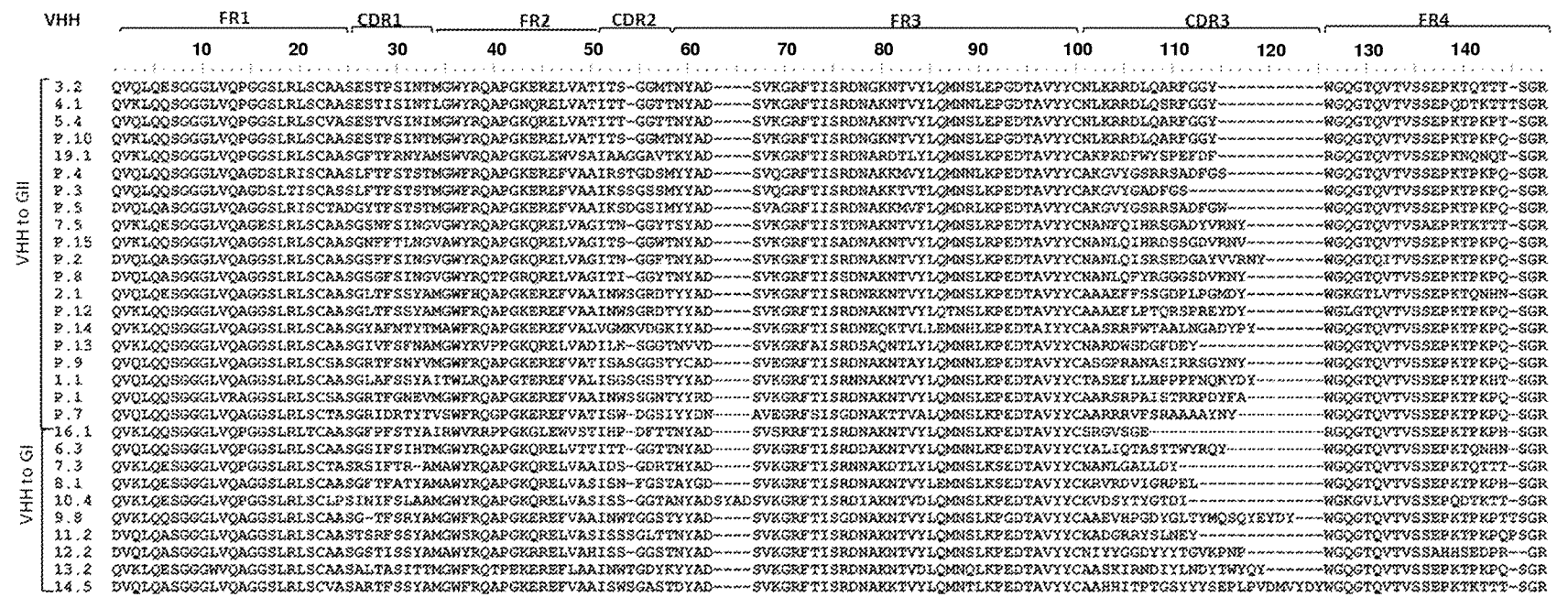

Thus, in some embodiments, the monoclonal antibody includes one or more heavy chain CDRs from the variable domains shown in FIG. 8, as defined by the Kabat, Chothia or IMGT numbering system.

The monoclonal antibodies disclosed herein can specifically bind NoV VLPs, such as a Genogroup I or Genogroup II NoV VLPs. NoVs are nonenveloped ~38 nm icosahedral viruses with an approximately 7.5 kb single-stranded, positive-sense RNA genome that encodes three open reading frames (ORFs). ORF1 encodes RNA-dependent RNA polymerase, while ORFs 2 and 3 encode the major (VP1) and minor (VP2) capsid proteins, respectively. The VP1 is structurally divided into the shell domain (S) that forms the internal structural core of the particle and the protruding domain (P) that is exposed on the outer surface (Prasad et al., Science 286:287-90, 1999). The P domain is further subdivided into the P1 subdomain (residues 226 to 278 and 406 to 520) and the P2 subdomain (residues 279 to 405) (Prasad et al., J Virol 68:5117-25, 1999). P2 represents the most exposed surface of the viral particle and is involved in interactions with both neutralizing antibodies and HBGA oligosaccharides (Cao et al., J Virol 81:5949-57, 2007; Chen et al., Proc Natl Acad Sci USA 103:8048-53, 2006; Lochridge et al., J Gen Virol 86:2799-806, 2005).

NoVs are divided into five distinct genogroups (GI-GV) based on VP1 sequence similarity. Different types within each Genogroup are separated from the Genogrop by a decimal point. Virus strains from GI and GII are responsible for most human infections, and these genogroups are further subdivided into more than 30 different genotypes (Kroneman et al., Arch Virol 158(10): 2059-68, 2013.). Although human NoV GII.4 strains are now recognized as the predominant genotype, the GI.1 Norwalk virus (NV) has been studied most extensively because of its historical precedence (Kapikian J Infect Dis 181 Suppl 2:S295-302, 2000). Early human challenge studies with NV provided evidence for short-term, but not long-term (>2 years), homologous immunity following infection with NV and showed also the absence of heterotypic immunity when cross-challenged with the GII.1 Hawaii virus (Wyatt et al., J Infect Dis 129:709-14, 1974). Later human challenge studies showed an association between HBGA secretor status and susceptibility to NV infection (Harrington et al., J Virol 76:12335-43, 2002; Hutson et al., J Infect Dis 185:1335-7, 2002; Lindesmith et al., Nat Med 9(5):548-53, 2003; Marionneau et al., Gastroenterology 122:1967-77, 2002). The elucidation of human NoV virion structure is based largely on the X-ray crystallographic analysis of NoV rVLPs (Prasad et al., Science 286:287-90, 1999; Prasad et al., J Virol 68:5117-25, 1994); these VLPs are a promising NoV vaccine candidate (Atmar et al., N Engl J Med 365:2178-87, 2011).

Examples of NoVs include, but are not limited to, NV (NV, see, for example, GENBANK® Accession No. M87661, NP_056821), P7-587 virus (see, for example, GENBANK® Accession No. FJ384783), Southampton virus (SHV, see, for example, GENBANK® Accession No. L07418), Desert Shield virus (DSV, see, for example, GENBANK® Accession No. U04469), Hesse virus (HSV, see, for example, GENBANK® Accession No. AF093797), Chiba virus (CHV, see, for example, GENBANK® Accession No. AB042808), Hawaii virus (HV, see, for example, GENBANK® Accession No. U07611), Snow Mountain virus (SMV, see, for example, GENBANK® Accession No. U70059), Toronto virus (TV, see for example, GENBANK® Accession No. UO2030), Bristol virus (BV, see for example, GENBANK® Accession No. X76716), Jena virus (JV, see, for example, GENBANK® Accession No. AJ011099), MD145-12 virus (MD145-12, see, for example, GENBANK® Accession No. AY032605), Aichi virus (AV124-89, see, for example, GENBANK® Accession No. AB031013), Camberwell (CV, see, for example, GENBANK® Accession No. AF145896), Lordsdale virus (LV, see, for example, GENBANK® Accession No. X86557), Grimsby virus (GrV, see, for example, GENBANK® Accession No. AJ004864), Mexico virus (MXV, see, for example, GENBANK® Accession No. U22498), Boxer (see, for example, GENBANK® Accession No. AF538679), C59 (see, for example, GENBANK® Accession No. AF435807), VA98115 (see, for example, GENBANK® Accession No. AY038598), BUDS (see, for example, GENBANK® Accession No. AY660568), MOH (see, for example, GENBANK® Accession No. AF397156), Parris Island (PiV; see, for example, GENBANK® Accession No. AY652979), VA98387 (see, for example, GENBANK® Accession No. AY038600), VA97207 (see, for example, GENBANK® Accession No. AY038599), and Operation Iraqi Freedom (see, for example, 01F, GENBANK® Accession No. AY675554).

In some embodiments, the monoclonal antibody specifically binds a Genogroup I NoVs, which include, but are not limited to, Norwalk virus. In additional embodiments, the antibody specifically binds Genogroup II NoVs, which include, but are not limited to, MD2004 virus.

In some embodiments, the monoclonal antibody, or antigen binding fragment thereof specifically binds a Genogroup II NoV polypeptide, and includes a CDR3, wherein the CDR3 includes the amino acid sequence set forth as one of:
  a) amino acids 96-109 of SEQ ID NO: 1;
  b) amino acids 96-109 of SEQ ID NO: 2;
  c) amino acids 96-109 of SEQ ID NO: 3;
  d) amino acids 96-109 of SEQ ID NO: 4;
  e) amino acids 97-110 of SEQ ID NO: 5;
  f) amino acids 97-111 of SEQ ID NO: 6;
  g) amino acids 97-111 of SEQ ID NO: 7;
  h) amino acids 97-111 of SEQ ID NO: 8;
  i) amino acids 96-112 of SEQ ID NO: 9;
  j) amino acids 96-112 of SEQ ID NO: 10;
  k) amino acids 96-114 of SEQ ID NO: 11;
  l) amino acids 96-112 of SEQ ID NO: 12;
  m) amino acids 97-113 of SEQ ID NO: 13;
  n) amino acids 97-113 of SEQ ID NO: 14;
  o) amino acids 97-114 of SEQ ID NO: 15;
  p) amino acids 96-107 of SEQ ID NO: 16;
  q) amino acids 97-113 of SEQ ID NO: 17;
  r) amino acids 97-114 of SEQ ID NO: 18;
  s) amino acids 97-113 of SEQ ID NO: 19;
  t) amino acids 96-111 of SEQ ID NO: 20; or
  u) amino acids 96-102 of SEQ ID NO: 21.

The monoclonal antibody can be a $V_H H$ monoclonal antibody.

In other embodiments, the monoclonal antibody, or antigen binding fragment thereof, specifically binds a Genogroup I NoV polypeptide, and includes a CDR3, wherein the CDR3 includes the amino acid sequence set forth as one of:
  a) amino acids 96-110 of SEQ ID NO: 22;
  b) amino acids 95-104 of SEQ ID NO: 23;
  c) amino acids 96-107 of SEQ ID NO: 24;
  d) amino acids 100-110 of SEQ ID NO: 25;
  e) amino acids 96-117 of SEQ ID NO: 26;
  f) amino acids 97-108 of SEQ ID NO: 27;
  g) amino acids 96-112 of SEQ ID NO: 28;
  h) amino acids 97-115 of SEQ ID NO: 29; or
  i) amino acids 97-121 of SEQ ID NO: 30.

The monoclonal antibody can be a $V_H H$ monoclonal antibody.

In some embodiments, the monoclonal antibody, or antigen binding fragment thereof, specifically binds a Genogroup II NoV polypeptide, and includes:
  a) a CDR1 comprising amino acids 26-33 of SEQ ID NO: 1, a CDR2 comprising amino acids 51-57 of SEQ ID NO: 1, and/or a CDR3 comprising amino acids 96-109 of SEQ ID NO: 1;
  b) a CDR1 comprising amino acids 26-33 of SEQ ID NO: 2, a CDR2 comprising amino acids 51-57 of SEQ ID NO: 2, and/or a CDR3 comprising amino acids 96-109 of SEQ ID NO: 2;
  c) a CDR1 comprising amino acids 26-33 of SEQ ID NO: 3, a CDR2 comprising amino acids 51-57 of SEQ ID NO: 3, and/or a CDR3 comprising amino acids 96-109 of SEQ ID NO: 3;

d) a CDR1 comprising amino acids 26-33 of SEQ ID NO: 4, a CDR2 comprising amino acids 51-57 of SEQ ID NO: 4, and/or a CDR3 comprising amino acids 96-109 of SEQ ID NO: 4;
e) a CDR1 comprising amino acids 26-33 of SEQ ID NO: 5, a CDR2 comprising amino acids 51-58 of SEQ ID NO: 5, and/or a CDR3 comprising amino acids 97-110 of SEQ ID NO: 5;
f) a CDR1 comprising amino acids 26-33 of SEQ ID NO: 6, a CDR2 comprising amino acids 51-58 of SEQ ID NO: 6, and/or a CDR5 comprising amino acids 97-111 of SEQ ID NO: 6;
g) a CDR1 comprising amino acids 26-33 of SEQ ID NO: 7, a CDR2 comprising amino acids 51-58 of SEQ ID NO: 7, and/or a CDR3 comprising amino acids 97-111 of SEQ ID NO: 7;
h) a CDR1 comprising amino acids 26-33 of SEQ ID NO: 8, a CDR2 comprising amino acids 51-58 of SEQ ID NO: 8, and/or a CDR3 comprising amino acids 97-111 of SEQ ID NO: 8;
i) a CDR1 comprising amino acids 26-33 of SEQ ID NO: 9, a CDR2 comprising amino acids 51-57 of SEQ ID NO: 9, and/or a CDR3 comprising amino acids 96-112 of SEQ ID NO: 9;
j) a CDR1 comprising amino acids 26-33 of SEQ ID NO: 10, a CDR2 comprising amino acids 51-57 of SEQ ID NO: 10, and/or a CDR3 comprising amino acids 96-112 of SEQ ID NO: 10;
k) a CDR1 comprising amino acids 26-33 of SEQ ID NO: 11, a CDR2 comprising amino acids 51-57, and/or a CDR3 comprising amino acids 96-114 of SEQ ID NO: 11;
l) a CDR1 comprising amino acids 26-33 of SEQ ID NO: 12, a CDR2 comprising amino acids 51-57 of SEQ ID NO: 12, and/or a CDR3 comprising amino acids 96-112 of SEQ ID NO: 12;
m) a CDR1 comprising amino acids 26-33 of SEQ ID NO: 13, a CDR2 comprising amino acids 51-58 of SEQ ID NO: 13, and/or a CDR3 comprising amino acids 97-113 of SEQ ID NO: 13;
n) a CDR1 comprising amino acids 26-33 of SEQ ID NO: 14, a CDR2 comprising amino acids 51-58 of SEQ ID NO: 14, and/or a CDR3 comprising amino acids 97-113 of SEQ ID NO: 14;
o) a CDR1 comprising amino acids 26-33 of SEQ ID NO: 15, a CDR2 comprising amino acids 51-58 of SEQ ID NO: 15, and/or a CDR3 comprising amino acids 97-114 of SEQ ID NO: 15;
p) a CDR1 comprising amino acids 26-33 of SEQ ID NO: 16, a CDR2 comprising amino acids 51-57 of SEQ ID NO: 16, and/or a CDR3 comprising amino acids 96-107 of SEQ ID NO: 16;
q) a CDR1 comprising amino acids 26-33 of SEQ ID NO: 17, a CDR2 comprising amino acids 51-58 of SEQ ID NO: 17, and/or a CDR3 comprising amino acids 97-113 of SEQ ID NO: 17;
r) a CDR1 comprising amino acids 26-33 of SEQ ID NO: 18, a CDR2 comprising amino acids 51-58 of SEQ ID NO: 18, and/or a CDR3 comprising amino acids 97-114 of SEQ ID NO: 18;
s) a CDR1 comprising amino acids 26-33 of SEQ ID NO: 19, a CDR2 comprising amino acids 51-58 of SEQ ID NO: 19, and/or a CDR3 comprising amino acids 97-113 of SEQ ID NO: 19;
t) a CDR1 comprising amino acids 26-33 of SEQ ID NO: 20, a CDR2 comprising amino acids 51-57 of SEQ ID NO:20, and/or a CDR3 comprising amino acids 96-111 of SEQ ID NO: 20; or
u) a CDR1 comprising amino acids 26-33 of SEQ ID NO: 21, a CDR2 comprising amino acids 51-57 of SEQ ID NO:21, and/or a CDR3 comprising amino acids 96-102 of SEQ ID NO: 21.

The monoclonal antibody can be a $V_HH$ monoclonal antibody.

In other embodiments, the monoclonal antibody, or antigen binding fragment thereof, specifically binds a Genogroup II NoV polypeptide, and includes:
a) a CDR1 comprising amino acids 26-33 of SEQ ID NO: 22, a CDR2 comprising amino acids 51-57 of SEQ ID NO:22, and/or a CDR3 comprising amino acids 96-110 of SEQ ID NO: 22;
b) a CDR1 comprising amino acids 26-33 of SEQ ID NO: 23, a CDR2 comprising amino acids 50-56 of SEQ ID NO:23, and/or a CDR3 comprising amino acids 95-104 of SEQ ID NO: 23;
c) a CDR1 comprising amino acids 26-33 of SEQ ID NO: 24, a CDR2 comprising amino acids 51-57 of SEQ ID NO:24, and/or a CDR3 comprising amino acids 96-107 of SEQ ID NO: 24;
d) a CDR1 comprising amino acids 26-33 of SEQ ID NO: 25, a CDR2 comprising amino acids 51-57 of SEQ ID NO: 25, and/or a CDR3 comprising amino acids 100-110 of SEQ ID NO: 25;
e) a CDR1 comprising amino acids 26-33 of SEQ ID NO: 26, a CDR2 comprising amino acids 50-57 of SEQ ID NO:26, and/or a CDR3 comprising amino acids 96-117 of SEQ ID NO: 26;
f) a CDR1 comprising amino acids 26-33 of SEQ ID NO: 27, a CDR2 comprising amino acids 51-58 of SEQ ID NO:27, and/or a CDR3 comprising amino acids 97-108 of SEQ ID NO: 27;
g) a CDR1 comprising amino acids 26-33 of SEQ ID NO: 28, a CDR2 comprising amino acids 51-57 of SEQ ID NO:28, and/or a CDR3 comprising amino acids 96-112 of SEQ ID NO: 28;
h) a CDR1 comprising amino acids 26-33 of SEQ ID NO: 29, a CDR2 comprising amino acids 51-58 of SEQ ID NO:29, and/or a CDR3 comprising amino acids 97-115 of SEQ ID NO: 29; or
i) a CDR1 comprising amino acids 26-33 of SEQ ID NO: 30, a CDR2 comprising amino acids 51-58 of SEQ ID NO:30, and/or a CDR3 comprising amino acids 97-121 of SEQ ID NO: 30.

The monoclonal antibody can be a $V_HH$ monoclonal antibody.

In additional embodiments, the monoclonal antibody, or antigen binding fragment thereof, specifically binds a Genogroup II NoV, and includes:
a) a CDR1 comprising amino acids 26-33 of SEQ ID NO: 1, a CDR2 comprising amino acids 51-57 of SEQ ID NO: 1, and a CDR3 comprising amino acids 96-109 of SEQ ID NO: 1;
b) a CDR1 comprising amino acids 26-33 of SEQ ID NO: 2, a CDR2 comprising amino acids 51-57 of SEQ ID NO: 2, and a CDR3 comprising amino acids 96-109 of SEQ ID NO: 2;
c) a CDR1 comprising amino acids 26-33 of SEQ ID NO: 3, a CDR2 comprising amino acids 51-57 of SEQ ID NO: 3, and a CDR3 comprising amino acids 96-109 of SEQ ID NO: 3;

d) a CDR1 comprising amino acids 26-33 of SEQ ID NO: 4, a CDR2 comprising amino acids 51-57 of SEQ ID NO: 4, and a CDR3 comprising amino acids 96-109 of SEQ ID NO: 4;

e) a CDR1 comprising amino acids 26-33 of SEQ ID NO: 5, a CDR2 comprising amino acids 51-58 of SEQ ID NO: 5, and a CDR3 comprising amino acids 97-110 of SEQ ID NO: 5;

f) a CDR1 comprising amino acids 26-33 of SEQ ID NO: 6, a CDR2 comprising amino acids 51-58 of SEQ ID NO: 6, and a CDR5 comprising amino acids 97-111 of SEQ ID NO: 6;

g) a CDR1 comprising amino acids 26-33 of SEQ ID NO: 7, a CDR2 comprising amino acids 51-58 of SEQ ID NO: 7, and a CDR3 comprising amino acids 97-111 of SEQ ID NO: 7;

h) a CDR1 comprising amino acids 26-33 of SEQ ID NO: 8, a CDR2 comprising amino acids 51-58 of SEQ ID NO: 8, and a CDR3 comprising amino acids 97-111 of SEQ ID NO: 8;

i) a CDR1 comprising amino acids 26-33 of SEQ ID NO: 9, a CDR2 comprising amino acids 51-57 of SEQ ID NO: 9, and a CDR3 comprising amino acids 96-112 of SEQ ID NO: 9;

j) a CDR1 comprising amino acids 26-33 of SEQ ID NO: 10, a CDR2 comprising amino acids 51-57 of SEQ ID NO: 10, and a CDR3 comprising amino acids 96-112 of SEQ ID NO: 10;

k) a CDR1 comprising amino acids 26-33 of SEQ ID NO: 11, a CDR2 comprising amino acids 51-57, and a CDR3 comprising amino acids 96-114 of SEQ ID NO: 11;

l) a CDR1 comprising amino acids 26-33 of SEQ ID NO: 12, a CDR2 comprising amino acids 51-57 of SEQ ID NO: 12, and a CDR3 comprising amino acids 96-112 of SEQ ID NO: 12;

m) a CDR1 comprising amino acids 26-33 of SEQ ID NO: 13, a CDR2 comprising amino acids 51-58 of SEQ ID NO: 13, and a CDR3 comprising amino acids 97-113 of SEQ ID NO: 13;

n) a CDR1 comprising amino acids 26-33 of SEQ ID NO: 14, a CDR2 comprising amino acids 51-58 of SEQ ID NO: 14, and a CDR3 comprising amino acids 97-113 of SEQ ID NO: 14;

o) a CDR1 comprising amino acids 26-33 of SEQ ID NO: 15, a CDR2 comprising amino acids 51-58 of SEQ ID NO: 15, and a CDR3 comprising amino acids 97-114 of SEQ ID NO: 15;

p) a CDR1 comprising amino acids 26-33 of SEQ ID NO: 16, a CDR2 comprising amino acids 51-57 of SEQ ID NO: 16, and a CDR3 comprising amino acids 96-107 of SEQ ID NO: 16;

q) a CDR1 comprising amino acids 26-33 of SEQ ID NO: 17, a CDR2 comprising amino acids 51-58 of SEQ ID NO: 17, and a CDR3 comprising amino acids 97-113 of SEQ ID NO: 17;

r) a CDR1 comprising amino acids 26-33 of SEQ ID NO: 18, a CDR2 comprising amino acids 51-58 of SEQ ID NO: 18, and a CDR3 comprising amino acids 97-114 of SEQ ID NO: 18;

s) a CDR1 comprising amino acids 26-33 of SEQ ID NO: 19, a CDR2 comprising amino acids 51-58 of SEQ ID NO: 19, and a CDR3 comprising amino acids 97-113 of SEQ ID NO: 19;

t) a CDR1 comprising amino acids 26-33 of SEQ ID NO: 20, a CDR2 comprising amino acids 51-57 of SEQ ID NO:20, and a CDR3 comprising amino acids 96-111 of SEQ ID NO: 20; or u) a CDR1 comprising amino acids 26-33 of SEQ ID NO: 21, a CDR2 comprising amino acids 51-57 of SEQ ID NO:21, and a CDR3 comprising amino acids 96-102 of SEQ ID NO: 21.

The monoclonal antibody can be a $V_HH$ monoclonal antibody.

In yet other embodiments, the monoclonal antibody, or antigen binding fragment thereof, specifically binds a Genogroup I NoV polypeptide, and includes:

a) a CDR1 comprising amino acids 26-33 of SEQ ID NO: 22, a CDR2 comprising amino acids 51-57 of SEQ ID NO:22, and a CDR3 comprising amino acids 96-110 of SEQ ID NO: 22;

b) a CDR1 comprising amino acids 26-33 of SEQ ID NO: 23, a CDR2 comprising amino acids 50-56 of SEQ ID NO:23, and a CDR3 comprising amino acids 95-104 of SEQ ID NO: 23;

c) a CDR1 comprising amino acids 26-33 of SEQ ID NO: 24, a CDR2 comprising amino acids 51-57 of SEQ ID NO:24, and a CDR3 comprising amino acids 96-107 of SEQ ID NO: 24;

d) a CDR1 comprising amino acids 26-33 of SEQ ID NO: 25, a CDR2 comprising amino acids 51-57 of SEQ ID NO: 25, and a CDR3 comprising amino acids 100-110 of SEQ ID NO: 25;

e) a CDR1 comprising amino acids 26-33 of SEQ ID NO: 26, a CDR2 comprising amino acids 50-57 of SEQ ID NO:26, and a CDR3 comprising amino acids 96-117 of SEQ ID NO: 26;

f) a CDR1 comprising amino acids 26-33 of SEQ ID NO: 27, a CDR2 comprising amino acids 51-58 of SEQ ID NO:27, and a CDR3 comprising amino acids 97-108 of SEQ ID NO: 27;

g) a CDR1 comprising amino acids 26-33 of SEQ ID NO: 28, a CDR2 comprising amino acids 51-57 of SEQ ID NO:28, and a CDR3 comprising amino acids 96-112 of SEQ ID NO: 28;

h) a CDR1 comprising amino acids 26-33 of SEQ ID NO: 29, a CDR2 comprising amino acids 51-58 of SEQ ID NO:29, and a CDR3 comprising amino acids 97-115 of SEQ ID NO: 29; or i) a CDR1 comprising amino acids 26-33 of SEQ ID NO: 30, a CDR2 comprising amino acids 51-58 of SEQ ID NO:30, and a CDR3 comprising amino acids 97-121 of SEQ ID NO: 30.

The monoclonal antibody can be a $V_HH$ monoclonal antibody.

In some embodiments, the monoclonal antibody includes a heavy chain variable domain comprising an amino acid sequence at least 90%, 91%, 92%, 93%, 94%, 95%, 96%, 97%, 98% or 99% identical to one of the amino acid sequence set forth as one of SEQ ID NOs: 1-30. Thus, the monoclonal antibody can include a heavy chain variable domain comprising an amino acid sequence at least 90%, 91%, 92%, 93%, 94%, 95%, 96%, 97%, 98% or 99% identical to one of the amino acid sequence set forth as one of SEQ ID NOs: 1-21, and specifically bind a Genogroup II NoV polypeptide. In specific non-limiting examples, the monoclonal antibody can include a heavy chain variable domain comprising an amino acid sequence at least 90%, 91%, 92%, 93%, 94%, 95%, 96%, 97%, 98% or 99% identical to one of the amino acid sequence set forth as one of SEQ ID NOs: 1-21, and include a CDR3 sequence 100% identical to the CDRs sequence of SEQ ID NOs: 1-21, respectively, and specifically bind a Genogroup II NoV polypeptide. The monoclonal antibody can include a heavy chain variable domain comprising an amino acid sequence at least 90%, 91%, 92%, 93%, 94%, 95%, 96%, 97%, 98% or 99% identical to one of the amino acid sequence set forth as one of SEQ ID NOs: 22-30, and specifically bind a Genogroup I NoV polypeptide. In specific non-limiting examples, the monoclonal antibody can include a heavy chain variable domain comprising an amino acid sequence at least 90%, 91%, 92%, 93%, 94%, 95%, 96%, 97%, 98% or 99% identical to one of the amino acid sequence set forth as one of SEQ ID NOs: 22-30, and include a CDR3 sequence 100% identical to the CDRs sequence of SEQ ID NOs: 22-30, respectively, and specifically bind a Genogroup I NoV polypeptide. These monoclonal antibodies can be $V_HH$ monoclonal antibodies.

In additional embodiments, the heavy chain variable domain includes at most 10, at most 9, at most 8, at most 7, at most 6, at most 5, at most 4, at most 3, at most two or at most one conservative amino acid substitutions in an amino acid sequence set forth as one of SEQ ID NOs: 1-30. In yet other embodiments, the heavy chain variable domain includes at most 10, at most 9, at most 8, at most 7, at most 6, at most 5, at most 4, at most 3, at most two or at most one conservative amino acid substitutions in an amino acid sequence set forth as one of SEQ ID NOs: 1-21, and specifically binds a Genogroup II NoV polypeptide. In further embodiments, the heavy chain variable domain includes at most 10, at most 9, at most 8, at most 7, at most 6, at most 5, at most 4, at most 3, at most two or at most one conservative amino acid substitutions in an amino acid sequence set forth as one of SEQ ID NOs: 22-30, and specifically binds a Genogroup I NoV polypeptide. These monoclonal antibodies can be $V_HH$ monoclonal antibodies.

In yet other embodiments, the monoclonal antibody includes a heavy chain variable domain comprising or consisting of one of the amino acid sequence set forth as one of SEQ ID NOs: 1-30. The monoclonal antibody can include a heavy chain variable domain comprising or consisting of one of the amino acid sequences set forth as one of SEQ ID NOs: 1-21, and specifically bind a Genogroup II NoV polypeptide. The monoclonal antibody can include a heavy chain variable domain comprising or consisting of one of the amino acid sequences set forth as one of SEQ ID NOs: 22-30, and specifically bind a Genogroup I NoV polypeptide. These monoclonal antibodies can be $V_HH$ monoclonal antibodies.

The monoclonal antibodies, including $V_HH$ monoclonal antibodies, or antibody fragments disclosed herein can be derivatized or linked to another molecule (such as another peptide, protein, enzyme, chromogen or antibody). In general, the antibody or portion thereof is derivatized such that the binding to the NoV VLPs, for example a Norwalk virus, such as VP1, is not affected adversely by the derivatization or labeling. For example, the antibody can be functionally linked, for example, by chemical coupling, genetic fusion, noncovalent association or otherwise to one or more other molecular entities, such as another antibody (for example, to form a bispecific antibody or to link it to a diabody), a detection agent, a pharmaceutical agent, and/or a protein or peptide that can mediate associate of the antibody or antibody portion with another molecule (such as a streptavidin core region or a polyhistidine tag).

One type of derivatized antibody is produced by crosslinking two or more antibodies (of the same type or of different types, such as to create bispecific antibodies). Suitable crosslinkers include those that are heterobifunctional, having two distinctly reactive groups separated by an appropriate spacer (such as m-maleimidobenzoyl-N-hydroxysuccinimide ester) or homobifunctional (such as disuccinimidyl suberate). Such linkers are available from Pierce Chemical Company (Rockford, Ill.).

A monoclonal antibody, including $V_HH$ monoclonal antibody, that specifically binds a NoV polypeptide, such as a Genogroup I or Genogroup II NoV polypeptide, for example, a NV polypeptide, can be labeled with a detectable moiety. Useful detection agents include fluorescent compounds, including fluorescein, fluorescein isothiocyanate, rhodamine, 5-dimethylamine-1-napthalenesulfonyl chloride, phycoerythrin, lanthanide phosphors, ALEXA FLUOR® and the like. Bioluminescent markers are also of use, such as luciferase, green fluorescent protein (GFP), or yellow fluorescent protein. An antibody can also be labeled with enzymes that are useful for detection, such as horseradish peroxidase, β-galactosidase, luciferase, alkaline phosphatase, glucose oxidase and the like. When an antibody is labeled with a detectable enzyme, it can be detected by adding additional reagents that the enzyme uses to produce a reaction product that can be discerned. For example, when the agent horseradish peroxidase is present the addition of hydrogen peroxide and diaminobenzidine leads to a colored reaction product, which is visually detectable. An antibody may also be labeled with biotin, and detected through indirect measurement of avidin or streptavidin binding. It should be noted that the avidin itself can be labeled with an enzyme or a fluorescent label.

A monoclonal antibody including $V_HH$ monoclonal antibody, may be labeled with a magnetic agent, such as gadolinium. Antibodies can also be labeled with lanthanides (such as europium and dysprosium), and manganese. Paramagnetic particles such as superparamagnetic iron oxide are also of use as labels. An antibody may also be labeled with a predetermined polypeptide epitopes recognized by a secondary reporter (such as leucine zipper pair sequences, binding sites for secondary antibodies, metal binding domains, epitope tags). In some embodiments, labels are attached by spacer arms of various lengths to reduce potential steric hindrance.

An antibody can also be labeled with a radiolabeled amino acid. Examples of radiolabels include, but are not limited to, the following radioisotopes or radionucleotides: $^3$H, $^{14}$C, $^{15}$N, $^{35}$S, $^{90}$Y, $^{99}$Tc, $^{111}$In, $^{125}$I, $^{131}$I. The radiolabel may be used for both diagnostic and therapeutic purposes.

Means of detecting such labels are well known to those of skill in the art. Thus, for example, radiolabels may be detected using photographic film or scintillation counters, fluorescent markers may be detected using a photodetector to detect emitted illumination. Enzymatic labels are typically detected by providing the enzyme with a substrate and detecting the reaction product produced by the action of the enzyme on the substrate, and colorimetric labels are detected by simply visualizing the colored label.

An antibody, including $V_HH$ monoclonal antibodies, can also be derivatized with a chemical group such as polyethylene glycol (PEG), a methyl or ethyl group, or a carbohydrate group. These groups may be useful to improve the biological characteristics of the antibody, such as to increase serum half-life or to increase tissue binding. An immunoadhesin can be produced.

Means of detecting such labels are well known to those of skill in the art. Thus, for example, radiolabels may be detected using photographic film or scintillation counters, fluorescent markers may be detected using a photodetector to detect emitted illumination. Enzymatic labels are typically detected by providing the enzyme with a substrate and detecting the reaction product produced by the action of the enzyme on the substrate, and colorimetric labels are detected by simply visualizing the colored label.

Polynucleotides, Expression and Production

Nucleotide sequences are provided herein that encode a monoclonal antibody, such as a $V_HH$ monoclonal antibody, or an antigen binding fragment thereof, that specifically binds a NoV polypeptide, such as a Gengroup II or Genogroup I NoV polypeptide. The nucleic acid sequence can encode a $V_HH$ monoclonal antibody that specifically binds a MD2004 virus polypeptide or a Norwalk virus polypeptide. The antibody can specifically bind a polypeptide, such as VP1 or VP2. Expression vectors are also provided for their efficient expression in cells (for example, mammalian cells, plant cells, chloroplasts insect cells, yeast, or bacteria).

Recombinant expression of an antibody generally requires construction of an expression vector containing a polynucleotide that encodes the antibody or antibody fragment. Replicable vectors are provided including a nucleotide sequence encoding a $V_HH$ antibody molecule, and/or one or more heavy chain CDRs, and optionally a light chain variable domain, operably linked to a promoter. Such vectors may include the nucleotide sequence encoding the constant region of an antibody molecule (see, e.g., U.S. Pat. Nos. 5,981,216; 5,591,639; 5,658,759 and 5,122,464) and the variable domain of the $V_HH$ antibody may be cloned into such a vector. Nucleic acid molecules (also referred to as polynucleotides) encoding the polypeptides provided herein (including, but not limited to $V_HH$ antibodies) can readily be produced by one of skill in the art. For example, these nucleic acids can be produced using the amino acid sequences provided herein (such as the CDR sequences or variable domain sequences), and optionally sequences available in the art (such as framework sequences), and the genetic code.

$V_HH$ nucleic acid sequences are set forth as SEQ ID NOs: 39-68 and include degenerate variants thereof. One of skill in the art can readily use the genetic code to construct a variety of functionally equivalent nucleic acids, such as nucleic acids which differ in sequence but which encode the same antibody sequence, or encode a conjugate or fusion protein including the $V_HH$ nucleic acid sequence.

Nucleic acid sequences encoding the antibodies that specifically bind a NoV polypeptide, such as a Genogroup II or Genogroup I NoV polypeptide, such as antibodies that bind a NV polypeptide, including but not limited to VP1 or VP2 can be prepared by any suitable method including, for example, cloning of appropriate sequences or by direct chemical synthesis by methods such as the phosphotriester method of Narang et al., Meth. Enzymol. 68:90-99, 1979; the phosphodiester method of Brown et al., Meth. Enzymol. 68:109-151, 1979; the diethylphosphoramidite method of Beaucage et al., Tetra. Lett. 22:1859-1862, 1981; the solid phase phosphoramidite triester method described by Beaucage and Caruthers, Tetra. Letts. 22(20):1859-1862, 1981, for example, using an automated synthesizer as described in, for example, Needham-VanDevanter et al., Nucl. Acids Res. 12:6159-6168, 1984; and, the solid support method of U.S. Pat. No. 4,458,066. Chemical synthesis produces a single stranded oligonucleotide. This can be converted into double stranded DNA by hybridization with a complementary sequence or by polymerization with a DNA polymerase using the single strand as a template. One of skill would recognize that while chemical synthesis of DNA is generally limited to sequences of about 100 bases, longer sequences may be obtained by the ligation of shorter sequences.

Exemplary nucleic acids can be prepared by cloning techniques. Examples of appropriate cloning and sequencing techniques, and instructions sufficient to direct persons of skill through many cloning exercises are found in Sambrook et al., supra, Berger and Kimmel (eds.), supra, and Ausubel, supra. Product information from manufacturers of biological reagents and experimental equipment also provide useful information. Such manufacturers include the SIGMA Chemical Company (Saint Louis, Mo.), R&D Systems (Minneapolis, Minn.), Pharmacia Amersham (Piscataway, N.J.), CLONTEC$_H$ Laboratories, Inc. (Palo Alto, Calif.), Chem Genes Corp., Aldrich Chemical Company (Milwaukee, Wis.), Glen Research, Inc., GIBCO BRL Life Technologies, Inc. (Gaithersburg, Md.), Fluka Chemica-Biochemika Analytika (Fluka Chemie AG, Buchs, Switzerland), Invitrogen (Carlsbad, Calif.), and Applied Biosystems (Foster City, Calif.), as well as many other commercial sources known to one of skill.

Nucleic acids can also be prepared by amplification methods. Amplification methods include polymerase chain reaction (PCR), the ligase chain reaction (LCR), the transcription-based amplification system (TAS), the self-sustained sequence replication system (3SR). A wide variety of cloning methods, host cells, and in vitro amplification methodologies are well known to persons of skill.

Any of the nucleic acids encoding any of the antibodies, variable domains, or CDRs disclosed herein (or fragment thereof) can be expressed in a recombinantly engineered cell such as bacteria, plant, yeast, insect and mammalian cells. These antibodies can be expressed as individual variable domain or can be expressed as a fusion protein. Additionally, all the $V_HH$ antibodies may be easily expressed in several biotechnological platforms such as transgenic rice or the milk of a transgenic cow.

An immunoadhesin can also be expressed. The nucleic acid sequences can optionally encode a leader sequence.

It is expected that those of skill in the art are knowledgeable in the numerous expression systems available for expression of proteins including *E. coli*, other bacterial hosts, yeast, and various higher eukaryotic cells such as the COS, CHO, HeLa and myeloma cell lines. Once the expression vector is transferred to a host cell by conventional techniques, the transfected cells are then cultured by conventional techniques, such as to produce an antibody. Thus, host cells are provided containing a polynucleotide encoding a $V_HH$ antibody fragment thereof, or portion thereof, operably linked to a heterologous promoter. Mammalian cell lines available as hosts for expression of recombinant antibodies are well known in the art and include many immortalized cell lines available from the American Type Culture Collection (ATCC), including but not limited to Chinese hamster ovary (CHO) cells, HeLa cells, baby hamster kidney (BHK) cells, monkey kidney cells (COS), human hepatocellular carcinoma cells (e.g., Hep G2), human epithelial kidney 293 cells, and a number of other cell lines. Additional cell lines which may be used as hosts for expression of recombinant antibodies include, but are not limited to, insect cells (e.g. Sf21/Sf9, *Trichoplusia ni* Bti-Tn5b1-4) or yeast cells (e.g. *S. cerevisiae*, Pichia, U.S. Pat. No. 7,326,681), plant cells (US Published Patent Application No. 20080066200); and chicken cells (PCT Publication No. WO2008142124).

Mammalian cell lines available as hosts for expression of recombinant antibodies are well known in the art and include many immortalized cell lines available from the American Type Culture Collection (ATCC), including but not limited to Chinese hamster ovary (CHO) cells, HeLa cells, baby hamster kidney (BHK) cells, monkey kidney cells (COS), human hepatocellular carcinoma cells (e.g., Hep G2), human epithelial kidney 293 cells, and a number of other cell lines. Different host cells have characteristic and specific mechanisms for the post-translational processing and modification of proteins and gene products. Appropriate cell lines or host systems can be chosen to ensure the correct modification and processing of the antibody or portion thereof expressed. To this end, eukaryotic host cells which possess the cellular machinery for proper processing of the primary transcript, glycosylation, and phosphorylation of the gene product may be used. Such mammalian host cells include but are not limited to CHO, VERY, BHK, Hela, COS, MDCK, 293, 3T3, W138, BT483, Hs578T, HTB2, BT2O and T47D, NS0 (a murine myeloma cell line that does not endogenously produce any functional immunoglobulin chains), SP20, CRL7O3O and HsS78Bst cells. In one embodiment, human cell lines are of use. In one embodiment, the human cell line PER.C6. (Crucell, Netherlands) can be used. Additional cell lines which may be used as hosts for expression of recombinant antibodies include, but are not limited to, insect cells (e.g. Sf21/Sf9, *Trichoplusia ni* Bti-Tn5b1-4) or yeast cells (e.g. *S. cerevisiae*, Pichia, U.S. Pat. No. 7,326,681), plant cells (US Published Patent Application No. 20080066200); and chicken cells (PCT Publication No. WO2008142124).

The host cell can be a gram positive bacteria including, but not limited to, *Bacillus, Streptococcus, Streptomyces, Staphylococcus, Enterococcus, Lactobacillus, Lactococcus, Clostridium, Geobacillus*, and *Oceanobacillus*. Methods for expressing protein in gram positive bacteria, such as *Lactobaccillus* are well known in the art, see for example, U.S. Published Patent Application No. 20100/080774. Expression vectors for *lactobacillus* are described, for example in U.S. Pat. No. 6,100,388, and U.S. Pat. No. 5,728,571. Leader sequences can be included for expression in *Lactobacillus*. Gram negative bacteria include, but not limited to, *E. coli, Pseudomonas, Salmonella, Campylobacter, Helicobacter, Flavobacterium, Fusobacterium, Ilyobacter, Neisseria*, and *Ureaplasma*.

One or more DNA sequences encoding the antibody or fragment thereof can be expressed in vitro by DNA transfer into a suitable host cell. The term also includes any progeny of the subject host cell. It is understood that all progeny may not be identical to the parental cell since there may be mutations that occur during replication. Methods of stable transfer, meaning that the foreign DNA is continuously maintained in the host, are known in the art.

The expression of nucleic acids encoding the isolated proteins described herein can be achieved by operably linking the DNA to a promoter (which is either constitutive or inducible), followed by incorporation into an expression cassette. The promoter can be any promoter of interest, including a cytomegalovirus promoter and a human T cell lymphotrophic virus promoter (HTLV)-1. Optionally, an enhancer, such as a cytomegalovirus enhancer, is included in the construct. The cassettes can be suitable for replication and integration in either prokaryotes or eukaryotes. Typical expression cassettes contain specific sequences useful for regulation of the expression of the DNA encoding the protein. For example, the expression cassettes can include appropriate promoters, enhancers, transcription and translation terminators, initiation sequences, a start codon (i.e., ATG) in front of a protein-encoding gene, splicing signal for introns, sequences for the maintenance of the correct reading frame of that gene to permit proper translation of mRNA, and stop codons. The vector can encode a selectable marker, such as a marker encoding drug resistance (for example, ampicillin or tetracycline resistance).

To obtain high level expression of a cloned gene, it is desirable to construct expression cassettes which contain, at the minimum, a strong promoter to direct transcription, a ribosome binding site for translational initiation (internal ribosomal binding sequences), and a transcription/translation terminator. For *E. coli*, this includes a promoter such as the T7, trp, lac, or lambda promoters, a ribosome binding site, and preferably a transcription termination signal. For eukaryotic cells, the control sequences can include a promoter and/or an enhancer derived from, for example, an immunoglobulin gene, HTLV, SV40 or cytomegalovirus, and a polyadenylation sequence, and can further include splice donor and/or acceptor sequences (for example, CMV and/or HTLV splice acceptor and donor sequences). The cassettes can be transferred into the chosen host cell by well-known methods such as transformation or electroporation for *E. coli* and calcium phosphate treatment, electroporation or lipofection for mammalian cells. Cells transformed by the cassettes can be selected by resistance to antibiotics conferred by genes contained in the cassettes, such as the amp, gpt, neo and hyg genes.

When the host is a eukaryote, such methods of transfection of DNA as calcium phosphate coprecipitates, conventional mechanical procedures such as microinjection, electroporation, insertion of a plasmid encased in liposomes, or virus vectors may be used. Eukaryotic cells can also be cotransformed with polynucleotide sequences encoding the antibody, labeled antibody, or functional fragment thereof, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein (see for example, *Eukaryotic Viral Vectors*, Cold Spring Harbor Laboratory, Gluzman ed., 1982). One of skill in the art can readily use an expression systems such as plasmids and vectors of use in producing proteins in cells including higher eukaryotic cells such as the COS, CHO, HeLa and myeloma cell lines.

The disclosed antibodies and antibody fragments can be produced in a monocot plant, such as rice. In general, expression vectors for use include operably linked components that constitute a chimeric gene: a promoter from the gene of a maturation-specific monocot plant storage protein, a first DNA sequence, operably linked to the promoter, encoding a monocot plant seed-specific signal sequence (such as an N-terminal leader sequence or a C-terminal trailer sequence) capable of targeting a polypeptide linked thereto to an endosperm cell, such as to an endosperm-cell organelle, for example to a protein storage body, and a second DNA sequence, linked in translation frame with the first DNA sequence, encoding the $V_HH$ antibody or antigen binding fragment thereof. The signal sequence can be cleaved from the $V_HH$ antibody or antigen binding fragment thereof in the plant cell. The chimeric gene, in turn, is typically placed in a suitable plant-transformation vector having (i) companion sequences upstream and/or downstream of the chimeric gene which are of plasmid or viral origin and provide necessary characteristics to the vector to permit the vector to move DNA from bacteria to the desired plant host; (ii) a selectable marker sequence; and (iii) a transcriptional termination region generally at the opposite end of the vector from the transcription initiation regulatory region.

The chimeric gene, in turn, is typically placed in a suitable plant-transformation vector having (i) companion sequences upstream and/or downstream of the chimeric gene which are of plasmid or viral origin and provide necessary characteristics to the vector to permit the vector to move DNA from bacteria to the desired plant host; (ii) a selectable marker sequence; and (iii) a transcriptional termination region generally at the opposite end of the vector from the transcription initiation regulatory region.

Numerous types of appropriate expression vectors, and suitable regulatory sequences are known in the art for a variety of plant host cells. The promoter region is chosen to be regulated in a manner allowing for induction under seed-maturation conditions. In one aspect of this embodiment of the invention, the expression construct includes a promoter which exhibits specifically upregulated activity during seed maturation. Promoters for use in the invention are typically derived from cereals such as rice, barley, wheat, oat, rye, corn, millet, triticale or sorghum. Examples of such promoters include the maturation-specific promoter region associated with one of the following maturation-specific monocot plant storage proteins: rice glutelins, oryzins, and prolamines, barley hordeins, wheat gliadins and glutelins, maize zeins and glutelins, oat glutelins, and sorghum kafirins, millet pennisetins, and rye secalins. Other promoters suitable for expression in maturing seeds include the barley endosperm-specific B1-hordein promoter, GluB-2 promoter, Bx7 promoter, Gt3 promoter, GluB-1 promoter and Rp-6 promoter, particularly if these promoters are used in conjunction with transcription factors. In some embodiments, the expression of the nucleic acid encoding the $V_HH$ antibody or antigen binding fragment thereof from a promoter that is preferentially expressed in plant seed tissue. Examples of such promoter sequences include those sequences derived from sequences encoding plant storage protein genes or from genes involved in fatty acid biosynthesis in oilseeds. Non-limiting examples are a glutelin (Gt1) promoter, which provides gene expression in the outer layer of the endosperm, and a globulin (Gib) promoter, which provides gene expression in the center of the endosperm. Promoter sequences for regulating transcription of operably linked gene coding sequences include naturally-occurring promoters, or regions thereof capable of directing seed-specific transcription, and hybrid promoters, which combine elements of more than one promoter. In some examples, the promoter is native to the same plant species as the plant cells into which the chimeric nucleic acid construct is to be introduced. In other embodiments, the promoter is heterologous to the plant host cell. In other embodiments, a seed-specific promoter from one type of monocot may be used regulate transcription of a nucleic acid coding sequence from a different monocot or a non-cereal monocot. See, for example, U.S. Published Patent Application No. 2012/0195883 and U.S. Published Patent Application No. 2008/0318277.

In some embodiments the monocot plant can be stably transformed with a chimeric gene having (i) a seed maturation-specific promoter, (ii) operably linked to said promoter, a leader DNA sequence encoding a monocot seed-specific transit sequence capable of targeting a linked polypeptide to an endosperm-cell organelle, and (iii) a protein-coding sequence encoding a $V_HH$ or antigen binding fragment thereof, (b) cultivating the transformed plant under seed-maturation conditions, (c) harvesting the seeds from the cultivated plant, (d) extracting the harvested seeds with an aqueous solution, thereby obtaining an extract of water soluble plant components comprising at least 3% by total protein weight of the $V_HH$ or antigen binding fragment thereof, (e) purifying the $V_HH$ or antigen binding fragment thereof from the aqueous solution. Plant cells or tissues are transformed with expression constructs (heterologous nucleic acid constructs, e.g., plasmid DNA into which the gene of interest has been inserted) using a variety of standard techniques, including, but not limited to, the use of *Agrobacterium*.

Suitable vectors and methods for expressing the $V_HH$ antibody or antigen binding fragment thereof in transgenic plants are disclosed, for example, in U.S. Published Patent Application No. 2012/0195883 and U.S. Published Patent Application No. 2008/0318277, which are incorporated herein by reference.

Modifications can be made to a nucleic acid encoding a polypeptide described herein without diminishing its biological activity. Some modifications can be made to facilitate the cloning, expression, or incorporation of the targeting molecule into a fusion protein. Such modifications are well known to those of skill in the art and include, for example, termination codons, a methionine added at the amino terminus to provide an initiation, site, additional amino acids placed on either terminus to create conveniently located restriction sites, codon optimization, or additional amino acids (such as poly His) to aid in purification steps. In addition to recombinant methods, the immunoconjugates, effector moieties, and antibodies of the present disclosure can also be constructed in whole or in part using standard peptide synthesis well known in the art.

Once expressed, the recombinant immunoconjugates, antibodies, and/or effector molecules can be purified according to standard procedures of the art of the expression system used, including ammonium sulfate precipitation, affinity columns, column chromatography, preparative gel filtration, and the like (see, generally, R. Scopes, PROTEIN PURIFICATION, Springer-Verlag, N.Y., 1982). The antibodies, immunoconjugates and effector molecules need not be 100% pure. In some embodiments, the $V_HH$ antibodies or antigen binding fragment thereof can be purified from seed extracts (see, generally, Greenham and Altosaar, Methods in Mol. Biol. 956: 311, 2013; Broz et al., Gen. Eng. Biotechnol. News 33(4), 2013; Nandi et al., Trans. Res. 14: 237, 2005). The antibody can be purified from a seed product by methods that include grinding, filtration, heat, pressure, salt extraction, evaporation, or chromatography (see U.S. Published Patent Application No. 20120195883). Once purified, partially or to homogeneity as desired, if to be used therapeutically, the polypeptides should be substantially free of endotoxin.

Methods for expression of antibodies and/or refolding to an appropriate active form, including single domain or single chain antibodies, from bacteria such as *E. coli*, have been described and are well-known and are applicable to the antibodies disclosed herein. See, Buchner et al., Anal. Biochem. 205:263-270, 1992; Pluckthun, Biotechnology 9:545, 1991; Huse et al., Science 246:1275, 1989 and Ward et al., Nature 341:544, 1989.

In addition to recombinant methods, the antibodies, labeled antibodies and functional fragments thereof that are disclosed herein can also be constructed in whole or in part using standard peptide synthesis. Solid phase synthesis of the polypeptides of less than about 50 amino acids in length can be accomplished by attaching the C-terminal amino acid of the sequence to an insoluble support followed by sequential addition of the remaining amino acids in the sequence. Techniques for solid phase synthesis are described by Barany & Merrifield, The Peptides: Analysis, Synthesis, Biology. Vol. 2: Special Methods in Peptide Synthesis, Part A. pp. 3-284; Merrifield et al., J. Am. Chem. Soc. 85:2149-2156, 1963, and Stewart et al., Solid Phase Peptide Synthesis, 2nd ed., Pierce Chem. Co., Rockford, Ill., 1984. Proteins of greater length may be synthesized by condensation of the amino and carboxyl termini of shorter fragments. Methods of forming peptide bonds by activation of a carboxyl terminal end (such as by the use of the coupling reagent N,N'-dicylohexylcarbodimide) are well known in the art. Once an antibody molecule has been produced, it may be purified by any method known in the art for purification of an immunoglobulin molecule, for example, by chromatography (e.g., ion exchange, affinity, and sizing column chromatography), centrifugation, differential solubility, or by any other standard technique for the purification of proteins. Further, the antibodies or fragments thereof may be fused to heterologous polypeptide sequences (referred to herein as "tags") described above or otherwise known in the art to facilitate purification.

Compositions and Therapeutic Methods

Methods are disclosed herein for the prevention or treatment of a NoV infection. Included within the NoVs are at least 5 genogroups (GI-GV), separated by nucleic acid and amino acid sequences, which comprise 15 genetic clusters. Methods are provided for the prevention and/or treatment of NoVs from any of these groups. Examples of NoVs include, but are not limited to, NV (NV, see, for example, GENBANK® Accession No. M87661, NP_056821), P7-587 virus (see, for example, GENBANK® Accession No. FJ384783), Southampton virus (SHV, see, for example, GENBANK® Accession No. L07418), Desert Shield virus (DSV, see, for example, GENBANK® Accession No. U04469), Hesse virus (HSV, see, for example, GENBANK® Accession No. AF093797), Chiba virus (CHV, see, for example, GENBANK® Accession No. AB042808), Hawaii virus (HV, see, for example, GENBANK® Accession No. U07611), Snow Mountain virus (SMV, see, for example, GENBANK® Accession No. U70059), Toronto virus (TV, see for example, GENBANK® Accession No. UO2030), Bristol virus (BV, see for example, GENBANK® Accession No. X76716), Jena virus (JV, see, for example, GENBANK® Accession No. AJ011099), MD145-12 virus (MD145-12, see, for example, GENBANK® Accession No. AY032605), Aichi virus (AV124-89, see, for example, GENBANK® Accession No. AB031013), Camberwell (CV, see, for example, GENBANK® Accession No. AF145896), Lordsdale virus (LV, see, for example, GENBANK® Accession No. X86557), Grimsby virus (GrV, see, for example, GENBANK® Accession No. AJ004864), Mexico virus (MXV, see, for example, GENBANK® Accession No. U22498), Boxer (see, for example, GENBANK® Accession No. AF538679), C59 (see, for example, GENBANK® Accession No. AF435807), VA98115 (see, for example, GENBANK® Accession No. AY038598), BUDS (see, for example, GENBANK® Accession No. AY660568), MOH (see, for example, GENBANK® Accession No. AF397156), Parris Island (PiV; see, for example, GENBANK® Accession No. AY652979), VA98387 (see, for example, GENBANK® Accession No. AY038600), VA97207 (see, for example, GENBANK® Accession No. AY038599), and Operation Iraqi Freedom (see, for example, OIF, GEN-BANK® Accession No. AY675554). In some embodiments, methods are provided for the treatment and/or prevention of Genogroup I NV. In some embodiments, methods are provided for the treatment and/or prevention of Genogroup II NV. In some non-limiting examples, methods are provided for the treatment and/or prevention of a NV infection.

Prevention can include inhibition of infection with the NoV, such as a Norwalk virus or MD2004 virus. In some embodiments, the methods include contacting a cell with an effective amount of one or more of the antibodies disclosed herein. In some embodiments, the antibody specifically binds VP1, or an antigen binding fragment thereof. The method can also include administering to a subject a therapeutically effective amount of a $V_HH$ monoclonal antibody, or a nucleic acid encoding the antibody. Neutralizing MAbs against NoVs can be used as emergency prophylaxis to protect individuals in the proximity of a developing NoV outbreak, or when encountering an increased risk of exposure. Thus, the methods can include selecting a subject at risk of exposure to a NoV. The antibodies can also be used to clear a chronic infection and reduce viral load in a severe case of NoV gastroenteritis.

In other embodiments, methods are disclosed for ameliorating one or more symptoms associated with a NoV infection, such as a Genogroup I or Genogroup II NoV infection, for example, a Norwalk virus infection. Generally, the method includes administering an antibody or antibody (antigen-binding) fragment that specifically binds a NoV polypeptide, such as a Norwalk virus polypeptide. The antibody can specifically bind VP1. In some embodiments, the disclosed antibodies can be used in treatment to alleviate chronic NoV gastroenteritis in debilitated or immunocompromised individuals. Thus, the method can include selecting a subject with gastroenteritis. In some examples, the subject is immunocompromised. In some embodiments, the subject is a premature infant. In some embodiments, an individual is debilitated by chemotherapy for cancer. In some embodiments, an elderly individual with prolonged NoV disease can be treated.

The NoV infection does not need to be completely eliminated for the composition to be effective. For example, a composition can decrease the NoV infection in a population by a desired amount, for example by at least 10%, at least 20%, at least 50%, at least 60%, at least 70%, at least 80%, at least 90%, at least 95%, at least 98%, or 100%, as compared to the rate of infection in the absence of the composition. In addition, a composition can decrease viral titer by at least 10%, at least 20%, at least 50%, at least 60%, at least 70%, at least 80%, at least 90%, at least 95%, at least 98%, or 100% in a subject.

In example, the subject is also administered an effective amount of an additional agent, such as anti-viral agent. The methods can include administration of one on more additional agents known in the art. The subject can hydrated and administered balancing electrolytes.

A therapeutically effective amount of a NoV-specific, such as a Genogroup I or Genogroup II-specific (or Norwalk virus specific) $V_HH$ monoclonal antibody or antigen binding fragment (or the nucleic acid encoding the antibody or antigen binding fragment), or nucleic acid, will depend upon the severity of the disease and/or infection and the general state of the patient's health. A therapeutically effective amount of the antibody can provide either subjective relief of a symptom(s) or an objectively identifiable improvement as noted by the clinician or other qualified observer. As noted above, these compositions can be administered in conjunction with another therapeutic agent, either simultaneously or sequentially. For any application, the antibody, antigen binding fragment, or nucleic acid encoding the antibody or antigen binding fragment can be combined with anti-viral therapy.

In one embodiment, administration of the monoclonal antibody (or nucleic acid encoding the antibody), such as the $V_HH$ monoclonal antibody, results in a reduction in the establishment of a virus infection and/or reducing subsequent disease progression in a subject. A reduction in the establishment of NoV infection, such as a Norwalk virus infection, or a MD2004 virus infection, and/or a reduction in subsequent disease progression can encompass a statistically significant reduction in viral activity. In some embodiments, the method reduces disease in a subject. In some embodiments, methods are disclosed for treating a subject with a NoV infection, such as a Norwalk virus infection or a MD2004 virus infection. These methods include administering to the subject a therapeutically effective amount of an antibody, or a nucleic acid encoding the antibody, thereby preventing or treating the viral infection.

Single or multiple administrations of the compositions including the antibody, antigen binding fragment, or nucleic acid encoding the antibody or antigen binding fragment, that are disclosed herein, are administered depending on the dosage and frequency as required and tolerated by the patient. In any event, the composition should provide a sufficient quantity of at least one of the antibodies disclosed herein to effectively treat the patient. The dosage can be administered once but may be applied periodically until either a therapeutic result is achieved or until side effects warrant discontinuation of therapy. In one example, a dose of the antibody is infused for thirty minutes every other day. In this example, about one to about ten doses can be administered, such as three or six doses can be administered every other day. In a further example, a continuous infusion is administered for about five to about ten days. The subject can be treated at regular intervals, such as monthly, until a desired therapeutic result is achieved. Generally, the dose is sufficient to treat or ameliorate symptoms or signs of disease without producing unacceptable toxicity to the patient.

Compositions are provided that include one or more of the $V_HH$ monoclonal antibodies that specifically bind a NoV polypeptide, such as a Genogroup I or Genogroup II NoV polypeptide, such as a Norwalk virus polypeptide (for example an antibody that specifically binds VP1), or antigen binding fragments of any of these antibodies, and nucleic acids encoding these antibodies (and antigen binding fragments) that are disclosed herein in a carrier. The compositions can be prepared in unit dosage forms for administration to a subject. The amount and timing of administration are at the discretion of the treating physician to achieve the desired purposes. The antibody and/or nucleic acid can be formulated for systemic or local administration. In one example, the antibody and/or nucleic acid is formulated for parenteral administration, such as intravenous administration. In some embodiments, administration is intramuscular.

Compositions also can be formulated for enteric delivery. Various studies have been made on a method of releasing or delivering a drug selectively to a specific site in the intestine. In addition to classic methods of using enteric-coated preparations or sustained release preparations (Chemical & Pharmaceutical Bulletin, 40, 3035-3041, 1992), enteric-coated sustained-release preparations and time-limited release enteric-coated preparations have been proposed (Japanese Patent No. 3185206, and PCT Publication No. WO 01/23000).

Active ingredients can also be entrapped in microcapsules prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980). Specifically, liposomes containing the immunogens or antibodies can be prepared by such methods as described in Epstein et al., Proc. Natl. Acad. Sci. USA, 82:3688, 1985; Hwang et al., Proc. Natl. Acad. Sci. USA, 77:4030, 1980; and U.S. Pat. Nos. 4,485,045 and 4,544,545. Liposomes with enhanced circulation time are disclosed in U.S. Pat. No. 5,013,556. The everse-phase evaporation method can be used with a lipid composition comprising phosphatidylcholine, cholesterol and PEG-derivatized phosphatidylethanolamine (PEG-PE). Liposomes are extruded through filters of defined pore size to yield liposomes with the desired diameter. The antibodies disclosed herein can be conjugated to the liposomes as described, for example, in Martin et al., J. Biol. Chem., 257:286-288, 1982, via a disulfide interchange reaction.

The compositions for administration can include a solution of the antibody, such as the $V_HH$ monoclonal antibody or antigen binding fragment dissolved in a pharmaceutically acceptable carrier, such as an aqueous carrier. A variety of aqueous carriers can be used, for example, buffered saline and the like. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of antibody in these formulations can vary widely, and will be selected primarily based on fluid volumes, viscosities, body weight and the like in accordance with the particular mode of administration selected and the subject's needs. In some embodiments, administration is intravenous.

Controlled-release parenteral formulations can be made as implants, oily injections, or as particulate systems. For a broad overview of protein delivery systems see, Banga, Therapeutic Peptides and Proteins: Formulation, Processing, and Delivery Systems, Technomic Publishing Company, Inc., Lancaster, Pa., 1995. Particulate systems include microspheres, microparticles, microcapsules, nanocapsules, nanospheres, and nanoparticles. Microcapsules contain the therapeutic protein, such as a cytotoxin or a drug, as a central core. In microspheres the therapeutic is dispersed throughout the particle. Particles, microspheres, and microcapsules smaller than about 1 μm are generally referred to as nanoparticles, nanospheres, and nanocapsules, respectively. Capillaries have a diameter of approximately 5 μm so that only nanoparticles are administered intravenously. Microparticles are typically around 100 μm in diameter and are administered subcutaneously or intramuscularly. See, for example, Kreuter, Colloidal Drug Delivery Systems, J. Kreuter, ed., Marcel Dekker, Inc., New York, N.Y., pp. 219-342, 1994; and Tice & Tabibi, Treatise on Controlled Drug Delivery, A. Kydonieus, ed., Marcel Dekker, Inc. New York, N.Y., pp. 315-339, 1992.

Polymers can be used for ion-controlled release of the antibody compositions disclosed herein. Various degradable and nondegradable polymeric matrices for use in controlled drug delivery are known in the art (Langer, Accounts Chem. Res. 26:537-542, 1993). For example, the block copolymer, polaxamer 407, exists as a viscous yet mobile liquid at low temperatures but forms a semisolid gel at body temperature. It has been shown to be an effective vehicle for formulation and sustained delivery of recombinant interleukin-2 and urease (Johnston et al., Pharm. Res. 9:425-434, 1992; and Pec et al., J. Parent. Sci. Tech. 44(2):58-65, 1990). Alternatively, hydroxyapatite has been used as a microcarrier for controlled release of proteins (Ijntema et al., Int. J. Pharm.112:215-224, 1994). In yet another aspect, liposomes are used for controlled release as well as drug targeting of the lipid-capsulated drug (Betageri et al., Liposome Drug Delivery Systems, Technomic Publishing Co., Inc., Lancaster, Pa., 1993). Numerous additional systems for controlled delivery of therapeutic proteins are known (see U.S. Pat. No. 5,055,303; U.S. Pat. No. 5,188,837; U.S. Pat. No. 4,235,871; U.S. Pat. No. 4,501,728; U.S. Pat. No. 4,837,028; U.S. Pat. No. 4,957,735; U.S. Pat. No. 5,019,369; U.S. Pat. No. 5,055,303; U.S. Pat. No. 5,514,670; U.S. Pat. No. 5,413,797; U.S. Pat. No. 5,268,164; U.S. Pat. No. 5,004,697; U.S. Pat. No. 4,902,505; U.S. Pat. No. 5,506,206; U.S. Pat. No. 5,271,961; U.S. Pat. No. 5,254,342 and U.S. Pat. No. 5,534,496).

A typical pharmaceutical composition for intravenous administration includes about 0.1 to 10 mg/kg of antibody per day, or 0.5 to 15 mg/kg of antibody per day. Dosages from 0.1 up to about 100 mg/kg per subject per day may be used, particularly if the agent is administered to a secluded site and not into the circulatory or lymph system, such as into a body cavity or into a lumen of an organ. Exemplary doses include 1 to 10 mg/kg, such as 2 to 8 mg/kg, such as 3 to 6 mg/kg. Actual methods for preparing administrable compositions will be known or apparent to those skilled in the art and are described in more detail in such publications as Remington's Pharmaceutical Science, 19th ed., Mack Publishing Company, Easton, Pa. (1995). Administration can be oral.

Antibodies may be provided in lyophilized form and rehydrated with sterile water before administration, although they are also provided in sterile solutions of known concentration. The antibody solution is then added to an infusion bag containing 0.9% sodium chloride, USP, and typically administered at a dosage of from 0.1 to 10 mg/kg or 0.5 to 15 mg/kg of body weight. Exemplary doses include 1 to 10 mg/kg, such as 2 to 8 mg/kg, such as 3 to 6 mg/kg. Considerable experience is available in the art in the administration of antibody drugs, which have been marketed in the U.S. since the approval of RITUXAN® in 1997. Antibodies can be administered by slow infusion, rather than in an intravenous push or bolus. In one example, a higher loading dose is administered, with subsequent, maintenance doses being administered at a lower level. For example, an initial loading dose of 4 mg/kg may be infused over a period of some 90 minutes, followed by weekly maintenance doses for 4-8 weeks of 2 mg/kg infused over a 30 minute period if the previous dose was well tolerated.

A therapeutically effective amount of a nucleic acid encoding the antibody or an antigen binding fragment thereof can be administered to a subject in need thereof. One approach to administration of nucleic acids is direct immunization with plasmid DNA, such as with a mammalian expression plasmid. The nucleotide sequence encoding the antibody or fragment thereof can be placed under the control of a promoter to increase expression of the molecule. Immunization by nucleic acid constructs is well known in the art and taught, for example, in U.S. Pat. No. 5,643,578, and U.S. Pat. No. 5,593,972 and U.S. Pat. No. 5,817,637.

U.S. Pat. No. 5,880,103 describes several methods of delivery of nucleic acids to an organism. The methods include liposomal delivery of the nucleic acids.

In another approach to using nucleic acids, an antibody or antigen binding fragment thereof can also be expressed by attenuated viral hosts or vectors or bacterial vectors, which can be administered to a subject. Recombinant vaccinia virus, adeno-associated virus (AAV), herpes virus, retrovirus, cytomegalovirus, poxvirus or other viral vectors can be used to express the antibody. For example, vaccinia vectors are described in U.S. Pat. No. 4,722,848. BCG (Bacillus Calmette Guerin) provides another vector for expression of the disclosed antibodies (see Stover, Nature 351:456-460, 1991).

In one embodiment, a nucleic acid encoding the antibody or an antigen binding fragment thereof is introduced directly into cells. For example, the nucleic acid can be loaded onto gold microspheres by standard methods and introduced into the skin by a device such as Bio-Rad's Heliosa Gene Gun. The nucleic acids can be "naked," consisting of plasmids under control of a strong promoter.

Typically, the DNA is injected into muscle, although it can also be injected directly into other sites. Dosages for injection are usually around 0.5 mg/kg to about 50 mg/kg, and typically are about 0.005 mg/kg to about 5 mg/kg (see, e.g., U.S. Pat. No. 5,589,466).

In some examples, a subject is administered the DNA encoding the antibody or antibody binding fragments thereof to provide in vivo antibody production, for example using the cellular machinery of the subject Immunization by nucleic acid constructs is well known in the art and taught, for example, in U.S. Pat. No. 5,643,578, and U.S. Pat. No. 5,593,972 and U.S. Pat. No. 5,817,637. U.S. Pat. No. 5,880,103 describes several methods of delivery of nucleic acids encoding to an organism. The methods include liposomal delivery of the nucleic acids. Such methods can be applied to the production of an antibody, or antibody binding fragments thereof, by one of ordinary skill in the art.

One approach to administration of nucleic acids is direct administration with plasmid DNA, such as with a mammalian expression plasmid. The nucleotide sequence encoding the disclosed antibody, or antibody binding fragments thereof, can be placed under the control of a promoter to increase expression.

In another approach to using nucleic acids, a disclosed antibody, or antibody binding fragments thereof can also be expressed by attenuated viral hosts or vectors or bacterial vectors. Recombinant vaccinia virus, adeno-associated virus (AAV), herpes virus, retrovirus, cytomegalovirus or other viral vectors can be used to express the antibody. For example, vaccinia vectors and methods useful protocols are described in U.S. Pat. No. 4,722,848. BCG (Bacillus Calmette Guerin) provides another vector for expression of the disclosed antibodies (see Stover, Nature 351:456-460, 1991).

In one embodiment, a nucleic acid encoding a disclosed antibody, or antibody binding fragments thereof, is introduced directly into cells. For example, the nucleic acid can be loaded onto gold microspheres by standard methods and introduced into the skin by a device such as Bio-Rad's HELIOS™ Gene Gun. The nucleic acids can be "naked," consisting of plasmids under control of a strong promoter.

Typically, the DNA is injected into muscle, although it can also be injected directly into other sites. Dosages for injection are usually around 0.5 µg/kg to about 50 mg/kg, and typically are about 0.005 mg/kg to about 5 mg/kg (see, e.g., U.S. Pat. No. 5,589,466).

Diagnostic Methods and Kits

A method is provided herein for the detection of a NoV, such as a Genogroup I or Genogroup II NoV in vitro or in vivo. The methods can be used to detect, for example, a Norwalk virus infection or a MD2004 virus infection. In one example, the NoV is detected in a biological sample, and can be used to an infection with the virus. The method can detect the presence of a NoV polypeptide, such as VP1. The sample can be any sample, including, but not limited to, tissue from biopsies, autopsies and pathology specimens. Biological samples also include sections of tissues, for example, frozen sections taken for histological purposes. Biological samples further include body fluids, such as blood, serum, plasma, sputum, spinal fluid, nasopharyngeal secretions, or urine. Biological samples can include stool.

In one embodiment, methods are provided for detecting the presence of a NoV, such as a Genogroup I or Genogroup II NoV. The presence of the NoV is detected in in a sample suspected of containing the virus, wherein the method includes contacting the sample with a VIM antibody disclosed herein, or antigen binding fragment thereof, and determining binding of the antibody or antigen binding fragment to the virus in the sample. Binding of the antibody to virus in the sample is indicative of the presence of the virus in the sample. In one embodiment, the sample is a biological sample. In some examples, the sample is a stool sample. In other embodiments, the sample is an environmental sample. In some embodiments, the method distinguishes a particular NoV from other NoV, distinguishes a Genogroup I NoV, or distinguishes a Genogroup II NoV.

As discussed above, NoVs are divided into five distinct genogroups based on VP1 sequence similarity. Virus strains from Genogroups I and II are responsible for most human infections, and these genogroups are further subdivided into more than 25 different genotypes (Zheng et al., Virology 346:312-23, 2006; Kroneman et al., Arch Virol 158(10): 2059-68, 2013.). In some embodiments, methods are provided for detecting or distinguishing a Genogroup I and/or Genogroup II NoV. The method includes contacting the sample with a $V_H H$ monoclonal antibody disclosed herein, or an antigen binding fragment thereof, and determining binding of the antibody to the virus in the sample. In some embodiments, binding of the antibody to virus in the sample is indicative of the presence of a Genogroup NoV, such as GI.1 NV in the sample. In some examples, the sample is a stool sample. In other embodiments, the sample is an environmental sample.

In several embodiments, a method is provided for detecting a NoV infection, such as Norwalk virus infection in a subject. The disclosure provides a method for detecting a NoV in a biological sample, wherein the method includes contacting a biological sample with the antibody under conditions conducive to the formation of an immune complex, and detecting the immune complex, to detect the presence of a NoV polypeptide, such as, but not limited to, a Norwalk virus (NV) polypeptide in the biological sample. In some embodiments, NV VP1, is detected in the biological sample. In another example, detection of the virus in the sample confirms a diagnosis of a NoV infection, in a subject.

In some specific non-limiting examples, the $V_H H$ monoclonal antibody, or fragment thereof, specifically binds a NV polypeptide, such as VP1. In these examples, the method detects a GI NV infection in the subject, such as, but not limited to, a GI.1 NV infection.

The detection of a NoV can be achieved, for example, by contacting a sample to be tested, optionally along with a control sample, with the antibody under conditions that allow for formation of a complex between the antibody and the virus. Complex formation is then detected (e.g., using an ELISA). When using a control sample along with the test sample, a complex is detected in both samples and any statistically significant difference in the formation of complexes between the samples is indicative of the presence of a NoV in the test sample.

In some embodiments, the disclosed antibodies are used to test vaccines. For example to test if a vaccine composition can induce neutralizing antibodies to one or both Genogroups of NoV. Thus provided herein is a method for detecting testing a vaccine, wherein the method includes contacting a sample containing the vaccine, such as an NoV polypeptide, for example a Norwalk virus polypeptide, with the antibody under conditions conducive to the formation of an immune complex, and detecting the immune complex, to confirm the vaccine will be effective. In one example, the detection of the immune complex in the sample indicates that vaccine component, such as such as a NoV antigen (for example a Norwalk virus antigen, such as VP1) assumes a conformation capable of inducing neutralizing antibodies.

In some embodiments of the disclosed methods, an antibody is directly labeled with a detectable label. In another embodiment, the antibody that binds the NoV (the first antibody) is unlabeled and a second antibody or other molecule that can bind the antibody that binds the NoV polypeptide is utilized. As is well known to one of skill in the art, a second antibody is chosen that is able to specifically bind the specific species and class of the first antibody. For example, if the first antibody is a llama $V_H H$, then the secondary antibody may be an anti-$V_H H$ made in another species such as guinea pig or rabbit.

Suitable labels for the antibody or secondary antibody are described above, and include various enzymes, prosthetic groups, fluorescent materials, luminescent materials, magnetic agents and radioactive materials. Non-limiting examples of suitable enzymes include horseradish peroxidase, alkaline phosphatase, beta-galactosidase, or acetylcholinesterase. Non-limiting examples of suitable prosthetic group complexes include streptavidin/biotin and avidin/biotin. Non-limiting examples of suitable fluorescent materials include umbelliferone, fluorescein, fluorescein isothiocyanate, rhodamine, dichlorotriazinylamine fluorescein, dansyl chloride or phycoerythrin. A non-limiting exemplary luminescent material is luminol; a non-limiting exemplary a magnetic agent is gadolinium, and non-limiting exemplary radioactive labels include $^{125}I$, $^{131}I$, $^{35}S$ or $^3H$.

The immunoassays and method disclosed herein can be used for a number of purposes. Kits for detecting n NoV polypeptide will typically comprise a $V_H H$ antibody that binds a NoV polypeptide, such as a Norwalk virus polypeptide, for example, any of the antibodies disclosed herein. In some embodiments, a $V_H H$ antibody fragment is included in the kit. In a further embodiment, the $V_H H$ antibody is labeled (for example, with a fluorescent, radioactive, or an enzymatic label).

In one embodiment, a kit includes instructional materials disclosing means of use. The instructional materials may be written, in an electronic form (such as a computer diskette or compact disk) or may be visual (such as video files). The kits may also include additional components to facilitate the particular application for which the kit is designed. Thus, for example, the kit may additionally contain means of detecting a label (such as enzyme substrates for enzymatic labels, filter sets to detect fluorescent labels, appropriate secondary labels such as a secondary antibody, or the like). The kits may additionally include buffers and other reagents routinely used for the practice of a particular method. Such kits and appropriate contents are well known to those of skill in the art.

In one embodiment, the diagnostic kit comprises an immunoassay. Although the details of the immunoassays may vary with the particular format employed, the method of detecting the NoV polypeptide, such as a Norwalk virus polypeptide, such as VP1 and/or VP2 in a biological sample generally includes the steps of contacting the biological sample with an antibody which specifically reacts, under immunologically reactive conditions, to the viral polypeptide. The antibody is allowed to specifically bind under immunologically reactive conditions to form an immune complex, and the presence of the immune complex (bound antibody) is detected directly or indirectly.

The following examples are provided to illustrate certain particular features and/or embodiments. These examples should not be construed to limit the disclosure to the particular features or embodiments described.

EXAMPLES

There is no in vitro cell culture system to isolate and propagate NoV, impairing antigenic studies and vaccine development. From the 90s, it has been known that the expression of VP1 results in the formation of virus-like-particles (VLPs) that have been shown to be morphologically and antigenically similar to the native virion (Jiang et al., J Virol 66(11): 6527-32, 1992). VP1-VP2 VLPs vaccines are currently under evaluation (LoBue et al., Vaccine 24(24): 5220-34, 2006; Atmar et al., N Engl J Med 365(23): 2178-87, 2011; Wang et al., Vaccine 32(4): 445-52, 2013; Willyard, Nat Med 19(9): 1076-7, 2013; Scotti and Rybicki, Expert Rev Vaccines 12(2): 211-24, 2013) but there is no vaccine yet available. To date, there is no therapy available for the prevention or treatment of NoV diarrhea.

Crystallographic studies showed that NoVs bind carbohydrates of the human histo-blood group antigens (HBGAs) through the P2 protruding domain of VP1(Cao et al., J Virol 81(11): 5949-57, 2007; Choi et al., Proc Natl Acad Sci U.S. 105(27): 9175-80, 2008). A mechanism that considers that this binding facilitates viral entry into the epithelial cells of the gastrointestinal tract had been proposed (Zhang et al., PLoS One 8(7): e69379; 2013) It is thought that susceptibility to NoV in humans is determined by allelic variation of HBGAs (Tan and Jiang, Trends Microbiol 19(8): 382-8 2011). The measurement of antibodies that block the interaction between VLPs and HBGA carbohydrates might serve as a surrogate neutralization test. Several sources of carbohydrates have been used in these surrogate neutralization tests: synthetic carbohydrates, saliva, and pig gastric mucin (Harrington et al., J Virol 76(23): 12335-4, 2002; LoBue et al., Vaccine 24(24): 5220-34, 2006). The hemagglutination inhibition assay (IHA) using human red blood cell has also been used as a surrogate neutralization test (Hutson et al., J Infect Dis 185(9): 1335-7, 2002; Czako et al., Clin Vaccine Immunol 19(2): 284-7, 2012) insert. A correlation has been reported between IH Ab titers and the susceptibility to infection (Czako et al., Clin Vaccine Immunol 19(2): 284-7, 2012).

Because VLPs are antigenically similar to native virions (Jiang et al., J Virol 66(11): 6527-32, 1992), conventional monoclonal antibodies (MAbs) against NoV have been developed after immunization of mice with VLPs from several NoV genotypes (Hardy et al. Virology 217(1): 252-61, 1996; Yoda et al., Microbiol Immunol 44(11): 905-14, 2000; Yoda et al., BMC Microbiol 1: 24, 2001; Almanza et al.," J Clin Microbiol 46(12): 3971-9, 2008). Several cross-reactive MAbs have been identified, and most of them have been mapped to the S domain or the C-terminal region of the P1 domain (Li et al. Virus Res 151(2): 142-7, 2009; Yoda et al., BMC Microbiol 1: 24, 2001; Yoda et al., J Clin Microbiol 41(6): 2367-71, 2003; Parker et al., J Virol 79(12): 7402-9, 2005; Batten et al., Virology 356(1-2): 179-87, 2006; Oliver et al., J Clin Microbiol 44(3): 992-8, 2006; Shiota et al., J Virol 81(22): 12298-306, 2007; Almanza et al., J Clin Microbiol 46(12): 3971-9, 2008; Parra et al., PLoS One 8(6): e67592, 2013). It has been reported that certain MAbs block the interaction of VLPs with cells or synthetic HBGA (Lochridge et al., J Gen Virol 86(Pt 10): 2799-806, 2005; Lindesmith et al., J Virol 85(1): 231-42, 2011), and five HBGA-blocking sites have been mapped recently (de Rougemont et al., J Virol 85(9): 4057-70, 2011; Lindesmith et al., PLoS Pathog 8(5): e1002705, 2012). Single chain antibodies (scFv) were also constructed. Other non-conventional monoclonal antibodies have also been developed against Norwalk virus (Chen et al., J Virol 87(17): 9547-57, 2013). However, for an immunotherapy it is desirable to use a MAb derived from humans or chimpanzees or a molecule easy to humanize in order to reduce a host immune response to the MAb during and after the treatment to avoid the development of allergy and other hypersensitivity reaction.

A novel source of recombinant monoclonal antibodies derived from llamas is disclosed herein. IgG2 and IgG3 subtypes of the llamas lack the light chain and are called heavy chain antibodies; the variable domain of these antibodies is called $V_HH$ and is comprised of only one polypeptide chain. The $V_HH$ domain is a molecule of 15 kDa that is the smallest known domain that occurs in mammals, with full antigen-binding capacity showing affinities comparable to conventional antibodies (Muyldermans, Annu Rev Biochem 82: 775-97, 2013).

Disclosed herein are recombinant monoclonal $V_HH$, specific for two distinct NoV genogroups, GI.1 (Norwalk) and GII..4 (MD2004). In these studies, two llamas were immunized with GI.1 or GII.4 virus-like particles (VLPs). The surrogate neutralization assays indicated that the $V_HH$s nanoantibodies were able to block the binding of VLPs to different sources of carbohydrates. $V_HH$ antibodies were produced directed to human NoV. The generated $V_HH$ libraries represent a source of high quality reagents to be used for the antigenic characterization of the virus and virus detection, and possess high potential for immunoprophylaxis and therapeutic treatment of human NoV diarrhea.

Example 1

Materials and Methods

Expression and Purification of VLPs:

NoV VLPs containing VP1 and VP2 capsid proteins were expressed in a baculovirus system as described previously (Bok et al., J Virol 83(22): 11890-901, 2009; Esseili et al., Appl Environ Microbiol 78(3): 786-94, 2012; Green et al., J Clin Microbiol 35(7): 1909-14, 1997; Green, et al., J Clin Microbiol 31(8): 2185-91, 1993; Leite et al., Arch Virol 141(5): 865-75, 1996; Lew et al. Virology 200(1): 319-25, 1994). Briefly, the ORF2 and ORF3 genes of several norovirus strains were amplified by PCR and cloned into a pENTR plasmid (Invitrogen, Carlsbad, Calif.) to yield pENTRNoVVP1+VP2. Alternatively for some strains only VP1 VLPs were generated. Recombination of plasmid DNA with baculovirus DNA was performed using a Baculo direct kit (Invitrogen), and a baculovirus stock was obtained following transfection of the recombination product into Sf9 cells (serum-free adapted Sf9 cells; Invitrogen) as recommended by the manufacturer. The baculovirus stock was used to infect Sf9 suspension cultures for VLP production. Culture medium from baculovirus-infected cells was layered onto a 25% (wt/vol) sucrose cushion and subjected to centrifugation in an SW28 rotor at 76,200 g for 4 h at 4° C. The resulting pellets were dissolved in phosphate-buffered saline (PBS), pH 7.4, and further purified through a cesium chloride (CsCl) gradient by centrifugation in an SW55 rotor at 218,400 g for 18 h at 15° C. The collected fractions (densities of 1.3 g/ml) were dialyzed against PBS, and the protein concentration was determined with a commercial Bradford assay kit (Pierce, Rockford, Ill.). The VLPs were purified using a combination of sucrose and CsCl gradients and dialyzed in PBS overnight. The presence of VLPs was confirmed by electron microscopy.

For the different assays of this work VLPs of the following NoV strains were included: Hu/NoV/GI.1/Norwalk/1968/U.S., Hu/NoV/GI.1/P7-587/2007/Stromstad/Sweden; Hu/NoV/GI.3/Desert-Shield395/1990/U.S.; Hu/NoV/GII.4/MD2004/2004/U.S., Hu/NoV/GII.4/MD145-12/1997/U.S.; Hu/NoV/GII.1/Hawaii/1971/U.S.; Hu/NoV/GII.2/Henryton/1971/U.S.; Hu/NoV/GII.3/Toronto24/1991/CA; Hu/NoV/GII.4/CHDC4871/1977/U.S.; Hu/NoV/GII.4/HS-191/2001/U.S., Hu/NoV/GIV.1/S aintCloud624/1998/U.S., Hu/NoV/GII.3/Aus2001/2001/Aus, Hu/NoV/GII.3/Aus2007/2007/Aus, Hu/NoV/GII.3/Aus2008/2008/Aus, Hu/NoV/GII.3/CHDC2005/2005/U.S., Hu/NoV/GII.3/CHDC5261/1990/U.S., Hu/NoV/GII.3/CHDC4031/1988/U.S.; Hu/NoV/GII.3/CHDC32/1976/U.S., Hu/NoV/GII.7/DC119/U.S., Hu/NoV/GII.3/Maizuru/2000/JP, Hu/NoV/GII.14/M7/1999/U.S., Hu/NoV/GI.5/SzUG1/1997-99/JP, Hu/NoV/GI.6/Hesse/1997/GE, Hu/NoV/Snow Mountain/GII.2/U.S., Hu/NoV/GII.4/RockvilleD1/2012/U.S. and Hu/GII.6/Bethesda/2012/U.S.

As negative control, VLPs of Vesiviruses V1415 and Mink calicivirus were included. For the determination of the specificity of the $V_HH$ against the different subdomains of VP1, the VLP NV S domain/MD2004 P domain chimera and the VLP MD2004 S domain/NV P domain chimera were generated as previously described (Parra et al., Vaccine 30(24): 3580-6, 2012). Mutated VLPs used for epitope mapping were expressed and purified as the other VLPs used in this study.

Llama Immunization:

Two male llamas of one year of age were immunized by intramuscular injection with 3 doses (day 0, 30 and 73) or 4 doses (day 0, 30, 73 and 225) of vaccine containing around 300 µg/per dose of NoV VLP from Norwalk strain (Hu/NoV/GI.1/Norwalk/1968/U.S.), or from MD2004 strain (Hu/NoV/GII.4/MD2004/2004/U.S.) respectively. For the first immunization VLP's were emulsified in complete Freund's adjuvant. The following immunizations were formulated in incomplete Freund's adjuvant. No adverse effects were observed after inoculation. Llama management, inoculation, and sample collection were conducted by trained personnel under the supervision of a veterinarian and in accordance with approved protocols. Serum and blood samples were taken at days 0, 4 and 7 after each inoculation.

The antibody responses to NoV in serum during the time course of immunization were monitored by ELISA. To evaluate the effector B-cell response, an ELISPOT assay determining the number of NoV-specific antibody-secreting cells was performed at 4 and 7 days post each inoculation.

NoV VLP ELISA:

ELISA was performed as disclosed previously (Bok et al., Proc Natl Acad Sci U.S.A. 108(1): 325-30, 2011) with modifications for llama serum, as described below: 96 flat bottom well polyvinyl microtiter plates (Maxisorp, NUNC, Denmark) were coated with 50 µl/well of NoV VLP's overnight at 4° C. (Norwalk or MD2004 VLPs were used at a concentration of 1 µg/ml in Carbonate Buffer pH 9.6). The plates were washed with 0.05% Tween 20-PBS, and then were blocked with 200 µl of skim milk 5% in PBS for 1 hr, 37° C. After washing with 0.05% Tween 20-PBS, 50 µl of each serum sample four-fold dilution were added beginning with 1:50 in 1% skim milk-PBS. Samples were run in duplicate wells and incubated at 37° C. during 2 hours. The plates were washed with 0.05% Tween 20-PBS and a peroxidase-labeled anti-Llama IgG (Bethyl Labs, Inc., Montgomery, Calif.) at a 1:1,500 dilution in 1% skim milk-PBS was added to the plates, 50 µl/well. After 1 hour incubation at 37° C. the plates were washed with 0.05% $Tween_{20}$-PBS and then the assay was developed with commercial ABTS[2,2azinobis(3-ethylbenzthiazolinesulfonicacid)]/$H_2O_2$ substrate: 100 µl/well. The absorbance at 405 nm was read in an ELISA reader (Multiskan EX, Thermo scientific, U.S.A.).

NoV VLP ELISPOT:

Antibody secreting cells (ASC) in the peripheral blood of the inoculated llama was adapted from previous ELISPOT assays conducted for Rotavirus (Garaicoechea et al., J Virol 82(19): 9753-64, 2008). Briefly, 96-well Maxisorp ELISA plates with flat bottom were coated with NoV VLPs diluted in PBS (100 ng/well), overnight at 4° C. Suspensions of mononuclear cells derived from peripheral blood of the inoculated llamas were added to quadruplicate wells in ten fold dilutions, starting with $1 \times 10^6$ cells/well (e.g., $1 \times 10^6$, $1 \times 10^5$, $1 \times 10^4$, and $1 \times 10^3$ cells per well). After centrifugation at 500×g for 5 min, plates were incubated for 12 to 14 h at 37° C. in 5% $CO_2$. The plates were washed with PBS-0.05% Tween 20 to remove adherent cells, and the antibody spots were developed by adding a peroxidase-labeled goat anti-llama immunoglobulin G (IgG; H+L; Bethyl Labs, Inc., Montgomery, Calif.) at a 1/1,500 dilution for 2 h at 37° C., and after washing the plate the assay was developed with 50 µl l of a tetramethylbenzidine membrane peroxidase (TMB) substrate system (KLP, Maryland, U.S.A.).

$V_HH$ Library Production:

Two $V_HH$ libraries were developed from the blood of the two immunized llamas. From the llama immunized with VLPs of NoV MD2004 (GII.4) 300 ml of blood were taken four days after the third dose and 300 ml of blood four days after the fourth dose. From the other llama immunized with VLPs of NoV Norwalk (GI.1), 450 ml of blood were taken 4 days after the third dose. Mononuclear cells were extracted by Ficoll-Paque (Invitrogen, USA) gradient centrifugation, pelleted, frozen in liquid nitrogen, and then kept at 80° C. until the moment of use. The total RNA was extracted by using a commercial RNA extraction kit (Nucleospin RNA L; Macherey Nagel), yielding 300 µg of RNA for the Norwalk llama and 420 µg of RNA for the MD2004 llama. Subsequently, first-strand cDNA was synthesized from the total RNA by using MMLV Reverse Transcriptase (RT) (Promega), with random primers (Invitrogen) according to the manufacturer instructions. For each 20 µl reaction, 10 µg of total RNA was added. The V$_H$H-repertoire was PCR amplified from the total RNA for each llama, using the four combinations of two forward primers and two reverse primers to amplify the different V$_H$H subfamilies of short-hinge and long-hinge. The primers contained the restriction sites for further cloning steps: VH1b-SfiI (shf): 5' GCT GGA TTG TTA TTA CTC GCG GCC CAG CCG GCC ATG GCC CAG GT(GC) (AC)A(AG) CTG CAG SAG TCW GG 3' (SEQ ID NO: 35), Lam07-NotI (shr): 5' GAT GGT GAT GAT GAT GTG CGG CCG CGC TGG GGT CTT CGC TGT GGT GCG 3' (SEQ ID NO: 36), VH6b-SfiI (lhf): 5' CGT GGA TTG TTA TTA TCT GCG GCC CAG CCG GCC ATG GCC GAT GTG CAG CTG CAG GCG TCT GG(AG) GGA GG 3' (SEQ ID NO: 37), Lam08-NotI lhr: 5' GAT GGT GAT GAT GAT GTG CGG CCG CTG GTT GTG GTT TTG GTG TCT TGG 3' (SEQ ID NO: 38). PCR amplification products were purified, restriction digested, and cloned into the SfiI and NotI sites of the phagemid vector pAO-Lib (Garaicoechea et al., J Virol 82(19): 9753-64, 2008), a modified version of pHEN4 (Arbabi Ghahroudi et al., FEBS Lett 414(3): 521-6, 1997) carrying a long irrelevant sequence that is removed upon V$_H$H insertion in order to slow down the potential propagation of vector without a V$_H$H insert. Ligated material was transformed into *Escherichia coli* TG1 cells by electroporation. Colonies were harvested by scraping in culture medium, washed and stored at −80° C. in LB medium supplemented with glycerol (50% final concentration).

Enrichment in V$_H$H of Interest:

The V$_H$H libraries were infected with M13K07 helper phages (Invitrogen), and phage particles expressing the V$_H$H repertoire were rescued and precipitated with polyethylene glycol as described previously (Marks et al. J Mol Biol 222(3): 581-97, 1991). Enrichment in specific binders was performed using the phage display technology by two rounds of in vitro selection, i.e.by the so-called "biopanning" Briefly, Maxisorp immunoplates (NUNC) were coated overnight at 4° C. with NoV VLPs from Norwalk or from MD2004 strains (100 μg/well) in carbonate buffer pH 9.6. After a blocking step with skim milk 5% in PBS, phages from each library were added to the plates according to the different biopanning strategies and incubated for 1 hour at room temperature. Two strategies of selection were performed, one in which phages were incubated with the homologous VLPs, and the other strategy that had an additional step in which phages were incubated with the heterologous VLPs in order to subtract the cross reactive phages and the unbound phages were then incubated with the homologous VLPs. The second strategy was performed to enhance specificity and avoid selection of cross reactive V$_H$Hs between both genogroups. After incubation, the plates were washed with PBS-Tween 0.05% and bound phage particles were eluted with 100 mM triethylamine (pH 10.0) and immediately neutralized with 1M Tris (pH 7.4). The eluted phages were used to infect exponentially growing TG1 cells. After the second round of biopanning, individual colonies from 200 clones for NV and 200 clones for MD2004 NoV VLPs, were grown, and the corresponding V$_H$H clones were analyzed by phage ELISA for specificity to NoV GI.1 (Norwalk) and NoV GII.4 (MD2004). Finally, a third biopanning strategy using polyvinyl ELISA plates coated with the VLPs diluted in PBS pH 7.4 was also conducted for the GII.4 library.

Screening for GI.1 and GII.4 Specific V$_H$H Fragments by Phage ELISA:

Phages displaying the selected V$_H$H were produced by the individual TG1 *Escherichia coli* clones as previously described (Conrath et al., Antimicrob Agents Chemother 45(10): 2807-12, 2001). ELISA plates were coated overnight with 100 ng/well of NoV VLP of Norwalk strain or MD2004 strain or blank. After the coating step, all plates were blocked with 5% skim milk in 0.5% Tween20-PBS. Phages from each clone were added to wells coated with the different NoV VLPs and blank, and plates were incubated at room temperature for 2 hours. The assay was developed using a 1/5,000 dilution of a monoclonal antibody anti-M13p8 (Amersham/Pharmacia Biotech) and then a 1/2,000 dilution of an anti-Mouse IgG conjugated with peroxidase (KPL), followed by the addition of /ABTS/H$_2$O$_2$ as a substrate/chromogen reagent.

Expression and Purification of Recombinant V$_H$H:

V$_H$H cDNA of 11 clones that scored positive in phage ELISA for NoV VLPs of NV strain (GI.1) or MD2004 strain (GII.4) were subcloned using the restriction enzymes SfiI and NotI into the expression vector pHEN6 (Conrath et al., Antimicrob Agents Chemother 45(10): 2807-12, 2001), which provides a pelB targeting sequence for the periplasm and a C-terminal His6 tag. Production of recombinant monovalent V$_H$H was performed in shaker flasks by growing cells in Terrific Broth supplemented with ampicillin (Sambrook and Russell, Molecular Cloning: A Laboratory Manual, Cold Spring Harbor Laboratory, 3rd edition, 2001). *E. coli* XL1-Blue cells were freshly transformed with the different plasmid constructs and a culture from single colony for each V$_H$H was grown at 37° C. and 250 rpm. V$_H$H expression was then induced with 1 mM IPTG [isopropyl-D-thiogalactopyranoside] for 16 h at 28° C. After the cells were pelleted, the periplasmic proteins were extracted by osmotic shock (Skerra and Pluckthun Science 240(4855): 1038-41, 1988). The V$_H$H were purified from this periplasmic extract by using a High-Trap HP Ni-chelating column (Amersham Biosciences).

The V$_H$H nucleotide sequences of the obtained V$_H$H clones were aligned by ClustalW with Mega 6.06 and the alignment was edited with BioEdit.

NoV VLPs Detection by V$_H$H in ELISA:

Briefly, 96 well U bottom polyvinyl plates Dynatech (Nunc, Thermo, EEUU), were coated overnight (ON) at 4° C. with 100 ng of purified VLPs/well diluted in 50 μl of PBS pH 7.4. Wells incubated with PBS alone were used as a negative control for V$_H$H binding. After washing the plates with PBS pH 7.4 0.1% Tween20, they were blocked with 200 μl of skim milk 5% in PBS pH 7.4 0.1% Tween20, for 1 hour at 37° C. Then 50 μl/well with the corresponding V$_H$H dilution in PBS pH 7.4 5% skim milk were added and the plates were incubated for 2 hours at room temperature. After washing the plates, 50 μl of anti-V$_H$H serum made in rabbit and diluted 1:8,000 in PBS 5% skim milk, were added to each well and the plates were incubated for 1 hour at room temperature. The plates were washed with 0.05% Tween 20-PBS and the binding of antibodies to the VLP antigen was detected with horseradish peroxidase (HRP)-conjugated goat anti-rabbit IgG (KPL, Gaithersburg, Md.), 1:2,000 dilution in 1% skim milk-PBS, 50 μl/well. After 1 hour of incubation at 37° C., the plates were washed and the assay was developed with the chromogen system ABTS/H$_2$O$_2$ Absorbance at 405 nm was measured. The cut off was defined as twice the absorbance obtained in the blank wells. For the determination of the V$_H$Hs detection limit for GI.1 (Norwalk and Norovirus 2007) and GII.4 (MD2004 and MD145) VLPs, serial ten-fold dilutions were tested from 500 ng/well to 0.005 ng/well of V$_H$H. To test the ability of each V$_H$H to recognize a panel of VLPs from different NoV strains, the fixed amount of 20 ng of V$_H$H/well was selected.

To evaluate the specificity of the $V_HH$ against the different domains of VP1, the VLP NV S domain/MD2004 P domain chimera and the VLP MD2004 S domain/NV P domain chimera previously described were used (Parra et al., J Virol 86(13): 7414-26, 2012). The $V_HH$ were tested in this assay at the fixed concentration of 20 ng/50 μl per well.

Western Blot Analysis:

The reactivity of each $V_HH$ with the MD2004 VLPs or with the Norwalk VLPs was analyzed by Western blot. For this assay, 1.5 μg of VLPs were mixed with NOVEX® 2× Tris-Glycine SDS loading buffer (Invitrogen), and after boiling during 5 min at 95° C., the samples were analyzed with polyacrylamide gel electrophoresis (SDS-PAGE) NUPAGE® Novex 4-12% (Invitrogen). The proteins were blotted onto a nitrocellulose membrane using the IBLOT® Dry Blotting System (Invitrogen). The membranes were blocked with PBS 5% skim milk for 2 h at RT. Each $V_HH$ (5 μg/ml) was adsorbed overnight at 4° C. and the binding was detected with rabbit anti $V_HH$ antiserum 1:1,000 1 hour at room temperature and then Alkaline Phosphatase-conjugated goat anti-rabbit IgG (1:2,000, 1 hour at room temperature) and the NBT-BCIP Chromogen system.

Blocking of NoV VLP-Binding to Synthetic HBGA by $V_HHs$:

Neutravidin coated plates (PIERCE®) were used for this assay following the manufacturer instructions. Plates were coated with biotinylated carbohydrates H1 (for NV) or H3 (for MD145) 1 μg/well. A total of 150 ng of VLPs diluted in 100 μl of buffer were pre-incubated with 400, 200, 100, 50, 25 and 0 ng of $V_HH$ for 1 hour at room temperature. The 150 ng of the pre-incubated VLPs were added to each well of the carbohydrate-coated plates and incubated for 1 h. The binding of captured VLPs was determined by incubation with guinea pig hyperimmune serum (1:10,000 dilution), followed by incubation with HRP-conjugated goat anti-guinea pig immunoglobulin G (1:2,000 dilution; KPL) and the peroxidase substrate ABTS (KPL). All incubations were performed at room temperature. Absorbance at 405 nm was measured. The percent control binding was defined as the binding level in the presence of antibody pretreatment divided by the binding level in the absence of antibody pretreatment multiplied by 100. Mean % control binding present the results of two replicates for each dilution tested. An antibody was designated as a "blockade" antibody for a VLP if at least 50% of control binding (EC50) was inhibited by 2 μg/ml antibody or less. Blockade data were fitted and EC50 values calculated using sigmoidal dose response analysis of non-linear data in GraphPad Prism 5 (available on the internet, graphpad.com).

As positive controls for the blocking of the binding of the VLPs, the monoclonal antibody D8 anti-Norwalk and the monoclonal antibody C9 anti-MD145 were included.

VLP-Pig Gastric Mucin Ligand-Binding Antibody Blockade Assays:

Pig Gastric Mucin Type III (PGM) (Sigma Chemicals) was used as a substrate for NoV VLP antibody-blockade assay as previously described. Briefly, PGM was resuspended in PBS at 5 mg/ml and coated onto 96 well U bottom polyvinyl plates Dynatech (Nunc, Thermo, USA) at 10 μg/ml in PBS for 4 hours. Plates were then blocked ON at 4° C. in 5% dry milk in 0.05% Tween$_{20}$-PBS. Norwalk and MD 2004VLPs (0.5 mg/ml) were pretreated with decreasing concentrations of each $V_HH$ (2-fold dilutions from 8 μg/ml to 0.125 ug/ml) for 1 hour. One hundred μl of VLPs-$V_HH$ mix were transferred to the PGM coated plates and incubated for 1 hour. Bound VLPs were detected by specific hyperimmune sera made in guinea pig, followed by anti-guinea pig IgG-HRP (KLP). ABTS/$H_2O_2$ was used as chromogen/substrate solution. All incubations were performed at room temperature and absorbance at 405 nm was measured. Mean % control binding, EC50 and criteria for determination of a blockade $V_HH$ were calculated as described above.

VLP-Saliva Ligand-Binding Antibody Blockade Assays:

For this assay saliva positive for Ly antigen collected from a secretor individual was used. Saliva was boiled (95° C.) for 10 minutes immediately after collection, centrifuged for 5 minutes at 13000×g and the supernatants stored at −20° C. until used. ELISA 96 well U bottom polyvinyl plates Dynatech (Nunc, Thermo, EEUU) were coated with 100 μl/well of a 1/400 saliva dilution in 50 μM carbonate-bicarbonate buffer, pH 9.6. The plate was incubated overnight at 37° C. in a wet atmosphere. In parallel, serial two-fold dilutions of $V_HH$ starting from 8 ug/ml were mixed with 1.5 ug/ml of NoV VLP Norwalk and MD145 and incubated for 1h at 37° C. After 6 washes and a blocking step with 5% dry milk/0.05% Tween$_{20}$-PBS, 50 ul of each $V_HH$-VLP mixture was transferred to the reaction plate, in duplicate. The assay was developed using a specific polyclonal antiserum made in guinea pig (1:10,000) followed by a peroxidase labeled anti-guinea pig IgG (1:2,000) and ABTS/$H_2O_2$ as substrate chromogen (KPL), 100 μl per well. Absorbance at 405 nm was measured. Mean % control binding, EC50 and criteria for determination of a blockade $V_HH$ were calculated as described above.

Hemagglutination Inhibition Assay (HAI):

This assay was performed using red blood cells (RBC) that had the property of hemagglutinating the different VLPs tested: MD2004, MD145, NV and P7-587. Several human blood samples were tested for hemagglutination property to the four selected VLPs. Finally 0 Rh− blood samples were selected to perform the assay with GI.1 VLPs and B Rh+ was selected for hemagglutination of GII.4 VLPs. The samples, RBC and buffers were prepared as described elsewhere (Hutson et al., J Infect Dis 185(9): 1335-7, 2002). The working solution of RBC was prepared adding 0.75 ml of RBC pellet to 100 ml of physiologic saline solution pH6.2. The $V_HH$ samples were diluted in PBS-physiologic saline solution pH 5.5 from 6.25 μg/25 μl to 0.0025 μg/25 μl in two fold serial dilutions and 25 μl of each dilution were added in duplicates to each well. Four to eight hemagglutination units (HU) of VLPs were added to each sample dilution and the plates were incubated for 1 hour at room temperature. Then, 50 μl of the RBC dilution 0.75% in physiologic saline solution pH 6.2 were added to each well and the plates were incubated for 2 hours at 4° C. and finally the presence or absence of hemagglutination was observed. The HAI titer of each $V_HH$ was defined as the lowest antibody concentration that completely prevented NoV VLP-induced hemagglutination by visualization.

Blocking Between $V_HHs$ and Llama Hyperimmune Serum for NoV VLP Binding:

Briefly, 96-well polyvinyl microtiter plates (Thermo) were coated with 12.5 ng/well of VLPs (from Norwalk or MD2004 NoV strains) and incubated overnight at 4° C. Wells were washed with 0.05% Tween$_{20}$-PBS and blocked with 5% dry milk-PBS for 1 h at RT.

In the first assay, llama hyperimmune serum specific for the corresponding VLP, was added to each well diluted 1/500 and incubated for 1 hour at room temperature. After washing the plates, 6.25 ng of each $V_HH$ were added to the wells in duplicates. The same assay without blocking with the hyperimmune antisera was used as control. Then the plates were washed and incubated with anti His MAb (Qiagen) 10 ng/well and HRP-conjugated anti-mouse immunoglobulin G (1/2,000) (KPL). The signal was developed with ABTS/$H_2O_2$ and the absorbance at 405 nm was measured.

In another assay, each $V_HH$ or a pool of all $V_HHs$ in a concentration of 250 µg/ml were added to each well and incubated for 1 hour at room temperature, control wells without blocking $V_HHs$ were included. After washing the plates, two fold serial dilutions of the corresponding llama hyperimmune serum from 1/1,000 to 1/2,000,000 was added in duplicates. The assay was developed with HRP-conjugated anti-llama IgG (1/2,000) (Bethyl). The signal was developed with ABTS/$H_2O_2$ and the absorbance at 405 nm was measured.

Immunofluorescence Assay to Evaluate Competition Between the Different $V_HHs$:

Vero cells were plated in 96-well plates at 50,000 cells/well and incubated for 24 h at 37° C., 5% $CO_2$. The cells were then infected with a modified vaccinia virus expressing bacteriophage T7 RNA polymerase (MVA-T7) at a multiplicity of infection (MOI) of 5 PFU/cell for 1 h at 37° C., 5% $CO_2$. After infection, cells were transfected with 400 ng/well of each DNA construct expressing Norwalk or MD2004 VP1 in the presence of Lipofectamine 2000 (Invitrogen) following the manufacturer's recommendations. Transfected cells were incubated for 24 h and then fixed with cold methanol for 10 min. The plates were blocked using10% normal goat serum (KPL), ON at 4° C. Fifty microliter containing 10 µg/well of each unlabeled $V_HH$ and 1 µl of ALEXA FLUOR® 568 (Molecular Probes-Invitrogen, Carlsbad, Calif.) labeled $V_HH$ (1 mg/ml) was added to the fixed cells in duplicates and incubated for 2 h at room temperature.

Epitope Mapping of the $V_HH$ that Recognized a Linear Epitope Using a Peptide Library:

For this assay, a peptidic library of 67 peptides corresponding to the P domain of the VP1 amino acid sequence from NoV Toronto strain was synthetized. The peptides were 17 amino acids long, with 5 amino acids overlapping with the previous and the next peptide of the sequence. Neutravidin coated plates (PIERCE®) were used for this assay. The plates were coated with each biotinylated peptide in duplicates (2 µl of peptide/100 µl of PBS 0.1% BSA per well) overnight at 4° C. Then, after washing the plates, 100 ng/well of 7.5 $V_HH$ were added and the plates were incubated for 2 hours at room temperature. The plates were washed and incubated with rabbit anti-$V_HH$ serum (1/8,000) and HRP-conjugated goat anti-rabbit immunoglobulin G (1:2,000) (KPL). The signal was developed with ABTS/$H_2O_2$.

Site-Directed Mutagenesis for Epitope Mapping of $V_HH$ 16.

The pCI-MD2004 vector described previously (Parra et al., J Virol 86(13): 7414-26, 2012) was mutated using a Quick-change site-directed mutagenesis kit (Stratagene) and complementary forward and reverse primers which carried the nucleotide mutations. The restriction enzyme DpnI (10 U/µl) was used to digest the parental DNA. Each of the mutated products was transformed into Epicurian Coli XL1-Blue supercompetent cells (Stratagene). Transformed cells were grown overnight in LB plates with carbenicillin (50 µg/ml), and individual colonies were used for plasmid amplification. The resulting plasmids were subjected to sequence analysis to verify the entire VP1 coding region and confirm the presence of the introduced mutations. The mutation sites were selected according to the different surface amino acids between MD2004 and MD145 strains.

The ability of $V_HH$ 16 to recognize the mutated VP1 was tested by immunofluorescence and by ELISA.

Briefly, MD2004 mutant VP1 were expressed in Vero cells as described above and after the incubation with $V_HH$ 16 the assay was developed with rabbit anti-$V_HH$ polyclonal serum and goat anti-rabbit IgG(H+L) conjugated with Alexa Fluor 488 (Molecular Probes-Invitrogen, Carlsbad, Calif.). The plate was observed under the immunofluorescence microscopy. A $V_HH$ that detected MD145 strain was included as positive control.

MD2004 mutant VLPs were expressed and purified as previously described (Parra et al., J Virol 86(13): 7414-26, 2012) and detected by ELISA as described above.

Bioinformatics Analyses:

Nucleotide sequences from the prototype strains were downloaded from GENBANK® and aligned by using the translated amino acid sequences. Phylogenetic trees were constructed using the Kimura two-parameter model as a nucleotide substitution model and a neighbor-joining (NJ) algorithm as implemented in MEGA v4.0 (55). The solved structure of the P domain of VA387 virus (GII.4) in complex with carbohydrate (Protein Data Bank [PDB] accession number 2OBT) was used to identify the residues involved in binding with MAbs and was visualized by using MacPyMol (DeLano Scientific LLC).

Example 2

Llama Immunization

The antibody (Ab) response to immunization is depicted in FIG. 1. Both llamas were seronegative for Ab to human NoV GI.1 and GII.4 at the beginning of the immunization. After 14 days post the first dose both llamas developed strong antibody responses to the homologous VLP. Cross-reactive antibody responses were also detected. The llama immunized with Norwalk GI.1 NoV VLPs developed high ELISA Ab titer reaching a plateau at 1:100,000 serum dilution. A cross reactive antibody (Ab) response to MD2004 GII.4 VLPs of lower magnitude, reaching a plateau at 1:10,000 serum dilution was also observed (FIG. 1a).

Figure 1B:
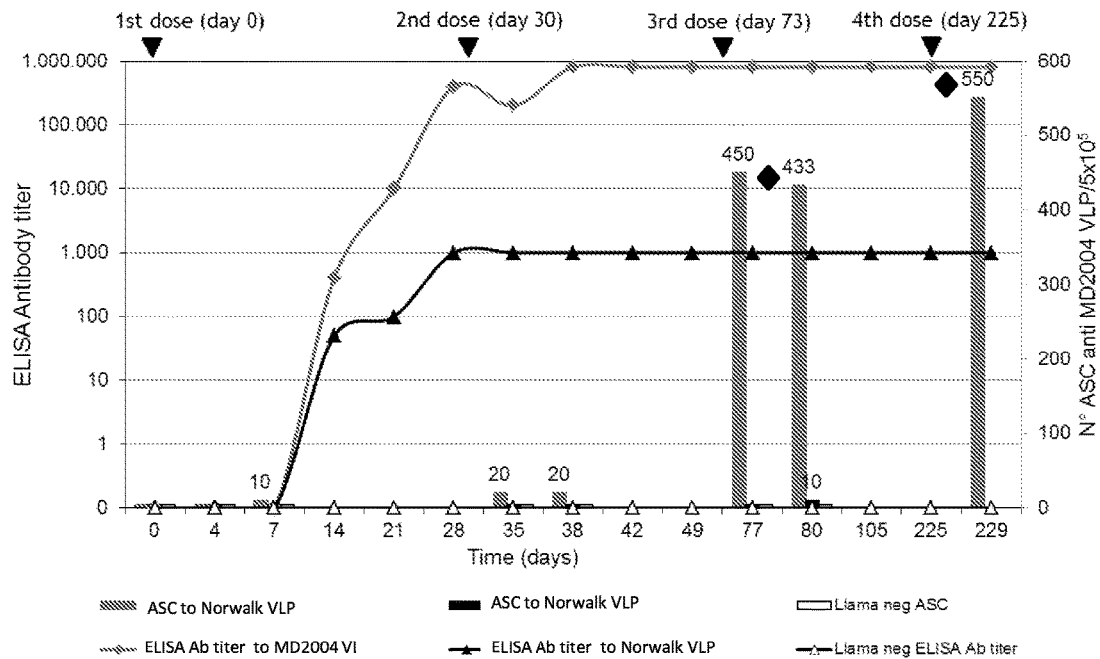

The llama immunized with MD2004 GII.4 NoV VLPs developed a strong Ab response by ELISA to the homologous antigen reaching a plateau at 1:800,000 serum dilution. This llama also showed seroconversion to Norwalk GI.1 VLPs but of lower magnitude reaching a plateau at 1:1,000 serum dilution (FIG. 1b).

Antibody secreting cell (ASC) responses were successfully assessed for Norwalk and MD2004 NoV VLPs. These results showed the presence of high numbers of ASC to the homologous VLP and around of 1-2% of ASC with cross reactivity (FIGS. 1a and b).

After confirming optimal Ab titer and ASC responses, both llamas received a third immunization and were bled 4 days after the third dose. Additionally, the llama immunized with MD2004 VLPs received a fourth dose of antigen and was also bled four days later. A total of 450 ml of blood was obtained from the llama immunized with Norwalk NoV VLPs yielding $5.91 \times 10^8$ mononuclear cells, while 600 ml of blood extracted from the llama immunized with MD2004 NoV VLP yielded $6.6 \times 10^8$ mononuclear cells. From the processed RNA, two $V_HH$ phage display libraries containing $4.2 \times 10^8$ clones for Norwalk NoV and $1.0 \times 10^8$ clones for MD2004 NoV were generated. Both $V_HH$ libraries possessed optimal size (in the order of $10^8$) according to the literature (Muyldermans, Annu Rev Biochem 82: 775-97, 2013).

Example 3

Phage Display Selection of $V_HH$ Specific to Norwalk or MD2004 NoV Strains

To select phages displaying $V_HH$ specific for each NoV genogroup, two rounds of in vitro selection (biopanning) were performed using the homologous NoV VLPs as antigens. Furthermore, with the aim of obtaining highly specific $V_HHs$ to the immunization antigen, two round of an extra biopanning strategy were performed. The phages from each library were pre-incubated with the heterologous antigen to subtract the cross reactive clones and the unbound phages were then incubated with the homologous antigen. After the second round of biopanning, 96 clones for each sub-library (a total of 384 clones) were analyzed by phage ELISA.

Ninety out of 96 clones from the $V_HH$ library specific for Norwalk recognized Norwalk VLPs, when the library was enriched with the homologous VLP. In the second biopanning strategy, when cross reactive clones were previously subtracted with MD2004 VLPs and the library was then enriched in Norwalk specific clones, 32/96 phages recognized Norwalk VLP by phage ELISA.

For the MD2004 specific library, biopanned with the homologous antigen, 31/96 phages recognized MD2004 VLPs in phage ELISA. When a previous step of subtraction of cross reactive phages with Norwalk VLPs was performed, 44/96 clones recognized MD2004 VLPs. For all the tested phages, no reaction was observed for the blank plates nor for the plates coated with the VLP not used in the biopanning.

From the total positive clones obtained in each initial biopanning condition, the ones with the highest positive signal in phage ELISA were selected, subcloned, expressed and purified.

From these clones, 16 $V_HH$ and 2 VH with different amino acid sequences that were successfully subcloned, expressed in the pHEN6 expression vector and purified by his-tag, were chosen for further characterization experiments, 10 $V_HH$ derived from the Norwalk library while 6 $V_HHs$ and 2 VHs derived from the MD2004 library (Table 1).

TABLE 1

Selection of $V_HH$ for characterization

| Antigen of vaccination | Antigen of selection | Antigen detected by Phage ELISA | Clone | Ab type |
|---|---|---|---|---|
| Norwalk | Norwalk | Norwalk | 6.3 | $V_HH$ |
|  |  |  | 7.3 |  |
|  |  |  | 8.1 |  |
|  |  |  | 9.8 |  |
|  |  |  | 10.4 |  |
|  |  |  | 11.2 |  |
|  |  |  | 12.2 |  |
|  |  |  | 14.5 |  |
|  | Norwalk (-MD2004) | Norwalk | 13.2 H1 | $V_HH$ |
| MD2004 | MD2004 | MD2004 | 1.1 | $V_HH$ |
|  |  |  | 2.1 |  |
|  |  |  | 3.2 |  |
|  |  |  | 4.1 |  |

TABLE 1-continued

Selection of $V_HH$ for characterization

| Antigen of vaccination | Antigen of selection | Antigen detected by Phage ELISA | Clone | Ab type |
|---|---|---|---|---|
|  |  |  | 5.4 |  |
|  |  |  | 7.5 |  |
|  | MD2004 (-Norwalk) | MD2004 | 16 | VH |
|  |  |  | 19 |  |

The third biopanning strategy using polyvinyl plates coated with GII.4 VLPs in PBS pH 7.4 was conducted in a pH that improve the stability of the VLP in order to select $V_HHs$ to other native epitopes. From this condition 13 new clones were obtained.

The aligned sequences of the obtained $V_HH$ clones are shown in FIG. 8 and the CDR3 of the $V_HHs$ are detailed in Table 5.

TABLE 5

CDR3 sequences of the $V_HHs$

| $V_HH$ name | Amino Amino acid sequences of the CDR3* | NoV genogroup specificity | SEQ ID NO:* |
|---|---|---|---|
| 3.2 | NLKRRDLQARFGGY | GII | 1 |
| 4.1 | NLKRRDLQSRFGGY | GII | 2 |
| 5.4 | NLKRRDLQARFGGY | GII | 3 |
| P10 | NLKRRDLQARFGGY | GII | 4 |
| 19.1 | AKPRDFWYSPEFDF | GII | 5 |
| P3 | AKGVYGSRRSADFGS | GII | 6 |
| P4 | AKGVYGSRRSADFGS | GII | 7 |
| P5 | AKGVYGSRRSADFGW | GII | 8 |
| 7.5 | NANFQIIIRSGADYVRNY | GII | 9 |
| P15 | NANLQIHRDSSGDVRNV | GII | 10 |
| P2 | NANLQISRSEDGAYVVRNY | GII | 11 |
| P8 | NANLQFYRGGGSDVKNY | GII | 12 |
| 2.1 | AAAEFFSSGDPLPGMDY | GII | 13 |
| P12 | AAAEFLPTQRSPREYDY | GII | 14 |
| P14 | AASRRFWTAALNGADYPY | GII | 15 |
| P13 | NARDWSDGFDEY | GII | 16 |
| P9 | ASGPRANASIRRSGYNY | GII | 17 |
| 1.1 | TASEFLLHPPPPNQKYDY | GII | 18 |
| P1 | AARSRPAISTRRPDYFA | GII | 19 |
| P7 | AARRRVFSRAAAAYNY | GII | 20 |
| 16.1 | SRGVSGE | GII | 21 |
| 6.3 | YALIQTASTTWYRQY | GI | 22 |

TABLE 5-continued

CDR3 sequences of the V$_H$Hs

| V$_H$H name | Amino Amino acid sequences of the CDR3* | NoV genogroup specificity | SEQ ID NO:* |
|---|---|---|---|
| 7.3 | NANLGALLDY | GI | 23 |
| 8.1 | KRVRDVIGRPEL | GI | 24 |
| 9.8 | AAEVHPGDYGLTYMQSQYEYDY | GI | 25 |
| 10.4 | KVDSYTYGTDI | GI | 26 |
| 11.2 | KADGRRYSLNEY | GI | 27 |
| 12.2 | NIYYGGDYYYTGVKPNP | GI | 28 |
| 13.1 | AASKIRNDIYLNDYTWYQY | GI | 29 |
| 14.5 | AAHHITPTGSYYYSEPLPVDMVYDY | GI | 30 |

*The sequences presented are:
a) amino acids 96-109 of SEQ ID NO: 1;
b) amino acids 96-109 of SEQ ID NO: 2;
c) amino acids 96-109 of SEQ ID NO: 3;
d) amino acids 96-109 of SEQ ID NO: 4;
e) amino acids 97-110 of SEQ ID NO: 5;
f) amino acids 97-111 of SEQ ID NO: 6;
g) amino acids 97-111 of SEQ ID NO: 7;
h) amino acids 97-111 of SEQ ID NO: 8;
i) amino acids 96-112 of SEQ ID NO: 9;
j) amino acids 96-112 of SEQ ID NO: 10;
k) amino acids 96-114 of SEQ ID NO: 11;
l) amino acids 96-112 of SEQ ID NO: 12;
m) amino acids 97-113 of SEQ ID NO: 13;
n) amino acids 97-113 of SEQ ID NO: 14;
o) amino acids 97-114 of SEQ ID NO: 15;
p) amino acids 96-107 of SEQ ID NO: 16;
q) amino acids 97-113 of SEQ ID NO: 17;
r) amino acids 97-114 of SEQ ID NO: 18;
s) amino acids 97-113 of SEQ ID NO: 19;
t) amino acids 96-111 of SEQ ID NO: 20;
u) amino acids 96-102 of SEQ ID NO: 21;
v) amino acids 96-110 of SEQ ID NO: 22;
w) amino acids 95-104 of SEQ ID NO: 23;
x) amino acids 96-107 of SEQ ID NO: 24;
y) amino acids 100-110 of SEQ ID NO: 25;
z) amino acids 96-117 of SEQ ID NO: 26;
aa) amino acids 97-108 of SEQ ID NO: 27;
bb) amino acids 96-112 of SEQ ID NO: 28;
cc) amino acids 97-115 of SEQ ID NO: 29;
dd) amino acids 97-121 of SEQ ID NO: 30.

Example 4

V$_H$H Domain Specificity on the VP1 Protein and Western Blot Analysis

All the V$_H$Hs selected were directed to the P domain of VP1 (Table 2).

TABLE 2

Specificity of the V$_H$Hs to the P or S domain of VP1

|  | VHH GI.1 specific | | | | | | | | | | VHH GII.4 specific | | | | | | | |
|---|---|---|---|---|---|---|---|---|---|---|---|---|---|---|---|---|---|---|
| VLP | 6.3 | 7.3 | 8.1 | 9.8 | 10.4 | 11.2 | 12.2 | 13.1 | 14.5 | H1 | 1 | 2.1 | 3.2 | 4.1 | 5.4 | 7.5 | 16 | 19 |
| ChimMD2004/(S)-NV(P) | + | + | + | + | + | + | + | + | + | + | | | | | | | | |
| Chim NV(S)/MD2004(P) | | | | | | | | | | | | + | + | + | + | + | + | + |
| Norwalk 1968 | + | + | + | + | + | + | + | + | + | + | | | | | | | | |
| MD2004 | | | | | | | | | | | | + | + | + | + | + | + | + |
| Recognized Domain | P | P | P | P | P | P | P | P | P | P | P | P | P | P | P | P | P | P |

All V$_H$Hs, except clone 7.5, failed to recognize the NoV VLPs by WB, suggesting that they are directed to conformational epitopes of the P domain. In contrast clone 7.5 was able to recognize the VP1 of MD2004 strain (homologous) by WB as well as the VP1 of GII NoVs strains belonging to different genotypes (FIG. 9A-9B).

Example 5

V$_H$H Recognition of NoV VLPs from Different Years and Genotypes by ELISA

The purified V$_H$H were tested by ELISA against the NoV VLPs used in the immunization and biopanning and also with a panel of 26 VLPs representing different genogroups/genotypes of NoV (Table 3).

TABLE 3

Capacity of the V$_H$Hs of recognizing VLPs of different genotypes by ELISA

| Norovirusstrain | Year | Genotype | GI.1-specific VHH | | | | | | | |
|---|---|---|---|---|---|---|---|---|---|---|
| | | | 6.3 | 7.3 | 8.1 | 9.8 | 10.4 | 11.2 | 12.2 | 13.1 |
| Norwalk 1968 | 1968 | GI.1 | 0.50 | 0.50 | 1.00 | 0.50 | 0.50 | 1.00 | 1.00 | 2.00 |
| P7-587 | 2007 | GI.1 | 0.50 | 0.50 | 1.00 | 1.00 | 0.50 | 1.00 | 1.00 | – |
| Desert-Shield395 | 1990 | GI.3 | – | 0.50 | – | – | – | – | – | – |
| SzUG1 | 1997-99 | GI.5 | – | – | – | – | – | – | – | – |
| Hesse | 1997 | GI.6 | – | – | – | – | – | – | – | – |
| Hawaii | 1971 | GII.1 | – | – | – | – | – | – | – | – |
| Snow Mountain | 1976 | GII.2 | – | – | – | – | – | – | – | – |
| Henryton | 1971 | GII.2 | – | – | – | – | – | – | – | – |
| Toronto 24 | 1991 | GII.3 | – | – | – | – | – | – | – | – |
| CHDC2005 | 2005 | GII.3 | – | – | – | – | – | – | – | – |
| CHDC5261 | 1990 | GII.3 | – | – | – | – | – | – | – | – |
| CHDC4031 | 1988 | GII.3 | – | – | – | – | – | – | – | – |
| Maizuru2000 | 2000 | GII.3 | – | – | – | – | – | – | – | – |
| Aus2001 | 2001 | GII.3 | – | – | – | – | – | – | – | – |
| Aus2007 | 2007 | GII.3 | – | – | – | – | – | – | – | – |
| Aus 2008 | 2008 | GII.3 | – | – | – | – | – | – | – | – |
| CHDC32 | 1976 | GII.3 | – | – | – | – | – | – | – | – |
| CHDC4871 | 1977 | GII.4 | – | – | – | – | – | – | – | – |
| Rockville | 2012 | GII.4 | – | – | – | – | – | – | – | – |
| MD2004 | 2004 | GII.4 | – | – | – | – | – | – | – | – |
| MD145 | 1997 | GII.4 | – | – | – | – | – | – | – | – |
| HS191 | 2001 | GII.4 | – | – | – | – | – | – | – | – |
| Bethesda | 2012 | GII.6 | – | – | – | – | – | – | – | – |
| DC119 | 1978 | GII.7 | – | – | – | – | – | – | – | – |
| M7 | 1999 | GII.14 | – | – | – | – | – | – | – | – |
| St. Cloud 624 | 1998 | GIV.1 | – | – | – | – | – | – | – | – |

| Norovirusstrain | GI.1-specific VHH | | GII.4-specific VHH | | | | | | |
|---|---|---|---|---|---|---|---|---|---|
| | 14.5 | H1 | 1 | 2.1 | 3.2 | 4.1 | 5.4 | 7.5 | 16 | 19 |
| Norwalk 1968 | 0.50 | 1.00 | – | – | – | – | – | – | – | – |
| P7-587 | 0.50 | – | – | – | – | – | – | – | – | – |
| Desert-Shield395 | – | – | – | – | – | – | – | – | – | – |
| SzUG1 | – | – | – | – | – | – | – | – | – | – |
| Hesse | – | – | – | – | – | – | – | – | – | – |
| Hawaii | – | – | – | – | – | 1.00 | 1.00 | 1.00 | – | 1.00 |
| Snow Mountain | – | – | – | – | – | 2.00 | 2.00 | 2.00 | – | 2.00 |
| Henryton | – | – | – | – | – | 1.00 | 2.00 | 1.00 | – | 2.00 |
| Toronto 24 | – | – | – | – | – | + | + | + | – | + |
| CHDC2005 | – | – | – | – | – | + | + | + | – | + |
| CHDC5261 | – | – | – | – | – | + | + | + | – | + |
| CHDC4031 | – | – | – | – | – | 2.00 | 0.50 | 1.00 | – | 0.50 |
| Maizuru2000 | – | – | – | – | – | + | + | + | – | + |
| Aus2001 | – | – | – | – | – | + | + | + | – | + |
| Aus2007 | – | – | – | – | – | + | + | + | – | + |
| Aus 2008 | – | – | – | – | – | + | + | + | – | + |
| CHDC32 | – | – | – | – | – | + | + | + | – | + |
| CHDC4871 | – | – | 0.25 | – | 0.50 | 0.50 | 0.50 | 2.00 | – | 1.00 |
| Rockville | – | – | 0.25 | 0.25 | 0.50 | 1.00 | 0.50 | 0.50 | – | 2.00 |
| MD2004 | – | – | 0.50 | 0.50 | 2.00 | 2.00 | 1.00 | 0.50 | 0.50 | 2.00 |
| MD145 | – | – | 0.50 | 8.00 | 1.00 | 2.00 | 4.00 | 0.50 | – | 4.00 |
| HS191 | – | – | 1.00 | 0.50 | 0.50 | 0.50 | 0.25 | 2.00 | – | 1.00 |
| Bethesda | – | – | – | – | 0.50 | 2.00 | 1.00 | 1.00 | – | 2.00 |

TABLE 3-continued

Capacity of the $V_HH$s of recognizing VLPs of different genotypes by ELISA

| | | | | | | | | | | |
|---|---|---|---|---|---|---|---|---|---|---|
| DC119 | — | — | — | — | — | 0.50 | 0.50 | 1.00 | — | 1.00 |
| M7 | — | — | — | — | — | — | — | 1.00 | — | — |
| St. Cloud 624 | — | — | — | — | — | — | — | — | — | — |

Numbers detailed in the table represent the minimum concentration of $V_HH$ (ng/well) able to recognize 100 ng of purified VLPs by ELISA.

The ten $V_HH$s obtained from the Norwalk library were able to react with the homologous GI.1 VLP. All clones except 13.1 and H1 were able to detect P7-587GI.1 strain. Only clone 7.3 was able to recognize the Desert Shield 395 strain that belongs to GI.3 genotype. None of these $V_HH$ reacted with GI.5 and GI.6 strains or with GII and GIV NoVs (Table 3).

The eight $V_HH$s derived from the GII.4 MD2004 library were able to detect the homologous VLP with high affinity by ELISA. These $V_HH$s displayed a great variety of recognition patterns. Clone 16 reacted specifically with GII.4 MD2004 strain. Clone 2.1 detected with high affinity 3 out of 5 GII.4 strains, clone 1 reacted with all GII.4 strains, clone 3.2 reacted with GII.4 strains and also detected GII.6 strain. Clones 4.1, 5.4 and 19 were able to react with GII NoVs strain belonging to genotypes 1, 2, 3, 6 and 7. Finally, the clone 7.5, directed to a linear epitope, recognized all the GII VLPs tested by ELISA (Table 3).

The clone 13 and H1, specific for Norwalk and clone 16 specific for MD2004 (Table 3)—the antigens used for llama immunization-were selected from subtractive biopanning strategies (Table 1). The 13 clones obtained in the third biopanning strategy were able to recognized GII.4 MD 2004 by ELISA with high affinity.

Using this panel of recombinant NoV VLPs covering a broad range of genotypes within both genogroups, the $V_HH$ tested were shown to be either genogroup specific, genotype specific, or strain specific. The different patterns of cross-reactivity were similar in nature to the observed behavior of conventional monoclonal antibodies (Li et al., Virus Res 151(2): 142-7, 2010; Yoda et al., BMC Microbiol 1: 24, 2001; Yoda et al., J Clin Microbiol 41(6): 2367-71, 2003; Parker et al., J Virol 79(12): 7402-9, 2005; Batten et al., Virology 356(1-2): 179-87, 2006; Oliver et al., J Clin Microbiol 44(3): 992-8, 2006; Shiota et al., J Virol 81(22): 12298-306, 2007; Almanza et al., J Clin Microbiol 46(12): 3971-9, 2008; and Parra et al., Vaccine 30(24): 3580-6, 2012).

Example 6

Figure 2A:
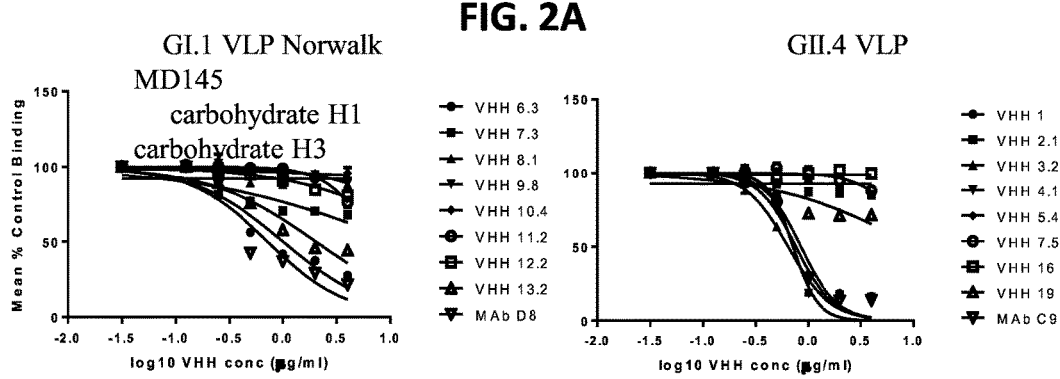
FIGS. 2A-2C. Blockade assays. Surrogate virus neutralization tests were performed using different sources of carbohydrates.
Figure 2B:
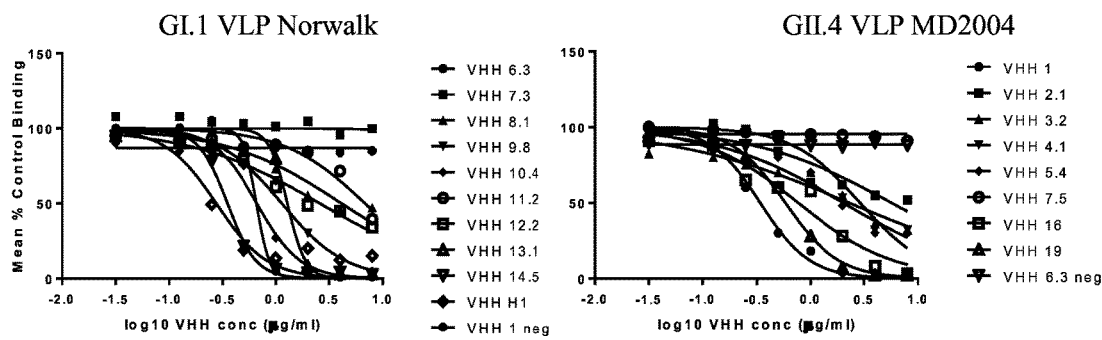
Figure 2C:
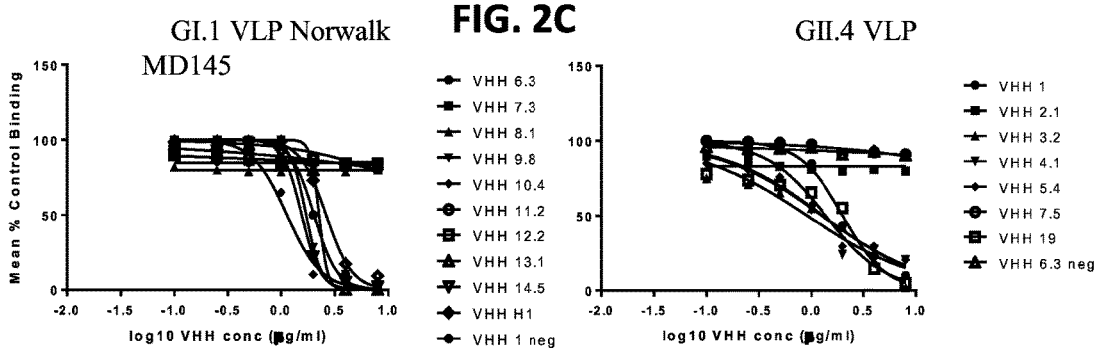
Figure 3A:
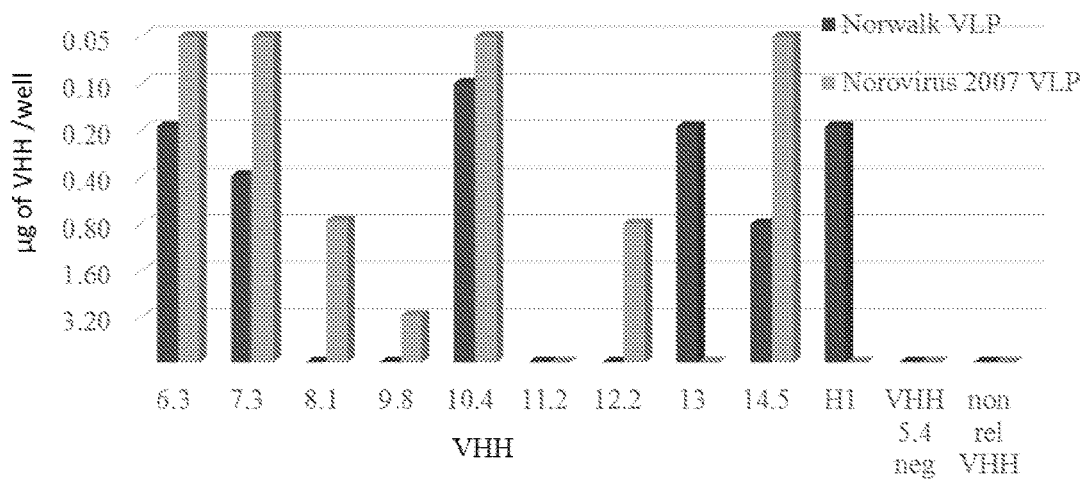
FIGS. 3A-3B. Hemagglutination inhibition assay. The HAI titer of each $V_HH$ was defined as the lowest antibody concentration that completely prevented NoV VLP-mediated hemagglutination of human RBC. Norwalk or Norovirus 2007 GI.1 VLPs hemagglutinated 0 Rh− RBC (FIG. 3A, GI.1 VLPs); MD2004 or MD145 GII.4 VLPs hemagglutinated B Rh+ (FIG. 3B, GII.4 VLPs).
Figure 3B:
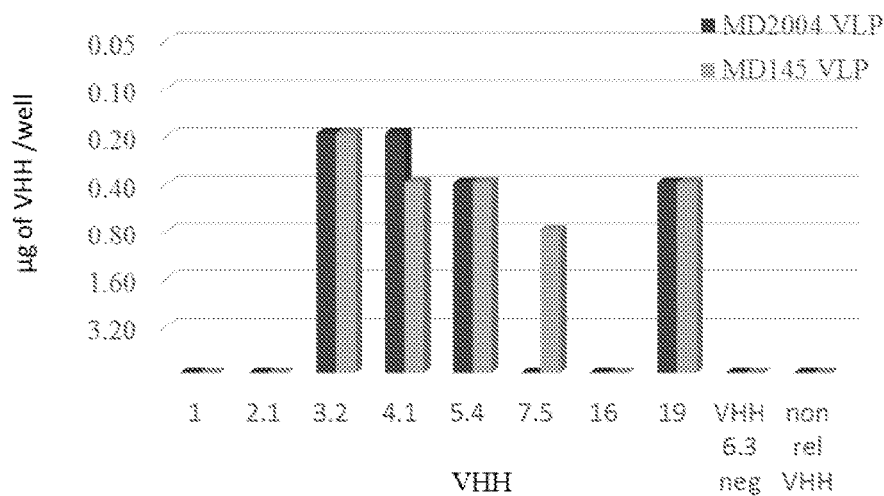
Figure 4A:
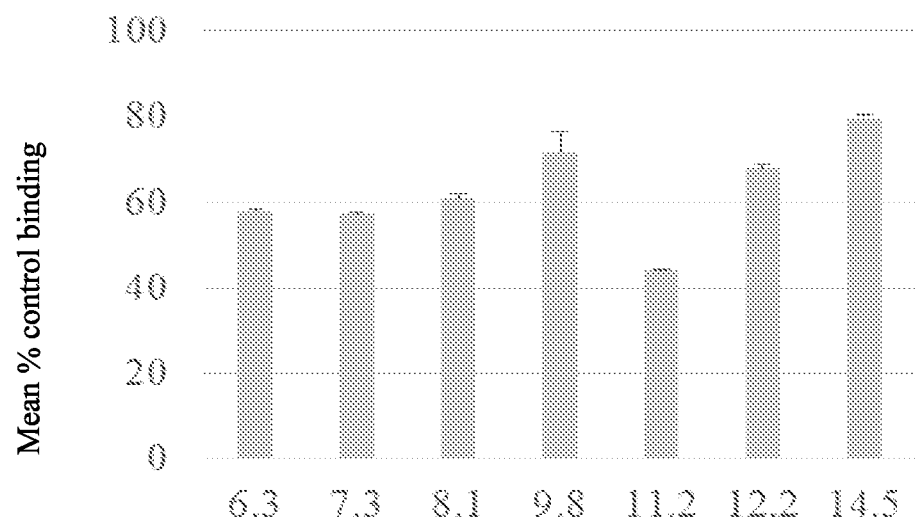
FIGS. 4A-4B. Hyperimmune llama serum blocking assay. The percentage of $V_HH$ binding to hyperimmune serum pretreated VLPs was calculated compared to the positive control of each $V_HH$ binding to the VLPs without pretreatment. Bars represent the average of two independent assays.
Figure 4B:
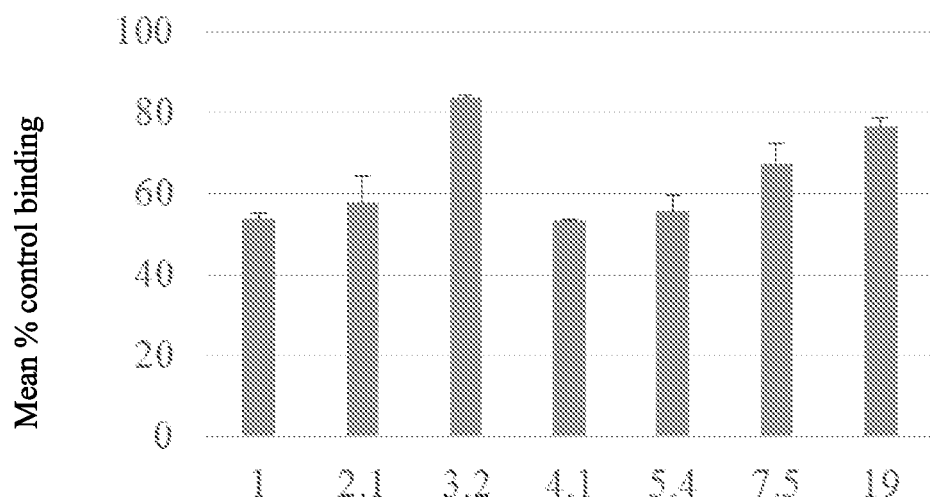

Surrogate Assays of Virus Neutralization: HBGA, Pig Gastrin Mucin, Saliva Blockade Assays and Hemagglutination Inhibition Test In order to study if the selected $V_HH$ possess the property to neutralize NoV infection, a panel of neutralizing surrogate assays were conducted and the summary of each $V_HH$ behavior is summarized in Table 4 and depicted in FIGS. 2 and 3.

TABLE 4

$V_HH$ behavior in surrogate neutralizing assays: summary results

| | EC50 (µg/ml) | | | HAI titer (µg/ml) | |
|---|---|---|---|---|---|
| | | PGM | Saliva | 0 Rh − RBC | |
| $V_HH$ GI.1 | HBGA H1 Norwalk VLP | type III Norwalk VLP | Ly+ Norwalk VLP | Norwalk VLP | Norovirus 2007 VLP |
| 6.3 | 1.006 | 0.661 | 2.035 | 0.19 | 0.05 |
| 7.3 | — | — | — | 0.39 | 0.05 |
| 8.1 | — | 4.139 | — | — | 0.78 |
| 9.8 | — | 1.144 | 1.718 | — | 3.12 |
| 10.4 | — | 0.667 | 1.136 | 0.1 | 0.05 |
| 11.2 | — | 6.856 | — | — | — |
| 12.2 | — | 2.594 | — | — | 0.8 |
| 13.1 | 2,032 | 1.289 | 2.267 | 0.19 | — |
| 14.5 | ND | 0.351 | 1.563 | 0.78 | 0.05 |
| H1 | ND | 0.275 | 2.637 | 0.19 | — |

| | EC50 (µg/ml) | | | HAI titer (µg/ml) B Rh + RBC | |
|---|---|---|---|---|---|
| | HBGA H3 | PGM type III | Saliva Ly+ | | |
| $V_HH$ GII.4 | MD145 VLP | MD2004 VLP | MD145 VLP | MD2004 VLP | MD145 VLP |
| 1 | 0.85 | 0.341 | 2.008 | — | — |
| 2.1 | — | — | — | — | — |
| 3.2 | 0.641 | 2.296 | 0.917 | 0.19 | 0.19 |
| 4.1 | 0.712 | 2.909 | 1.379 | 0.19 | 0.39 |
| 5.4 | 0.718 | 2.023 | 1.268 | 0.39 | 0.39 |
| 7.5 | — | — | — | — | 0.78 |
| 16 | — | 0.767 | — | — | — |
| 19 | — | 0.583 | 1.296 | 0.39 | 0.39 |

Positive values according to the established cut off are indicated in bold. For blockade assay cut off value is 2 µg/ml and for HAI assay the cut off value is 0.39 µg/ml.

Seven out of the 10 $V_HH$ specific to GI NoVs showed a blockade property by some of the surrogate neutralization assays. The best performances were observed with clone 6.3 that was able to interfere GI.1 VLPs attachment to the carbohydrates in all the blockade assays and also showed HAI properties. $V_HH$ 10.4 also represents a good option, since it was able to inhibit both Norwalk and P7-587 VLP binding to carbohydrates of the PGM, saliva and human RBC. Finally, clones 13.1 and H1 were effective but only specifically for Norwalk strain.

Regarding the $V_HH$ derived from the GII.4 MD2004 library, clones 3.2, 4.1 and 5.4 showed good EC50 values to inhibit VLP attachment to H3 carbohydrate, saliva and showed HAI, but higher amounts of $V_HH$s were needed to interfere the attachment of the VLPs to the PGM (2 µg/ml or higher).

Clone 1 was able to interfere with the VLP binding to synthetic carbohydrate H3, PGM and human saliva, but failed to induce HI. Clone 19, was able to inhibit VLP attachment to PGM, saliva and showed HAI properties. Clone 16, was able to inhibit VLP attachment to PGM with a good EC50, but failed to block carbohydrate binding and did not show HAI activity. Finally, $V_HH$ 2.1 and 7.5 did not show blocking activity.

The results of cross-reactivity obtained by ELISA, together with the results obtained in the neutralization surrogate assays utilizing different sources of carbohydrates (NoV VLP-HBGA, PGM and saliva blockade assays; and human RBC hemagglutination inhibition assays), all strongly suggest that some of the obtained $V_HH$ possess broadly potential viral neutralizing activity, and that the antibodies that can be utilized as a prophylactic or therapeutic intervention.

The clones directed toward GI.1 NoV did not display cross reactivity to the other GI genotypes tested with the exception of the $V_HH$ 7.3, which also recognized GI.3 Desert Shield strain by ELISA. Within the GI specific $V_HHs$, the clones 6.3, 10.4 and 14.5 all showed the best blockade performance within the different carbohydrate sources. The calculated EC50 values for these $V_HHs$ ranged between 0.275 and 2.0 µg/ml, all comparable to the EC50 values of the scFv derived from immunized chimpanzees (from 0.3 to 1.5 µg/ml) (Chen et al., J Virol 87(17): 9547-57, 2013). As therapy for the infection and diarrhea associated with GI.1 NoV, one strategy is a combination of the $V_HH$ antibodies 6.3 and 10.4, as they both illustrated the best overall blockade activity and they are directed toward different epitopes. Without being bound by theory, this is a characteristic that would diminish the probability of resistant mutant selection.

The GII.4 genotype is further classified into variants, when the difference in the amino acid sequence of VP1 is more than 5%; with this 5% of amino acid differences, a new variant is able to emerge into a new pandemy of NoV (Kroneman et al., Arch Virol 158(10): 2059-68, 2013). Several of the $V_HH$ antibodies specific for GII.4 NoV not only showed cross-reactivity among the different variants of GII.4 tested from 1977 to 2012, but also showed cross-reactivity among other genotypes within the GII genogroup thereby suggesting the future recognition of new variants within the GII.4 genotype that could potentially generate future pandemic outbreaks (Lindesmith et al., J Virol 85(1): 231-42, 2011; Lindesmith et al., PLoS Pathog 8(5): e1002705, 2012; Lindesmith et al., J Virol 86(2): 873-83, 2012; Lindesmith et al., J Virol 87(5): 2803-13, 2013). The GII.4 $V_HHs$ clones 3.2, 4.1 and 5.4 all showed similar CDR3 amino acid sequences. These data, together with the results from the competition assays, suggest these antibodies are directed toward the same epitope. Although they share the same CDR3, the $V_HH$ 3.2 displayed less cross reactivity with other GII genotypes different from GII.4 compared to $V_HH$ 5.4. This difference in specificity may ultimately be due to distinct amino acid changes in other regions of the sequences. The $V_HH$ 1, 4.1, and 5.4 all showed the overall best blockade profile, with the EC50 values ranging between 0.341 and 2.0 µg/ml.

Example 7

Competition Assays

To evaluate the ability of a polyclonal serum to impair the $V_HHs$ binding to NoV VLPs and vice versa, several competition assays were conducted. When llama NoV strain specific hyperimmune serum was used as blockade antibodies, the binding of the $V_HH$ 11.1 to the GI.1 Norwalk VLP was reduced 56%, while the binding of the other $V_HHs$ to the VLPs was reduced between 47% and 16% (FIG. 5). This result indicates that $V_HHs$ were able to bind to their corresponding epitope within the P domain of the VLP even in the presence of high concentration of conventional antibodies including those directed to the same epitopes.

The $V_HHs$ were able neither to block nor to compete with the binding of the anti-NoV hyperimmune sera from llama to the VLPs, even when a pool of all the $V_HHs$ was used, suggesting that they would not be directed to immunodominant epitopes.

Figure 6A:
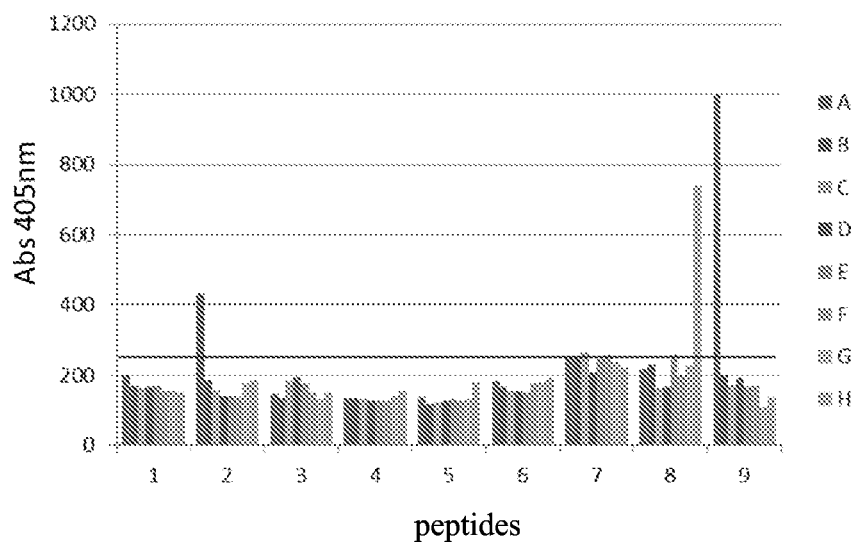
FIGS. 6A-6B. Epitope mapping of $V_HH$ 7.5 FIG. 6A. ELISA of overlapping peptides corresponding to the P domain of VP1.

Given the results obtained in the surrogate neutralization assays, two $V_HH$ specific for each NoV genogroup were selected and labeled with Alexa fluor in order to elucidate if these clones were directed to the same or a different epitope within theVP1 P domain. The competition assays between the different $V_HHs$ indicated that the clones 6.3 and 10.4 are directed to different epitopes and their binding sites are also different from the epitopes recognized by the other GI $V_HHs$. Regarding the GII specific $V_HHs$, clone 1 was directed to a distinct epitope to that recognized by $V_HH$ 5.4 and the ones recognized by the other GII specific $V_HHs$. The binding of labeled $V_HH$ 5.4, was impaired by the presence of $V_HH$ 3.2, $V_HH$ 4.1 and $V_HH$ 19 according to the immunofluorescence assay results, suggesting that all these clones are directed to the same epitope (FIG. 6). This observation is in agreement with the similarities detected in the CDR3 region of all the nanoantibodies (FIG. 8).

Additionally, $V_HHs$ 6.3 and 104 are directed to differential epitopes to those recognized by conventional Mabs 2, 4, 7, 40 and 47 specific for GI.1 NoVs and $V_HHs$ 1 and 4.1 are directed to different epitopes to those reacting with MAbs 3, 10 and 12, specific for GII.4 NoVs.

Example 8

Mapping of the Linear Epitope Recognized by $V_HH$ 7.5

The $V_HH$ 7.5 recognized all the GII strains tested by WB (FIG. 9) and ELISA (Table 3) indicating that it was directed to a linear epitope within the P domain of VP1 according to the chimeric VLP ELISA results (Table 2).

Figure 6B:
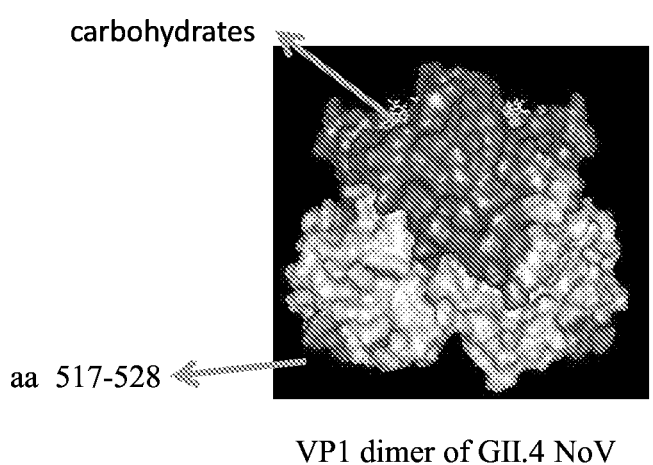

To conduct the epitope mapping of this $V_HH$, a peptidic library corresponding to the P domain of the VP1 amino acid sequence from NoV Toronto strain was synthesized. The library consisted of 67 peptides that were 17 amino acids long, with 5 amino acids overlapping with the previous and the next peptide of the sequence. The $V_HH$ 7.5 was tested against each of the peptides and a positive result was obtained for the overlapping peptides corresponding to amino acids 512-528 (GYFRFESWVNPFYTLAP, SEQ ID NO: 31) and 517-533 (ESWVNPFYTLAPMGTGN, SEQ ID NO: 32) while a negative result was obtained for the flanking overlapping peptides 507-523 (TVPPNGYFRFESWVNPF, SEQ ID NO: 33) and 522-538 (PFYTLAPMGTGNGRRRI, SEQ ID NO: 34) (FIG. 6). According to these results the sequences GYFRFESWVNPF (amino acids 1-12 of SEQ ID NO: 31) and PFYTLAPMGTGN (amino acids 6-17 of SEQ ID NO: 32) separately, were not enough to be recognized by $V_HH$ 7.5. Then, the putative epitope should be contained within the sequences of the two positive peptides, more specifically it should be comprised within the sequence from amino acids 517 to 528 (ESWVNPFYTLAP, amino acids 1-12 of SEQ ID NO: 32). This region of the P domain of VP1 protein is located close to the C-terminal end of the VP1 protein (FIG. 6b).

The linear epitope of $V_HH$ 7.5 was shown to be located at the C terminal of NoV VP1, within the P1 subdomain, in concordance with previous reports for cross reactive MAbs (Parker et al. J Virol 79(12): 7402-9, 2005; Shiota et al. J Virol 81(22): 12298-306, 2007). The epitope located within the protruding domain may be more accessible in the native virion than epitopes located in the S domain, the target of most of other cross reactive MAbs (Parra et al., PLoS One 8(6): e67592, 2013). Despite the lack of blockade activity of this $V_HH$, this $V_HH$ has the potential for inhibition of Norovirus infection and diarrhea through other mechanisms or to be useful in a diagnostic assay.

Example 9

Mapping of Conformational Putative Epitope of $V_HH$ 16 Binding

The $V_HH$ 16 was specific for VP1 of the MD2004 strain and was not able to recognize the other GII strains, including MD 145. For that reason specific mutants were designed targeting the differential amino acids between both strains.

The immunofluorescence assay showed that the $V_HH$ 16 failed to recognize a double mutant (G340A/E376Q) as well as a single mutant (G340A and E376Q) indicating that both amino acids 340 and 376 are critical for the binding of this $V_HH$ to VP1 and may be implicated in the epitope, while mutations in the amino acids 294, 368 and 389 did not impair $V_HH$ 16 binding (FIG. 7a). As a confirmation assay, VLPs representing the double escape mutant G340A/E 376Q were developed, expressed and purified. Of the anti-MD2004 $V_HH$ panel, only clone 16 failed to recognize this mutant by ELISA (FIG. 7b), in concordance with the immunofluorescence assay.

Noroviruses (NoV) are recognized as a leading cause of viral food borne human gastroenteritis worldwide, affecting humans of all ages. It is considered to be the second leading cause of childhood diarrhea after rotavirus. Additionally, NoV chronic infection represents a significant problem in immunocompromised patients. The infectious oral dose is estimated to be less than 20 viral particles, with immunocompetent patients usually suffering gastroenteritis followed by viral shedding for 20 to 40 days while immunocompromised patients usually become chronically infected with viral shedding lasting weeks to years (Bokand Green. N Engl J Med 367(22): 2126-32, 2012; Green, Caliciviridae: The Noroviruses. Fields Virology, 6th edition. H. P. Knipe D M, Griffin et al., Philadelphia: Lippincott Williams & Wilkins: 582-608, 2013).

Noroviruses present a broad genetic variability, with humans mainly infected with genogroups GI and GII. The latter is prevalent worldwide with more than 30 genotypes being reported within this genogroup (Debbink, Lindesmith, et al., J Virol., Mar. 19, 2014; Kroneman, Vega, et al., Arch Virol 158(10): 2059-68, 2013). However, to date an in vitro cell culture system has not been develop to isolate and propagate the virus, thus limiting antigenic studies. As such, the real antigenic diversity, critical for a rational vaccine design, is still largely unknown. Thus, vaccines or therapeutic interventions to prevent and treat NoV diarrhea are therefore not yet available. Regarding vaccine effective design, many questions remain, such as the identification of the proper antigens involved in virus neutralization and protection (Debbink et al., J Virol, Mar. 19, 2014; Debbink et al., J Virol, Apr. 16, 2014).

Detailed knowledge of norovirus VP1 structure can be informed by this type of analysis with nanobodies.

In view of the many possible embodiments to which the principles of our invention may be applied, it should be recognized that illustrated embodiments are only examples of the invention and should not be considered a limitation on the scope of the invention. Rather, the scope of the invention is defined by the following claims. We therefore claim as our invention all that comes within the scope and spirit of these claims.

---

We claim:

1. An isolated V$_H$H monoclonal antibody, or an antigen binding fragment thereof, comprising a heavy chain domain, wherein the heavy chain variable domain comprises a heavy chain complementarity determining region (HCDR)1, an HCDR2 and an HCDR3, and wherein the V$_H$H monoclonal antibody specifically binds a Norovirus (NoV) polypeptide, and wherein a) the CDR1 comprises amino acids 26-33 of SEQ ID NO: 3, the CDR2 comprises amino acids 51-57 of SEQ ID NO: 3, and the CDR3 comprises amino acids 96-109 of SEQ ID NO: 3;
b) the CDR1 comprises amino acids 26-33 of SEQ ID NO: 2, the CDR2 comprises amino acids 51-57 of SEQ ID NO: 2, and the CDR3 comprises amino acids 96-109 of SEQ ID NO: 2;
c) the CDR1 comprises amino acids 26-33 of SEQ ID NO: 1, the CDR2 comprises amino acids 51-57 of SEQ ID NO: 1, and the CDR3 comprises amino acids 96-109 of SEQ ID NO: 1;
d) the CDR1 comprises amino acids 26-33 of SEQ ID NO: 4, the CDR2 comprises amino acids 51-57 of SEQ ID NO: 4, and the a CDR3 comprises amino acids 96-109 of SEQ ID NO: 4;
e) the CDR1 comprising amino acids 26-33 of SEQ ID NO: 5, the CDR2 comprising amino acids 51-58 of SEQ ID NO: 5, and the CDR3 comprising amino acids 97-110 of SEQ ID NO: 5;
f) the CDR1 comprises amino acids 26-33 of SEQ ID NO: 6, the CDR2 comprises amino acids 51-58 of SEQ ID NO: 6, and the CDR5 comprises amino acids 97-111 of SEQ ID NO: 6;
g) the CDR1 comprises amino acids 26-33 of SEQ ID NO: 7, the CDR2 comprises amino acids 51-58 of SEQ ID NO: 7, and the CDR3 comprises amino acids 97-111 of SEQ ID NO: 7;
h) the CDR1 comprises amino acids 26-33 of SEQ ID NO: 8, the CDR2 comprises amino acids 51-58 of SEQ ID NO: 8, and the CDR3 comprises amino acids 97-111 of SEQ ID NO: 8;
i) the CDR1 comprises amino acids 26-33 of SEQ ID NO: 9, the CDR2 comprises amino acids 51-57 of SEQ ID NO: 9, and the CDR3 comprises amino acids 96-112 of SEQ ID NO: 9;
j) the CDR1 comprises amino acids 26-33 of SEQ ID NO: 10, the CDR2 comprises amino acids 51-57 of SEQ ID NO: 10, and the CDR3 comprises amino acids 96-112 of SEQ ID NO: 10;
k) the CDR1 comprises amino acids 26-33 of SEQ ID NO: 11, the CDR2 comprises amino acids 51-57, and the CDR3 comprises amino acids 96-114 of SEQ ID NO: 11;
l) the CDR1 comprises amino acids 26-33 of SEQ ID NO: 12, the CDR2 comprises amino acids 51-57 of SEQ ID NO: 12, and the CDR3 comprises amino acids 96-112 of SEQ ID NO: 12;
m) the CDR1 comprises amino acids 26-33 of SEQ ID NO: 13, the CDR2 comprises amino acids 51-58 of SEQ ID NO: 13, and the CDR3 comprises amino acids 97-113 of SEQ ID NO: 13;
n) the CDR1 comprises amino acids 26-33 of SEQ ID NO: 14, the CDR2 comprises amino acids 51-58 of SEQ ID NO: 14, and the CDR3 comprises amino acids 97-113 of SEQ ID NO: 14;
o) the CDR1 comprises amino acids 26-33 of SEQ ID NO: 15, the CDR2 comprises amino acids 51-58 of SEQ ID NO: 15, and the CDR3 comprises amino acids 97-114 of SEQ ID NO: 15;
p) the CDR1 comprises amino acids 26-33 of SEQ ID NO: 16, the CDR2 comprises amino acids 51-57 of SEQ ID NO: 16, and the CDR3 comprises amino acids 96-107 of SEQ ID NO: 16;

q) the CDR1 comprises amino acids 26-33 of SEQ ID NO: 17, the CDR2 comprises amino acids 51-58 of SEQ ID NO: 17, and the CDR3 comprises amino acids 97-113 of SEQ ID NO: 17;

r) the CDR1 comprising amino acids 26-33 of SEQ ID NO: 18, the CDR2 comprising amino acids 51-58 of SEQ ID NO: 18, and the CDR3 comprising amino acids 97-114 of SEQ ID NO: 18;

s) the CDR1 comprises amino acids 26-33 of SEQ ID NO: 19, the CDR2 comprises amino acids 51-58 of SEQ ID NO: 19, and the CDR3 comprises amino acids 97-113 of SEQ ID NO: 19;

t) the CDR1 comprising amino acids 26-33 of SEQ ID NO: 20, the CDR2 comprises amino acids 51-57 of SEQ ID NO:20, and the CDR3 comprises amino acids 96-111 of SEQ ID NO: 20; or u) the CDR1 comprises amino acids 26-33 of SEQ ID NO: 21, the CDR2 comprises amino acids 51-57 of SEQ ID NO:21, and the CDR3 comprises amino acids 96-102 of SEQ ID NO: 21.

2. The isolated $V_HH$ monoclonal antibody of claim 1, wherein the heavy chain variable domain comprises the amino acid sequence set for the as one of SEQ ID NOs: 1-21.

3. The isolated monoclonal antibody of claim 1, wherein the antibody is an IgG.

4. The isolated monoclonal antibody of claim 1, wherein the antibody is humanized or chimeric.

5. The isolated antigen binding fragment of the isolated monoclonal antibody of claim 1.

6. The isolated monoclonal antibody or the antigen binding fragment of claim 1, wherein the antibody or antigen binding fragment is labeled.

7. The isolated monoclonal antibody or antigen binding fragment of claim 6, wherein the label is a fluorescent, an enzymatic, or a radioactive label.

8. A composition comprising an effective amount of the antibody of claim 1, or the antigen binding fragment of the antibody, and a pharmaceutically acceptable carrier.

9. An isolated nucleic acid molecule encoding the monoclonal antibody or antigen binding fragment of claim 1.

10. A method of detecting a Norovirus infection in a subject comprising:
contacting a biological sample from the subject with at least one isolated monoclonal antibody of claim 1 or the antigen binding fragment thereof; and
detecting antibody bound to the sample,
wherein the presence of antibody bound to the sample indicates that the subject has an Norovirus infection.

11. The method of claim 10, wherein the isolated monoclonal antibody or the antigen binding fragment is directly labeled.

12. The method of claim 10, further comprising:
contacting the sample with a second antibody that specifically binds the isolated human monoclonal antibody; and
detecting the binding of the second antibody,
wherein an increase in binding of the second antibody to the sample as compared to binding of the second antibody to a control sample detects the presence of an Norovirus infection the subject.

13. A method for inhibiting a Norovirus infection in a subject, comprising:
administering to the subject a therapeutically effective amount of an antibody of claim 1, an antigen binding fragment thereof, or a nucleic acid encoding the antibody or antigen binding fragment,
thereby inhibiting the Norovirus infection.

14. The method of claim 13, further comprising administering to the subject an anti-viral agent.

15. The method of claim 13, further comprising measuring viral titer in a biological sample from the subject.

16. A composition comprising an effective amount of the nucleic acid molecule of claim 9; or a vector comprising the nucleic acid molecule; and a pharmaceutically acceptable carrier.

17. A method for inhibiting a Norovirus infection in a subject, comprising:
administering to the subject a therapeutically effective amount of an antibody of claim 1, an antigen binding fragment thereof, or a nucleic acid encoding the antibody or antigen binding fragment,
thereby inhibiting the Norovirus infection.

18. The method of claim 17, further comprising administering to the subject an anti-viral agent.

19. An isolated $V_HH$ monoclonal antibody, or an antigen binding fragment thereof, comprising a heavy chain domain, wherein the heavy chain variable domain comprises a heavy chain complementarity determining region (HCDR)1, an HCDR2 and an HCDR3, and wherein the $V_HH$ monoclonal antibody specifically binds a Norovirus polypeptide, and wherein:

a) the CDR1 comprises amino acids 26-33 of SEQ ID NO: 22, the CDR2 comprises amino acids 51-57 of SEQ ID NO:22, and the CDR3 comprises amino acids 96-110 of SEQ ID NO: 22;

b) the CDR1 comprises amino acids 26-33 of SEQ ID NO: 23, the CDR2 comprises amino acids 50-56 of SEQ ID NO:23, and the CDR3 comprises amino acids 95-104 of SEQ ID NO: 23;

c) the CDR1 comprises amino acids 26-33 of SEQ ID NO: 24, the CDR2 comprises amino acids 51-57 of SEQ ID NO:24, and the CDR3 comprises amino acids 96-107 of SEQ ID NO: 24;

d) the CDR1 comprises amino acids 26-33 of SEQ ID NO: 25, the CDR2 comprises amino acids 51-57 of SEQ ID NO: 25, and the CDR3 comprises amino acids 100-110 of SEQ ID NO: 25;

e) the CDR1 comprises amino acids 26-33 of SEQ ID NO: 26, the CDR2 comprises amino acids 50-57 of SEQ ID NO:26, and the CDR3 comprises amino acids 96-117 of SEQ ID NO: 26;

f) the CDR1 comprises amino acids 26-33 of SEQ ID NO: 27, the CDR2 comprises amino acids 51-58 of SEQ ID NO:27, and the CDR3 comprises amino acids 97-108 of SEQ ID NO: 27;

g) the CDR1 comprises amino acids 26-33 of SEQ ID NO: 28, the CDR2 comprises amino acids 51-57 of SEQ ID NO:28, and the CDR3 comprises amino acids 96-112 of SEQ ID NO: 28;

h) the CDR1 comprises amino acids 26-33 of SEQ ID NO: 29, the CDR2 comprises amino acids 51-58 of SEQ ID NO:29, and the CDR3 comprises amino acids 97-115 of SEQ ID NO: 29; or i) the CDR1 comprises amino acids 26-33 of SEQ ID NO: 30, the CDR2 comprises amino acids 51-58 of SEQ ID NO:30, and the CDR3 comprises amino acids 97-121 of SEQ ID NO: 30.

20. The isolated $V_HH$ monoclonal antibody of claim 19, wherein the heavy chain variable domain comprises the amino acid sequence set forth as one of SEQ ID NOs: 22-30.

21. The isolated $V_HH$ monoclonal antibody of claim 20, wherein the monoclonal antibody specifically binds viral protein (VP)1.

22. The isolated nucleic acid molecule of claim 9, operably linked to a promoter.

23. An expression vector comprising the isolated nucleic acid molecule of claim 22.

24. The expression vector of claim 23, wherein the vector is a viral vector.

25. An isolated host cell transformed with the nucleic acid molecule of claim 22, or an expression vector comprising the nucleic acid molecule.

26. An isolated nucleic acid molecule encoding the monoclonal antibody or antigen binding fragment of claim 19.

27. The isolated nucleic acid molecule of claim 26, operably linked to a promoter.

28. An expression vector comprising the isolated nucleic acid molecule of claim 27.

29. An isolated host cell transformed with the nucleic acid molecule of claim 27, or an expression vector comprising the nucleic acid molecule.

30. A composition comprising an effective amount of the antibody of claim 19, or the antigen binding fragment of the antibody, or an isolated nucleic acid molecule encoding the antibody or the antigen binding fragment, and a pharmaceutically acceptable carrier.

31. A method of detecting a Norovirus infection in a subject comprising:
   contacting a biological sample from the subject with at least one isolated monoclonal antibody of claim 19 or the antigen binding fragment thereof; and
   detecting antibody bound to the sample,
   wherein the presence of antibody bound to the sample indicates that the subject has an Norovirus infection.

32. The method of claim 31, wherein the isolated monoclonal antibody or the antigen binding fragment is directly labeled.

* * * * *

UNITED STATES PATENT AND TRADEMARK OFFICE
CERTIFICATE OF CORRECTION

PATENT NO. : 10,000,556 B2
APPLICATION NO. : 14/889774
DATED : June 19, 2018
INVENTOR(S) : Bok et al.

Page 1 of 1

It is certified that error appears in the above-identified patent and that said Letters Patent is hereby corrected as shown below:

In the Claims

Claim 2, Column 115, Line 26, "set for the as one of" should read --set forth as one of--.

Claim 12, Column 115, Line 63, "Norovirus infection the subject" should read --Norovirus infection in the subject--.

Signed and Sealed this
Thirteenth Day of April, 2021

Drew Hirshfeld
*Performing the Functions and Duties of the
Under Secretary of Commerce for Intellectual Property and
Director of the United States Patent and Trademark Office*

SEQUENCE LISTING

<160> NUMBER OF SEQ ID NOS: 68

<210> SEQ ID NO 1
<211> LENGTH: 131
<212> TYPE: PRT
<213> ORGANISM: Lama glama

<400> SEQUENCE: 1

```
Gln Val Gln Leu Gln Glu Ser Gly Gly Gly Leu Val Gln Pro Gly Gly
1               5                   10                  15

Ser Leu Arg Leu Ser Cys Ala Ala Ser Glu Ser Thr Pro Ser Ile Asn
            20                  25                  30

Thr Met Gly Trp Tyr Arg Gln Ala Pro Gly Lys Glu Arg Glu Leu Val
        35                  40                  45

Ala Thr Ile Thr Ser Gly Gly Met Thr Asn Tyr Ala Asp Ser Val Lys
    50                  55                  60

Gly Arg Phe Thr Ile Ser Arg Asp Asn Gly Lys Asn Thr Val Tyr Leu
65                  70                  75                  80

Gln Met Asn Ser Leu Glu Pro Gly Asp Thr Ala Val Tyr Tyr Cys Asn
                85                  90                  95

Leu Lys Arg Arg Asp Leu Gln Ala Arg Phe Gly Gly Tyr Trp Gly Gln
            100                 105                 110

Gly Thr Gln Val Thr Val Ser Ser Glu Pro Lys Thr Gln Thr Thr Thr
        115                 120                 125
```

Ser Gly Arg
    130

<210> SEQ ID NO 2
<211> LENGTH: 132
<212> TYPE: PRT
<213> ORGANISM: Lama glama

<400> SEQUENCE: 2

Gln Val Lys Leu Gln Gln Ser Gly Gly Gly Leu Val Gln Pro Gly Gly
1               5                   10                  15

Ser Leu Arg Leu Ser Cys Ala Ala Ser Glu Ser Thr Ile Ser Ile Asn
            20                  25                  30

Thr Leu Gly Trp Tyr Arg Gln Ala Pro Gly Asn Gln Arg Glu Leu Val
        35                  40                  45

Ala Thr Ile Thr Thr Gly Gly Thr Thr Asn Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Asn Leu Glu Pro Gly Asp Thr Ala Val Tyr Tyr Cys Asn
                85                  90                  95

Leu Lys Arg Arg Asp Leu Gln Ser Arg Phe Gly Gly Tyr Trp Gly Gln
            100                 105                 110

Gly Thr Gln Val Thr Val Ser Ser Glu Pro Gln Asp Thr Lys Thr Thr
        115                 120                 125

Thr Ser Gly Arg
    130

<210> SEQ ID NO 3
<211> LENGTH: 131
<212> TYPE: PRT
<213> ORGANISM: Lama glama

<400> SEQUENCE: 3

Gln Val Gln Leu Gln Gln Ser Gly Gly Gly Leu Val Gln Pro Gly Gly
1               5                   10                  15

Ser Leu Arg Leu Ser Cys Val Ala Ser Glu Ser Thr Val Ser Ile Asn
            20                  25                  30

Ile Met Gly Trp Tyr Arg Gln Ala Pro Gly Lys Gln Arg Glu Leu Val
        35                  40                  45

Ala Thr Ile Thr Thr Gly Gly Thr Thr Asn Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Glu Pro Glu Asp Thr Ala Val Tyr Tyr Cys Asn
                85                  90                  95

Leu Lys Arg Arg Asp Leu Gln Ala Arg Phe Gly Gly Tyr Trp Gly Gln
            100                 105                 110

Gly Thr Gln Val Thr Val Ser Ser Glu Pro Lys Thr Pro Lys Pro Thr
        115                 120                 125

Ser Gly Arg
    130

<210> SEQ ID NO 4
<211> LENGTH: 131
<212> TYPE: PRT
<213> ORGANISM: Lama glama

-continued

<400> SEQUENCE: 4

Gln Val Lys Leu Gln Gln Ser Gly Gly Gly Leu Val Gln Pro Gly Gly
1               5                   10                  15

Ser Leu Arg Leu Ser Cys Ala Ala Ser Glu Ser Thr Pro Ser Ile Asn
            20                  25                  30

Thr Met Gly Trp Tyr Arg Gln Ala Pro Gly Lys Glu Arg Glu Leu Val
        35                  40                  45

Ala Thr Ile Thr Ser Gly Gly Met Thr Asn Tyr Ala Asp Ser Val Lys
    50                  55                  60

Gly Arg Phe Thr Ile Ser Arg Asp Asn Gly Lys Asn Thr Val Tyr Leu
65                  70                  75                  80

Gln Met Asn Ser Leu Glu Pro Gly Asp Thr Ala Val Tyr Tyr Cys Asn
                85                  90                  95

Leu Lys Arg Arg Asp Leu Gln Ala Arg Phe Gly Gly Tyr Trp Gly Gln
            100                 105                 110

Gly Thr Gln Val Thr Val Ser Glu Pro Lys Thr Pro Lys Pro Gln
        115                 120                 125

Ser Gly Arg
    130

<210> SEQ ID NO 5
<211> LENGTH: 132
<212> TYPE: PRT
<213> ORGANISM: Lama glama

<400> SEQUENCE: 5

Gln Val Lys Leu Gln Gln Ser Gly Gly Gly Leu Val Gln Pro Gly Gly
1               5                   10                  15

Ser Leu Arg Leu Ser Cys Ala Ala Ser Gly Phe Thr Phe Arg Asn Tyr
            20                  25                  30

Ala Met Ser Trp Val Arg Gln Ala Pro Gly Lys Gly Leu Glu Trp Val
        35                  40                  45

Ser Ala Ile Ala Ala Gly Gly Ala Val Thr Lys Tyr Ala Asp Ser Val
    50                  55                  60

Lys Gly Arg Phe Thr Ile Ser Arg Asp Asn Ala Arg Asp Thr Leu Tyr
65                  70                  75                  80

Leu Gln Met Asn Ser Leu Lys Pro Glu Asp Thr Ala Val Tyr Tyr Cys
                85                  90                  95

Ala Lys Pro Arg Asp Phe Trp Tyr Ser Pro Glu Phe Asp Phe Arg Gly
            100                 105                 110

Gln Gly Thr Gln Val Thr Val Ser Ser Glu Pro Lys Asn Gln Asn Gln
        115                 120                 125

Thr Ser Gly Arg
    130

<210> SEQ ID NO 6
<211> LENGTH: 133
<212> TYPE: PRT
<213> ORGANISM: Lama glama

<400> SEQUENCE: 6

Gln Val Gln Leu Gln Gln Ser Gly Gly Gly Leu Val Gln Ala Gly Asp
1               5                   10                  15

Ser Leu Thr Ile Ser Cys Ala Ser Leu Phe Thr Phe Ser Thr Ser
            20                  25                  30

Thr Met Gly Trp Phe Arg Gln Ala Pro Gly Lys Glu Arg Glu Phe Val
            35                  40                  45

Ala Ala Ile Lys Ser Ser Gly Ser Ser Met Tyr Tyr Ala Asp Ser Val
 50                  55                  60

Gln Gly Arg Phe Thr Ile Ser Arg Asp Asn Ala Lys Lys Thr Val Thr
 65                  70                  75                  80

Leu Gln Met Asn Ser Leu Lys Pro Glu Asp Thr Ala Val Tyr Tyr Cys
                 85                  90                  95

Ala Lys Gly Val Tyr Gly Ser Arg Arg Ser Ala Asp Phe Gly Ser Trp
                100                 105                 110

Gly Gln Gly Thr Gln Val Thr Val Ser Ser Glu Pro Lys Thr Pro Lys
                115                 120                 125

Pro Gln Ser Gly Arg
            130

<210> SEQ ID NO 7
<211> LENGTH: 133
<212> TYPE: PRT
<213> ORGANISM: Lama glama

<400> SEQUENCE: 7

Gln Val Gln Leu Gln Gln Ser Gly Gly Gly Leu Val Gln Ala Gly Asp
 1               5                  10                  15

Ser Leu Arg Ile Ser Cys Ala Ala Ser Leu Phe Thr Phe Ser Thr Ser
                 20                  25                  30

Thr Met Gly Trp Phe Arg Gln Ala Pro Gly Lys Glu Arg Glu Phe Val
            35                  40                  45

Ala Ala Ile Arg Ser Thr Gly Asp Ser Met Tyr Tyr Ala Asp Ser Val
 50                  55                  60

Gln Gly Arg Phe Thr Ile Ser Arg Asp Asn Ala Lys Lys Met Val Tyr
 65                  70                  75                  80

Leu Gln Met Asn Asn Leu Lys Pro Glu Asp Thr Ala Val Tyr Tyr Cys
                 85                  90                  95

Ala Lys Gly Val Tyr Gly Ser Arg Arg Ser Ala Asp Phe Gly Ser Trp
                100                 105                 110

Gly Gln Gly Thr Gln Val Thr Val Ser Ser Glu Pro Lys Thr Pro Lys
                115                 120                 125

Pro Gln Ser Gly Arg
            130

<210> SEQ ID NO 8
<211> LENGTH: 133
<212> TYPE: PRT
<213> ORGANISM: Lama glama

<400> SEQUENCE: 8

Asp Val Gln Leu Gln Ala Ser Gly Gly Gly Leu Val Gln Ala Gly Gly
 1               5                  10                  15

Ser Leu Arg Ile Ser Cys Thr Ala Asp Gly Tyr Thr Phe Ser Thr Ser
                 20                  25                  30

Thr Met Gly Trp Phe Arg Gln Ala Pro Gly Lys Glu Arg Glu Phe Val
            35                  40                  45

Ala Ala Ile Lys Ser Asp Gly Ser Ile Met Tyr Tyr Ala Asp Ser Val
 50                  55                  60

Ala Gly Arg Phe Ile Ile Ser Arg Asp Asn Ala Lys Lys Met Val Phe
 65                  70                  75                  80

Leu Gln Met Asp Arg Leu Lys Pro Glu Asp Thr Ala Val Tyr Tyr Cys
                85                  90                  95

Ala Lys Gly Val Tyr Gly Ser Arg Ser Ala Asp Phe Gly Trp Trp
            100                 105                 110

Gly Gln Gly Thr Gln Val Thr Val Ser Ser Glu Pro Lys Thr Pro Lys
        115                 120                 125

Pro Gln Ser Gly Arg
    130

<210> SEQ ID NO 9
<211> LENGTH: 134
<212> TYPE: PRT
<213> ORGANISM: Lama glama

<400> SEQUENCE: 9

Gln Val Lys Leu Gln Glu Ser Gly Gly Gly Leu Val Gln Ala Gly Glu
1               5                   10                  15

Ser Leu Arg Leu Ser Cys Ala Ala Ser Gly Ser Asn Phe Ser Ile Asn
            20                  25                  30

Gly Val Gly Trp Tyr Arg Gln Ala Pro Gly Lys Gln Arg Glu Leu Val
        35                  40                  45

Ala Gly Ile Thr Asn Gly Gly Tyr Thr Ser Tyr Ala Asp Ser Val Lys
    50                  55                  60

Gly Arg Phe Thr Ile Ser Thr Asp Asn Ala Lys Asn Thr Val Tyr Leu
65                  70                  75                  80

Gln Met Asn Ser Leu Arg Pro Glu Asp Thr Ala Val Tyr Tyr Cys Asn
                85                  90                  95

Ala Asn Phe Gln Ile His Arg Ser Gly Ala Asp Tyr Val Arg Asn Tyr
            100                 105                 110

Trp Gly Gln Gly Thr Gln Val Thr Val Ser Ala Glu Pro Arg Thr Lys
        115                 120                 125

Thr Thr Thr Ser Gly Arg
    130

<210> SEQ ID NO 10
<211> LENGTH: 134
<212> TYPE: PRT
<213> ORGANISM: Lama glama

<400> SEQUENCE: 10

Gln Val Lys Leu Gln Gln Ser Gly Gly Gly Leu Val Gln Ala Gly Gly
1               5                   10                  15

Ser Leu Arg Leu Ser Cys Ala Ala Ser Gly Asn Phe Phe Thr Leu Asn
            20                  25                  30

Gly Val Ala Trp Tyr Arg Gln Ala Pro Gly Lys Gln Arg Glu Leu Val
        35                  40                  45

Ala Gly Ile Thr Ser Gly Gly Trp Thr Asn Tyr Ala Asp Ser Val Lys
    50                  55                  60

Gly Arg Phe Thr Ile Ser Ala Asp Asn Ala Lys Asn Thr Val Tyr Leu
65                  70                  75                  80

Gln Met Asn Ser Leu Arg Pro Glu Asp Thr Ala Val Tyr Tyr Cys Asn
                85                  90                  95

Ala Asn Leu Gln Ile His Arg Asp Ser Ser Gly Asp Val Arg Asn Val
            100                 105                 110

Trp Gly Gln Gly Thr Gln Val Thr Val Ser Ser Glu Pro Lys Thr Pro
        115                 120                 125

Lys Pro Gln Ser Gly Arg
    130

<210> SEQ ID NO 11
<211> LENGTH: 136
<212> TYPE: PRT
<213> ORGANISM: Lama glama

<400> SEQUENCE: 11

Asp Val Gln Leu Gln Ala Ser Gly Gly Gly Leu Val Gln Ala Gly Gly
1               5                   10                  15

Ser Leu Arg Leu Ser Cys Ala Ala Ser Gly Ser Phe Phe Ser Ile Asn
            20                  25                  30

Gly Val Gly Trp Tyr Arg Gln Ala Pro Gly Lys Gln Arg Glu Leu Val
        35                  40                  45

Ala Gly Ile Thr Asn Gly Gly Phe Thr Asn Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Asn
                85                  90                  95

Ala Asn Leu Gln Ile Ser Arg Ser Glu Asp Gly Ala Tyr Val Val Arg
            100                 105                 110

Asn Tyr Trp Gly Gln Gly Thr Gln Ile Thr Val Ser Ser Glu Pro Lys
        115                 120                 125

Thr Pro Lys Pro Gln Ser Gly Arg
    130                 135

<210> SEQ ID NO 12
<211> LENGTH: 134
<212> TYPE: PRT
<213> ORGANISM: Lama glama

<400> SEQUENCE: 12

Asp Val Gln Leu Gln Ala Ser Gly Gly Gly Leu Val Gln Ala Gly Gly
1               5                   10                  15

Ser Leu Arg Leu Ser Cys Ala Ala Ser Gly Ser Gly Phe Ser Ile Asn
            20                  25                  30

Gly Val Gly Trp Tyr Arg Gln Thr Pro Gly Arg Gln Arg Glu Leu Val
        35                  40                  45

Ala Gly Ile Thr Ile Gly Gly Tyr Thr Asn Tyr Ala Asp Ser Val Lys
    50                  55                  60

Gly Arg Phe Thr Ile Ser Ser Asp Asn Ala Lys Asn Thr Val Tyr Leu
65                  70                  75                  80

Gln Met Asn Ser Leu Lys Pro Glu Asp Thr Ala Val Tyr Tyr Cys Asn
                85                  90                  95

Ala Asn Leu Gln Phe Tyr Arg Gly Gly Gly Ser Asp Val Lys Asn Tyr
            100                 105                 110

Trp Gly Gln Gly Thr Gln Val Thr Val Ser Ser Glu Pro Lys Thr Pro
        115                 120                 125

Lys Pro Gln Ser Gly Arg
    130

<210> SEQ ID NO 13
<211> LENGTH: 135
<212> TYPE: PRT
<213> ORGANISM: Lama glama

-continued

<400> SEQUENCE: 13

Gln Val Gln Leu Gln Glu Ser Gly Gly Gly Leu Val Gln Ala Gly Gly
1               5                   10                  15

Ser Leu Arg Leu Ser Cys Ala Ala Ser Gly Leu Thr Phe Ser Ser Tyr
            20                  25                  30

Ala Met Gly Trp Phe His Gln Ala Pro Gly Lys Glu Arg Glu Phe Val
        35                  40                  45

Ala Ala Ile Asn Trp Ser Gly Arg Asp Thr Tyr Tyr Ala Asp Ser Val
    50                  55                  60

Lys Gly Arg Phe Thr Ile Ser Arg Asp Asn Arg Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Ala Glu Phe Phe Ser Ser Gly Asp Pro Leu Pro Gly Met Asp
            100                 105                 110

Tyr Trp Gly Lys Gly Thr Leu Val Thr Val Ser Ser Glu Pro Lys Thr
        115                 120                 125

Gln Asn His Asn Ser Gly Arg
    130                 135

<210> SEQ ID NO 14
<211> LENGTH: 135
<212> TYPE: PRT
<213> ORGANISM: Lama glama

<400> SEQUENCE: 14

Gln Val Lys Leu Gln Gln Ser Gly Gly Gly Leu Val Gln Ala Gly Gly
1               5                   10                  15

Ser Leu Arg Leu Ser Cys Ala Ala Ser Gly Leu Thr Phe Ser Ser Tyr
            20                  25                  30

Ala Met Gly Trp Phe Arg Gln Ala Pro Gly Lys Glu Arg Glu Phe Val
        35                  40                  45

Ala Ala Ile Asn Trp Ser Gly Arg Asp Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Thr Asn Ser Leu Lys Pro Glu Asp Thr Ala Val Tyr Tyr Cys
                85                  90                  95

Ala Ala Ala Glu Phe Leu Pro Thr Gln Arg Ser Pro Arg Glu Tyr Asp
            100                 105                 110

Tyr Trp Gly Leu Gly Thr Gln Val Thr Val Ser Ser Glu Pro Lys Thr
        115                 120                 125

Pro Lys Pro Gln Ser Gly Arg
    130                 135

<210> SEQ ID NO 15
<211> LENGTH: 136
<212> TYPE: PRT
<213> ORGANISM: Lama glama

<400> SEQUENCE: 15

Gln Val Lys Leu Gln Gln Ser Gly Gly Gly Leu Val Gln Ala Gly Gly
1               5                   10                  15

Ser Leu Arg Leu Ser Cys Ala Ala Ser Gly Tyr Ala Phe Asn Thr Tyr
            20                  25                  30

Thr Met Ala Trp Phe Arg Gln Ala Pro Gly Lys Glu Arg Glu Phe Val

```
                35                  40                  45
Ala Leu Val Gly Met Lys Val Asp Gly Lys Ile Tyr Ala Asp Ser Val
 50                  55                  60
Lys Gly Arg Phe Thr Ile Ser Arg Asp Asn Glu Gln Lys Thr Val Leu
 65                  70                  75                  80
Leu Glu Met Asn His Leu Glu Pro Glu Asp Thr Ala Ile Tyr Tyr Cys
                 85                  90                  95
Ala Ala Ser Arg Arg Phe Trp Thr Ala Ala Leu Asn Gly Ala Asp Tyr
                100                 105                 110
Pro Tyr Trp Gly Gln Gly Thr Gln Val Thr Val Ser Ser Glu Pro Lys
                115                 120                 125
Thr Pro Lys Pro Gln Ser Gly Arg
                130                 135

<210> SEQ ID NO 16
<211> LENGTH: 129
<212> TYPE: PRT
<213> ORGANISM: Lama glama

<400> SEQUENCE: 16

Gln Val Lys Leu Gln Gln Ser Gly Gly Gly Leu Val Gln Ala Gly Gly
 1                   5                  10                  15
Ser Leu Arg Leu Ser Cys Ala Ala Ser Gly Ile Val Phe Ser Phe Asn
                 20                  25                  30
Ala Met Gly Trp Tyr Arg Val Pro Gly Lys Gln Arg Glu Leu Val
                 35                  40                  45
Ala Asp Ile Leu Lys Ser Gly Gly Thr Asn Val Val Asp Ser Val Lys
 50                  55                  60
Gly Arg Phe Ala Ile Ser Arg Asp Ser Ala Gln Asn Thr Leu Tyr Leu
 65                  70                  75                  80
Gln Met Asn Arg Leu Lys Pro Glu Asp Thr Ala Val Tyr Tyr Cys Asn
                 85                  90                  95
Ala Arg Asp Trp Ser Asp Gly Phe Asp Glu Tyr Trp Gly Gln Gly Thr
                100                 105                 110
Gln Val Thr Val Ser Ser Glu Pro Lys Thr Pro Lys Pro Gln Ser Gly
                115                 120                 125
Arg

<210> SEQ ID NO 17
<211> LENGTH: 135
<212> TYPE: PRT
<213> ORGANISM: Lama glama

<400> SEQUENCE: 17

Gln Val Gln Leu Gln Gln Ser Gly Gly Gly Leu Val Gln Ala Gly Gly
 1                   5                  10                  15
Ser Leu Arg Leu Ser Cys Ser Ala Ser Gly Arg Thr Phe Ser Asn Tyr
                 20                  25                  30
Val Met Gly Trp Phe Arg Gln Ala Pro Gly Lys Glu Arg Glu Phe Val
                 35                  40                  45
Ala Thr Ile Ser Ala Ser Gly Ser Thr Tyr Cys Ala Asp Ser Val
 50                  55                  60
Glu Gly Arg Phe Thr Ile Ser Arg Asp Asn Ala Lys Asn Thr Ala Tyr
 65                  70                  75                  80
Leu Gln Met Asn Asn Leu Glu Pro Glu Asp Thr Ala Val Tyr Tyr Cys
                 85                  90                  95
```

```
Ala Ser Gly Pro Arg Ala Asn Ala Ser Ile Arg Arg Ser Gly Tyr Asn
                100                 105                 110

Tyr Trp Gly Gln Gly Thr Gln Val Thr Val Ser Ser Glu Pro Lys Thr
            115                 120                 125

Pro Lys Pro Gln Ser Gly Arg
        130                 135

<210> SEQ ID NO 18
<211> LENGTH: 136
<212> TYPE: PRT
<213> ORGANISM: Lama glama

<400> SEQUENCE: 18

Gln Val Gln Leu Gln Gln Ser Gly Gly Gly Leu Val Gln Ala Gly Gly
1               5                   10                  15

Ser Leu Arg Leu Ser Cys Ala Ala Ser Gly Leu Ala Phe Ser Ser Tyr
            20                  25                  30

Ala Ile Thr Trp Leu Arg Gln Ala Pro Gly Thr Glu Arg Glu Phe Val
        35                  40                  45

Ala Leu Ile Ser Gly Ser Gly Ser Ser Thr Tyr Tyr Ala Asp Ser Val
    50                  55                  60

Lys Gly Arg Phe Thr Ile Ser Arg Asn Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Thr Ala Ser Glu Phe Leu Leu His Pro Pro Pro Asn Gln Lys Tyr
            100                 105                 110

Asp Tyr Trp Gly Gln Gly Thr Gln Val Thr Val Ser Ser Glu Pro Lys
            115                 120                 125

Thr Pro Lys His Thr Ser Gly Arg
        130                 135

<210> SEQ ID NO 19
<211> LENGTH: 135
<212> TYPE: PRT
<213> ORGANISM: Lama glama

<400> SEQUENCE: 19

Gln Val Gln Leu Gln Gln Ser Gly Gly Gly Leu Val Arg Ala Gly Gly
1               5                   10                  15

Ser Leu Arg Leu Ser Cys Ser Ala Ser Gly Arg Thr Phe Gly Asn Glu
            20                  25                  30

Val Met Gly Trp Phe Arg Gln Ala Pro Gly Lys Glu Arg Glu Phe Val
        35                  40                  45

Ala Ala Ile Asn Trp Ser Ser Gly Asn Thr Tyr Tyr Arg Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Glu Pro Glu Asp Thr Ala Val Tyr Tyr Cys
                85                  90                  95

Ala Ala Arg Ser Arg Pro Ala Ile Ser Thr Arg Arg Pro Asp Tyr Phe
            100                 105                 110

Ala Trp Gly Gln Gly Thr Gln Val Thr Val Ser Ser Glu Pro Lys Thr
        115                 120                 125

Pro Lys Pro Gln Ser Gly Arg
        130                 135
```

<210> SEQ ID NO 20
<211> LENGTH: 133
<212> TYPE: PRT
<213> ORGANISM: Lama glama

<400> SEQUENCE: 20

Gln Val Gln Leu Gln Gln Ser Gly Gly Gly Leu Val Gln Ala Gly Gly
1               5                   10                  15

Ser Leu Arg Leu Ser Cys Thr Ala Ser Gly Arg Ile Asp Arg Thr Tyr
            20                  25                  30

Thr Val Ser Trp Phe Arg Gln Gly Pro Gly Lys Glu Arg Glu Phe Val
        35                  40                  45

Ala Thr Ile Ser Trp Asp Gly Ser Ile Tyr Tyr Asp Asn Ala Val Glu
    50                  55                  60

Gly Arg Phe Ser Ile Ser Gly Asp Asn Ala Lys Thr Thr Val Ala Leu
65                  70                  75                  80

Gln Met Asn Ser Leu Lys Pro Glu Asp Thr Ala Val Tyr Tyr Cys Ala
                85                  90                  95

Ala Arg Arg Arg Val Phe Ser Arg Ala Ala Ala Tyr Asn Tyr Trp
            100                 105                 110

Gly Gln Gly Thr Gln Val Thr Val Ser Ser Glu Pro Lys Thr Pro Lys
        115                 120                 125

Pro Gln Ser Gly Arg
        130

<210> SEQ ID NO 21
<211> LENGTH: 124
<212> TYPE: PRT
<213> ORGANISM: Lama glama

<400> SEQUENCE: 21

Gln Val Lys Leu Gln Gln Ser Gly Gly Gly Leu Val Gln Pro Gly Gly
1               5                   10                  15

Ser Leu Arg Leu Thr Cys Ala Ala Ser Gly Phe Pro Phe Ser Thr Tyr
            20                  25                  30

Ala Ile Arg Trp Val Arg Arg Pro Gly Lys Gly Leu Glu Trp Val
        35                  40                  45

Ser Thr Ile His Pro Asp Phe Thr Thr Asn Tyr Ala Asp Ser Val Ser
    50                  55                  60

Arg Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Ser
                85                  90                  95

Arg Gly Val Ser Gly Glu Arg Gly Gln Gly Thr Gln Val Thr Val Ser
            100                 105                 110

Ser Glu Pro Lys Thr Pro Lys Pro His Ser Gly Arg
        115                 120

<210> SEQ ID NO 22
<211> LENGTH: 132
<212> TYPE: PRT
<213> ORGANISM: Lama glama

<400> SEQUENCE: 22

Gln Val Gln Leu Gln Gln Ser Gly Gly Gly Leu Val Gln Pro Gly Gly
1               5                   10                  15

-continued

Ser Leu Arg Leu Ser Cys Ala Ala Ser Gly Ser Ile Phe Ser Ile His
            20                  25                  30

Thr Met Gly Trp Tyr Arg Gln Ala Pro Gly Lys Gln Arg Glu Leu Val
        35                  40                  45

Thr Thr Ile Thr Thr Gly Gly Thr Thr Asn Tyr Ala Asp Ser Val Lys
    50                  55                  60

Gly Arg Phe Thr Ile Ser Arg Asp Asp Ala Lys Asn Thr Val Tyr Leu
65                  70                  75                  80

Gln Met Asn Asn Leu Lys Pro Glu Asp Thr Ala Val Tyr Tyr Cys Tyr
                85                  90                  95

Ala Leu Ile Gln Thr Ala Ser Thr Thr Trp Tyr Arg Gly Tyr Trp Gly
            100                 105                 110

Gln Gly Thr Gln Val Thr Val Ser Ser Glu Pro Lys Thr Gln Asn His
        115                 120                 125

Asn Ser Gly Arg
        130

<210> SEQ ID NO 23
<211> LENGTH: 126
<212> TYPE: PRT
<213> ORGANISM: Lama glama

<400> SEQUENCE: 23

Gln Val Lys Leu Gln Glu Ser Gly Gly Gly Leu Val Gln Pro Gly Gly
1               5                   10                  15

Ser Leu Arg Leu Ser Cys Thr Ala Ser Arg Ser Ile Phe Thr Arg Ala
            20                  25                  30

Met Ala Trp Tyr Arg Gln Ala Pro Gly Lys Gln Arg Glu Leu Val Ala
        35                  40                  45

Ala Ile Asp Ser Gly Asp Arg Thr His Tyr Ala Asp Ser Val Lys Gly
    50                  55                  60

Arg Phe Thr Ile Ser Arg Asn Asn Ala Lys Asp Thr Leu Tyr Leu Gln
65                  70                  75                  80

Met Asn Ser Leu Lys Ser Glu Asp Thr Ala Val Tyr Tyr Cys Asn Ala
                85                  90                  95

Asn Leu Gly Ala Leu Leu Asp Tyr Trp Gly Gln Gly Thr Gln Val Thr
            100                 105                 110

Val Ser Ser Glu Pro Lys Thr Gln Thr Thr Ser Gly Arg
        115                 120                 125

<210> SEQ ID NO 24
<211> LENGTH: 129
<212> TYPE: PRT
<213> ORGANISM: Lama glama

<400> SEQUENCE: 24

Gln Val Lys Leu Gln Glu Ser Gly Gly Gly Leu Val Gln Ala Gly Gly
1               5                   10                  15

Ser Leu Arg Leu Ser Cys Ala Ala Ser Gly Phe Thr Phe Ala Thr Tyr
            20                  25                  30

Ala Met Ala Trp Tyr Arg Gln Ala Pro Gly Lys Gln Arg Glu Leu Val
        35                  40                  45

Ala Ser Ile Ser Asn Phe Gly Ser Thr Ala Tyr Gly Asp Ser Val Lys
    50                  55                  60

Gly Arg Phe Thr Ile Ser Arg Asp Asn Ala Lys Asn Thr Val Tyr Leu
65                  70                  75                  80

```
Glu Met Asn Ser Leu Lys Ser Glu Asp Thr Ala Val Tyr Tyr Cys Lys
            85                  90                  95

Arg Val Arg Asp Val Ile Gly Arg Pro Glu Leu Trp Gly Gln Gly Thr
        100                 105                 110

Gln Val Thr Val Ser Ser Glu Pro Lys Thr Pro Lys Pro His Ser Gly
        115                 120                 125

Arg

<210> SEQ ID NO 25
<211> LENGTH: 132
<212> TYPE: PRT
<213> ORGANISM: Lama glama

<400> SEQUENCE: 25

Gln Val Lys Leu Gln Glu Ser Gly Gly Gly Leu Val Gln Pro Gly Gly
1               5                   10                  15

Ser Leu Arg Leu Ser Cys Leu Pro Ser Ile Asn Ile Phe Ser Leu Ala
            20                  25                  30

Ala Met Gly Trp Tyr Arg Gln Ala Pro Gly Lys Gln Arg Glu Leu Val
        35                  40                  45

Ala Ser Ile Ser Ser Gly Gly Thr Ala Asn Tyr Ala Asp Ser Tyr Ala
    50                  55                  60

Asp Ser Val Lys Gly Arg Phe Thr Ile Ser Arg Asp Ile Ala Lys Asn
65                  70                  75                  80

Thr Val Asp Leu Gln Met Asn Ser Leu Lys Pro Glu Asp Thr Ala Val
                85                  90                  95

Tyr Tyr Cys Lys Val Asp Ser Tyr Thr Tyr Gly Thr Asp Ile Trp Gly
            100                 105                 110

Lys Gly Val Leu Val Thr Val Ser Ser Glu Pro Gln Asp Thr Lys Thr
        115                 120                 125

Thr Ser Gly Arg
    130

<210> SEQ ID NO 26
<211> LENGTH: 140
<212> TYPE: PRT
<213> ORGANISM: Lama glama

<400> SEQUENCE: 26

Gln Val Lys Leu Gln Gln Ser Gly Gly Gly Leu Val Gln Ala Gly Gly
1               5                   10                  15

Ser Leu Arg Leu Ser Cys Ala Ala Ser Gly Thr Phe Ser Arg Tyr Ala
            20                  25                  30

Met Gly Trp Phe Arg Gln Ala Pro Gly Lys Glu Arg Glu Phe Val Ala
        35                  40                  45

Ala Ile Asn Trp Thr Gly Gly Ser Thr Tyr Tyr Ala Asp Ser Val Lys
    50                  55                  60

Gly Arg Phe Thr Ile Ser Gly Asp Asn Ala Lys Asn Thr Val Tyr Leu
65                  70                  75                  80

Gln Met Asn Ser Leu Lys Pro Gly Asp Thr Ala Val Tyr Tyr Cys Ala
                85                  90                  95

Ala Glu Val His Pro Gly Asp Tyr Gly Leu Thr Tyr Met Gln Ser Gln
            100                 105                 110

Tyr Glu Tyr Asp Tyr Trp Gly Gln Gly Thr Gln Val Thr Val Ser Ser
        115                 120                 125

Glu Pro Lys Thr Pro Lys Pro Thr Thr Ser Gly Arg
```

```
            130              135              140

<210> SEQ ID NO 27
<211> LENGTH: 131
<212> TYPE: PRT
<213> ORGANISM: Lama glama

<400> SEQUENCE: 27

Asp Val Gln Leu Gln Ala Ser Gly Gly Gly Leu Val Gln Ala Gly Gly
1               5                   10                  15

Ser Leu Arg Leu Ser Cys Ala Ala Ser Thr Ser Arg Phe Ser Ser Tyr
            20                  25                  30

Ala Met Gly Trp Ser Arg Gln Ala Pro Gly Lys Gln Arg Glu Leu Val
        35                  40                  45

Ala Ser Ile Ser Ser Ser Gly Leu Thr Thr Asn Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Lys Ala Asp Gly Arg Arg Tyr Ser Leu Asn Glu Tyr Trp Gly Gln Gly
            100                 105                 110

Thr Gln Val Thr Val Ser Ser Glu Pro Lys Thr Pro Lys Pro Gln Pro
        115                 120                 125

Ser Gly Arg
    130

<210> SEQ ID NO 28
<211> LENGTH: 133
<212> TYPE: PRT
<213> ORGANISM: Lama glama

<400> SEQUENCE: 28

Asp Val Gln Leu Gln Ala Ser Gly Gly Gly Leu Val Gln Ala Gly Gly
1               5                   10                  15

Ser Leu Arg Leu Ser Cys Ala Ala Ser Gly Ser Thr Ile Ser Ser Tyr
            20                  25                  30

Ala Met Ala Trp Tyr Arg Gln Ala Pro Gly Lys Arg Arg Glu Leu Val
        35                  40                  45

Ala His Ile Ser Ser Gly Gly Ser Thr Asn Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Asn
                85                  90                  95

Ile Tyr Tyr Gly Gly Asp Tyr Tyr Thr Gly Val Lys Pro Asn Pro
            100                 105                 110

Trp Gly Gln Gly Thr Gln Val Thr Val Ser Ser Ala His His Ser Glu
        115                 120                 125

Asp Pro Arg Gly Arg
    130

<210> SEQ ID NO 29
<211> LENGTH: 137
<212> TYPE: PRT
<213> ORGANISM: Lama glama

<400> SEQUENCE: 29
```

```
Gln Val Lys Leu Gln Glu Ser Gly Gly Gly Trp Val Gln Ala Gly Gly
  1               5                  10                  15

Ser Leu Arg Leu Ser Cys Ala Ala Ser Ala Leu Thr Ala Ser Ile Thr
             20                  25                  30

Thr Met Gly Trp Phe Arg Gln Thr Pro Glu Lys Glu Arg Glu Phe Leu
         35                  40                  45

Ala Ala Ile Asn Trp Thr Gly Asp Tyr Lys Tyr Tyr Ala Asp Ser Val
     50                  55                  60

Lys Gly Arg Phe Thr Ile Ser Arg Asp Asn Ala Lys Asn Thr Val Asp
 65                  70                  75                  80

Leu Gln Met Asn Gln Leu Lys Pro Glu Asp Thr Ala Val Tyr Tyr Cys
                 85                  90                  95

Ala Ala Ser Lys Ile Arg Asn Asp Ile Tyr Leu Asn Asp Tyr Thr Trp
            100                 105                 110

Tyr Gln Tyr Trp Gly Gln Gly Thr Gln Val Thr Val Ser Ser Glu Pro
             115                 120                 125

Lys Thr Pro Lys Pro Gln Ser Gly Arg
    130                 135
```

<210> SEQ ID NO 30
<211> LENGTH: 143
<212> TYPE: PRT
<213> ORGANISM: Lama glama

<400> SEQUENCE: 30

```
Asp Val Gln Leu Gln Ala Ser Gly Gly Gly Leu Val Gln Ala Gly Gly
  1               5                  10                  15

Ser Leu Arg Leu Ser Cys Val Ala Ser Ala Arg Thr Phe Ser Ser Tyr
             20                  25                  30

Ala Met Gly Trp Phe Arg Gln Ala Pro Gly Lys Glu Arg Glu Phe Val
         35                  40                  45

Ala Ala Ile Ser Trp Ser Gly Ala Ser Thr Asp Tyr Ala Asp Ser Val
     50                  55                  60

Lys Gly Arg Phe Thr Ile Ser Arg Asp Asn Ala Lys Lys Thr Val Tyr
 65                  70                  75                  80

Leu Gln Met Asn Thr Leu Lys Pro Glu Asp Thr Ala Val Tyr Tyr Cys
                 85                  90                  95

Ala Ala His His Ile Thr Pro Thr Gly Ser Tyr Tyr Tyr Ser Glu Pro
            100                 105                 110

Leu Pro Val Asp Met Val Tyr Asp Tyr Trp Gly Gln Gly Thr Gln Val
             115                 120                 125

Thr Val Ser Ser Glu Pro Lys Thr Lys Thr Thr Ser Gly Arg
    130                 135                 140
```

<210> SEQ ID NO 31
<211> LENGTH: 17
<212> TYPE: PRT
<213> ORGANISM: Artificial Sequence
<220> FEATURE:
<223> OTHER INFORMATION: synthetic viral peptide

<400> SEQUENCE: 31

```
Gly Tyr Phe Arg Phe Glu Ser Trp Val Asn Pro Phe Tyr Thr Leu Ala
  1               5                  10                  15

Pro
```

```
<210> SEQ ID NO 32
<211> LENGTH: 17
<212> TYPE: PRT
<213> ORGANISM: Artificial Sequence
<220> FEATURE:
<223> OTHER INFORMATION: synthetic viral polypeptide

<400> SEQUENCE: 32

Glu Ser Trp Val Asn Pro Phe Tyr Thr Leu Ala Pro Met Gly Thr Gly
1               5                   10                  15

Asn

<210> SEQ ID NO 33
<211> LENGTH: 17
<212> TYPE: PRT
<213> ORGANISM: Artificial Sequence
<220> FEATURE:
<223> OTHER INFORMATION: synthetic viral polypeptide

<400> SEQUENCE: 33

Thr Val Pro Pro Asn Gly Tyr Phe Arg Phe Glu Ser Trp Val Asn Pro
1               5                   10                  15

Phe

<210> SEQ ID NO 34
<211> LENGTH: 17
<212> TYPE: PRT
<213> ORGANISM: Artificial Sequence
<220> FEATURE:
<223> OTHER INFORMATION: synthetic viral polypeptide

<400> SEQUENCE: 34

Pro Phe Tyr Thr Leu Ala Pro Met Gly Thr Gly Asn Gly Arg Arg Arg
1               5                   10                  15

Ile

<210> SEQ ID NO 35
<211> LENGTH: 65
<212> TYPE: DNA
<213> ORGANISM: Artificial Sequence
<220> FEATURE:
<223> OTHER INFORMATION: primer

<400> SEQUENCE: 35
gctggattgt tattactcgc ggcccagccg gccatggccc aggtgcacaa gctgcagsag    60 tcwgg                                                                65

<210> SEQ ID NO 36
<211> LENGTH: 48
<212> TYPE: DNA
<213> ORGANISM: Artificial Sequence
<220> FEATURE:
<223> OTHER INFORMATION: primer

<400> SEQUENCE: 36
gatggtgatg atgatgtgcg gccgcgctgg ggtcttcgct gtggtgcg                 48

<210> SEQ ID NO 37
<211> LENGTH: 69
<212> TYPE: DNA
<213> ORGANISM: Artificial Sequence
<220> FEATURE:
<223> OTHER INFORMATION: primer

<400> SEQUENCE: 37
```

```
cgtggattgt tattatctgc ggcccagccg gccatggccg atgtgcagct gcaggcgtct    60
ggagggagg                                                            69

<210> SEQ ID NO 38
<211> LENGTH: 48
<212> TYPE: DNA
<213> ORGANISM: Artificial Sequence
<220> FEATURE:
<223> OTHER INFORMATION: primer

<400> SEQUENCE: 38
gatggtgatg atgatgtgcg gccgctggtt gtggttttgg tgtcttgg                 48

<210> SEQ ID NO 39
<211> LENGTH: 361
<212> TYPE: DNA
<213> ORGANISM: Lama glama

<400> SEQUENCE: 39
caggtgcaac tgcagcagtc tggggaggc ttggtgcagc ctggagggtc tctgagactc     60
tcctgtgtag cctctgaaag cactgtcagt atcaatatca tgggctggta ccgccaggct   120
ccagggaagc agcgcgagct ggtcgcaact attactactg gtggtaccac aaactacgca   180
gactccgtga agggccgatt caccatctcc agagacaacg ccaagaacac cgtatatctg   240
caaatgaaca gcctggaacc tgaggacacg gccgtctatt actgtaattt aaaacgtcgg   300
gatttgcaag ctcgctttgg gggctactgg ggccagggga cccaggtcac cgtctcctca   360
g                                                                  361

<210> SEQ ID NO 40
<211> LENGTH: 361
<212> TYPE: DNA
<213> ORGANISM: Lama glama

<400> SEQUENCE: 40
caggtgcagc tgcaggagtc agggggaggc ttggtgcagc ctggagggtc tctgagactc    60
tcctgtgcag cctctgaaag cacgcccagt atcaataccg tgggctggta ccgccaggct   120
ccagggaagg agcgcgagct ggtcgcaact attactagtg gtggtatgac aaattatgca   180
gactccgtga agggccgatt caccatctcc agagacaacg caagaacac ggtgtatctg    240 caaatgaaca gcctggaacc tggggacacg gccgtctatt actgtaattt aaaacggcgc   300
gatttgcaag ctcggtttgg gggctactgg ggccagggga cccaggtcac cgtctcctca   360
g                                                                  361

<210> SEQ ID NO 41
<211> LENGTH: 361
<212> TYPE: DNA
<213> ORGANISM: Lama glama

<400> SEQUENCE: 41
caggtcaagc tgcagcagtc agggggaggc ttggtgcagc ctggagggtc tctgagactc    60
tcctgtgcag cctctgaaag cacgatcagt atcaatacct gggctggta ccgccaggct    120 ccagggaacc agcgcgagct ggtcgctact attactactg gtggtaccac aaactatgca   180
gactccgtga agggccgatt caccatctcc agggacaacg ccaagaacac ggtgtatctg   240
caaatgaaca acctggaacc tggggacacg gccgtctatt actgtaactt gaaacggcgg   300
```

```
gatttgcaat ctcgctttgg gggctactgg ggccagggga cccaggtcac cgtctcctca    360
g                                                                    361

<210> SEQ ID NO 42
<211> LENGTH: 361
<212> TYPE: DNA
<213> ORGANISM: Lama glama

<400> SEQUENCE: 42
caggtgaagc tgcagcagtc aggggggagg cttggtgcagc ctggagggtc tctgagactc    60
tcctgtgcag cctctgaaag cacgcccagt atcaatacca tgggctggta ccgccaggct    120
ccagggaagg agcgcgagct ggtcgcaact attactagtg gtggtatgac aaattatgca    180
gactccgtga agggccgatt caccatctcc agagacaacg caagaacac ggtgtatctg    240 caaatgaaca gcctggaacc tggggacacg gccgtctatt actgtaattt aaaacggcgc    300
gatttgcaag ctcggtttgg gggctactgg ggccagggga cccaggtcac cgtctcctca    360
g                                                                    361

<210> SEQ ID NO 43
<211> LENGTH: 364
<212> TYPE: DNA
<213> ORGANISM: Lama glama

<400> SEQUENCE: 43
caggtgaagc tgcagcagtc aggggggagg cttggtgcagc ctgggggtc tctgagactc    60 tcctgtgcag cctctggatt caccttcagg aactatgcca tgagctgggt ccgccaggct    120
ccaggaaagg ggctcgagtg gtctcggct attgctgctg gcggtgctgt cacaaaatat    180
gcggactccg tgaagggccg attcaccatc tccagagaca acgccaggga cacactgtat    240
ctgcaaatga acagcctgaa acctgaggac acggccgtgt attactgtgc aaagcccga    300 gatttctggt attcgcctga gtttgacttc cggggccagg ggaccaggt caccgtctcc    360 tcag                                                                 364

<210> SEQ ID NO 44
<211> LENGTH: 367
<212> TYPE: DNA
<213> ORGANISM: Lama glama

<400> SEQUENCE: 44
caggtgcagc tgcagcagtc aggggggagga ctggtgcagg ctggggactc tctgacaatt    60
tcctgtgcat cctctttatt caccttcagc acttccacta tgggctggtt ccgccaggct    120
ccagggaagg agcgtgagtt tgtagccgct attaagtcga gtggtagtag tatgtattat    180
gcagattccg tgcagggccg gttcaccatc tccagagaca acgccaagaa acggtgact    240 ctgcaaatga atagcctgaa acctgaggac acggccgttt attactgtgc aaagggagtg    300
tacggtagta ggcggtcggc ggactttggt tcctggggcc aggggaccca ggtcaccgtc    360
tcctcgg                                                              367

<210> SEQ ID NO 45
<211> LENGTH: 367
<212> TYPE: DNA
<213> ORGANISM: Lama glama

<400> SEQUENCE: 45
caggtgcagc tgcagcagtc aggggggagga ctggtgcagg ctggggactc tctgagaatt    60
```

-continued

```
tcctgtgcag cctctttatt taccttcagt acctccacta tgggctggtt ccgccaggct      120
ccagggaagg agcgtgagtt tgttgcagct attcgttcga ctggagatag tatgtactat      180
gcagactccg tgcagggccg gttcaccatc tccagagaca acgccaaaaa gatggtttat      240
ctgcaaatga caacctgaaa cctgaggac acggccgttt attattgtgc caaggggggtg     300 tacggtagta ggcggtcggc ggactttggt tcctggggcc aggggaccca ggtcaccgtc      360
tcctcgg                                                                367
```

<210> SEQ ID NO 46
<211> LENGTH: 367
<212> TYPE: DNA
<213> ORGANISM: Lama glama

<400> SEQUENCE: 46

```
gatgtgcagc tgcaggcgtc tggaggaggt ttggttcaag ctggggggctc tctgagaatt      60 tcctgtacag ccgacggata tacgttcagt acctccacta tgggctggtt ccgccaggct      120
ccagggaagg agcgtgagtt tgtagccgcg attaaatcgg atggttctat aatgtactat      180
gcagactccg tcgccggccg attcatcatc tccagagaca acgccaagaa aatggtgttt      240
ctgcaaatgg atagactgaa acctgaggac acggccgttt attactgtgc aaaggggggtg     300 tacggtagta ggcggtcggc ggacttcggt tggtggggcc aggggaccca ggtcaccgtc      360
tcctcgg                                                                367
```

<210> SEQ ID NO 47
<211> LENGTH: 370
<212> TYPE: DNA
<213> ORGANISM: Lama glama

<400> SEQUENCE: 47

```
caggtcaagc tgcaggagtc aggggggaggc ttggtgcagg ctggggagtc tctgagactc      60
tcctgtgcag cctctggaag caacttcagt atcaatggcg tgggctggta ccgccaggct      120
ccagggaaac agcgcgaatt ggtcgcaggt attactaatg gtggttacac aagttatgca      180
gactctgtga agggccgatt caccatctcc acagacaacg ccaagaacac ggtgtatctg      240
caaatgaaca gcctgagacc tgaggacaca gccgtctatt attgtaatgc aaatttccag      300
attcatcgga gtggtgctga ctacgtgagg aactactggg gccaggggac ccaggtcacc      360
gtctccgcag                                                             370
```

<210> SEQ ID NO 48
<211> LENGTH: 370
<212> TYPE: DNA
<213> ORGANISM: Lama glama

<400> SEQUENCE: 48

```
caggtcaagc tgcagcagtc aggggggaggc ttggtacagg ctgggggggtc tctgagactc      60 tcctgtgcag cctctggaaa cttcttcacg ctcaatggcg tggcctggta ccgccaggcc      120
ccagggaaac agcgcgaatt ggtcgctggt attactagtg gtggttggac aaactatgca      180
gactctgtga agggccgatt caccatctcc gcagacaacg ccaagaacac ggtgtatctg      240
caaatgaaca gcctgagacc tgaggacaca gccgtctatt actgtaatgc aaatcttcag      300
attcatcggg atagtagtgg tgacgtgagg aacgtttggg gccaggggac ccaggtcacc      360
gtctcctcag                                                             370
```

<210> SEQ ID NO 49
<211> LENGTH: 376
<212> TYPE: DNA
<213> ORGANISM: Lama glama

<400> SEQUENCE: 49

| gatgtgcagc tgcaggcgtc tgggggaggc ttggtgcagg ctgggggtc tctgagactc | 60 |
| tcctgtgcag cctctggaag cttcttcagt atcaatggcg tgggctggta ccgccaggct | 120 |
| ccagggaagc agcgcgagtt ggtcgcaggt attactaatg gtggtttcac aaactatgca | 180 |
| gactccgtga agggccgatt caccatctcc agagacaacg ccaagaacac ggtgtatctg | 240 |
| caaatgaaca gcctcaaacc tgaggacaca gccgtctatt actgtaatgc aaatctccag | 300 |
| atatctcgga gtgaggatgg cgcttacgtc gtgaggaact actggggcca ggggacccag | 360 |
| atcaccgtct cctcag | 376 |

<210> SEQ ID NO 50
<211> LENGTH: 370
<212> TYPE: DNA
<213> ORGANISM: Lama glama

<400> SEQUENCE: 50

| gatgtgcagc tgcaggcgtc tggaggaggc ttggtgcagg ctgggggtc tctgagactc | 60 |
| tcctgtgcag cctctggaag cggattcagt atcaatggcg tgggctggta ccgccagact | 120 |
| ccagggagac agcgcgagtt ggtcgcaggt attactattg gtggttacac aaattatgca | 180 |
| gactccgtga agggccgatt caccatctcc agcgacaacg ccaagaacac ggtgtatctg | 240 |
| caaatgaaca gcctgaaacc tgaggacaca gccgtctatt actgtaatgc caatctccag | 300 |
| ttctatcggg gtggtggttc tgacgtgaaa aactactggg gccaggggac ccaggtcacc | 360 |
| gtctcctcag | 370 |

<210> SEQ ID NO 51
<211> LENGTH: 373
<212> TYPE: DNA
<213> ORGANISM: Lama glama

<400> SEQUENCE: 51

| caggtgcagc tgcaggagtc tgggggagga ttggtgcagg ctgggggctc tctgagactc | 60 |
| tcctgtgcag cctctggact caccttcagt agctatgcca tgggctggtt ccaccaggct | 120 |
| ccagggaagg agcgtgagtt tgtagcagct attaactgga gtggtagaga cacatactat | 180 |
| gcagactccg tgaagggccg attcaccatc tccagagaca accgcaagaa cacggtgtat | 240 |
| ctgcaaatga acagcctgaa acctgaggac acggccgttt attactgtgc agcagctgaa | 300 |
| tttttcagca gcggcgaccc cttaccgggc atggactact ggggcaaagg gaccctggtc | 360 |
| accgtctcct cag | 373 |

<210> SEQ ID NO 52
<211> LENGTH: 373
<212> TYPE: DNA
<213> ORGANISM: Lama glama

<400> SEQUENCE: 52

| caggtgaagc tgcagcagtc tggggagga ttggtgcagg ctgggggctc tctgagactc | 60 |
| tcctgtgcag cctctggact caccttcagt agctatgcca tgggctggtt ccgccaggct | 120 |
| ccagggaagg agcgtgagtt tgtagcagct attaactgga gtggtcgtga cacatactat | 180 |

| | |
|---|---:|
| gcagactccg tgaagggccg attcaccatc tccagagaca acgccaagaa cacggtgtac | 240 |
| ttgcaaacga acagcctgaa acctgaggac acggccgttt attactgtgc agccgcggaa | 300 |
| tttttacccca cccagaggtc ccctcgggaa tatgactact ggggcctggg gacccaggtc | 360 |
| accgtctcct cag | 373 |

<210> SEQ ID NO 53
<211> LENGTH: 376
<212> TYPE: DNA
<213> ORGANISM: Lama glama

<400> SEQUENCE: 53

| | |
|---|---:|
| caggtcaagc tgcagcagtc tgggggagga ctggtgcagg ctgggggctc tctgagactc | 60 |
| tcctgtgcag cctctgggta cgcctttaat acctatacca tggcttggtt ccgccaggct | 120 |
| ccagggaagg agcgtgagtt tgtagcgctt gttggtatga aggttgatgg taaaatctat | 180 |
| gcagactccg taaagggccg attcaccatc tcgagagaca acgagcagaa aacggtgctt | 240 |
| ctggagatga accacctgga gcctgaggac acggccattt attactgtgc agcctcacgt | 300 |
| agattctgga ctgcggcttt aaatgggggcg gactatccct actggggcca ggggacgcag | 360 |
| gtcaccgtct cctcag | 376 |

<210> SEQ ID NO 54
<211> LENGTH: 355
<212> TYPE: DNA
<213> ORGANISM: Lama glama

<400> SEQUENCE: 54

| | |
|---|---:|
| caggtcaaac tgcagcagtc aggggggaggc ttggtgcagg ctgggggtc tctgagactc | 60 |
| tcctgtgcag cctctggaat cgtcttcagc ttcaatgcca tgggctggta ccgcgttcct | 120 |
| ccagggaagc agcgcgagtt ggtcgcagat attcttaaga gtggtggaac aaacgttgtc | 180 |
| gactccgtga agggccgatt cgccatctcc cgagacagcg cccagaacac gctgtatctg | 240 |
| caaatgaacc ggttgaaacc tgaggacaca gccgtctatt actgtaatgc ccgtgactgg | 300 |
| agtgatggtt tcgatgagta ctggggccag gggacccagg tcaccgtctc ctcag | 355 |

<210> SEQ ID NO 55
<211> LENGTH: 373
<212> TYPE: DNA
<213> ORGANISM: Lama glama

<400> SEQUENCE: 55

| | |
|---|---:|
| caggtccaac tgcagcagtc aggggggagga ttggtgcagg ctgggggctc tctgagactc | 60 |
| tcctgttcag cctctggacg caccttcagt aactatgtca tggctggttt ccgccaggct | 120 |
| ccagggaagg agcgtgaatt tgtagcgacg attagcgcga gtggaggtag cacatactgt | 180 |
| gcagactccg tggagggccg attcaccatc tccagggaca acgccaagaa cacggcatat | 240 |
| ctacaaatga acaatttgga acctgaggac acggccgttt attactgtgc gtcagggcca | 300 |
| cgggctaatg cgtcaattag aagatctggt tataactact ggggccaggg gacccaggtc | 360 |
| accgtctcct cag | 373 |

<210> SEQ ID NO 56
<211> LENGTH: 376
<212> TYPE: DNA
<213> ORGANISM: Lama glama

<400> SEQUENCE: 56

```
caggtgcagc tgcagcagtc tgggggagga ttggtgcagg ctgggggctc tctgagactc      60
tcctgtgcag cctctggact agccttcagt agctatgcca tcacctggct ccgccaggct     120
ccagggacgg agcgtgagtt tgtagcactt attagcggga gtggtagtag cacatactat     180
gcagactccg tgaagggccg attcaccatc tccagaaata cgccaagaa cacggtgtat      240
ctgcaaatga cagcctaaa acctgaggac acggccgttt attactgtac agcctcggag      300
ttcctacttc acccgccacc cccgaaccaa agtatgact actggggcca ggggacccag      360
gtcaccgtct cctcag                                                     376
```

<210> SEQ ID NO 57
<211> LENGTH: 373
<212> TYPE: DNA
<213> ORGANISM: Lama glama

<400> SEQUENCE: 57

```
caggtccagc tgcagcagtc aggggagga ttggtgcgcg ctgggggctc tctgagactc       60
tcctgttcag cctctggacg cacctttggt aacgaagtta tgggctggtt ccgccaggct     120
ccggggaagg agcgtgagtt cgtagcagct attaactgga gtagtggtaa cacatactat     180
agagactccg tgaagggccg attcaccatc tccagagaca cgccaagaa cacggtgtat      240
ctacaaatga cagtcttga acctgaggac acggccgttt attactgtgc tgcgagatca      300
cggccggcta tctcaaccag aagacctgac tatttcgcct ggggccaggg gacccaggtc    360
accgtctcct cag                                                        373
```

<210> SEQ ID NO 58
<211> LENGTH: 367
<212> TYPE: DNA
<213> ORGANISM: Lama glama

<400> SEQUENCE: 58

```
caggtccaac tgcagcagtc aggggagga ttggtgcagg ctgggggctc tctgagactc       60
tcctgtacgg cctctggacg cattgacagg acctataccg tgtcctggtt ccgccagggt     120
ccagggaagg agcgtgagtt tgtagcaact attagctggg atggtagtat atactatgac     180
aacgccgttg agggccgatt cagcatctca ggagacaacg ccaagaccac ggtggctctg     240
caaatgaaca gcctgaaacc tgaggacacg gccgtttatt actgtgcagc acgccgccga    300
gtgttttcac gtgccgcggc agcgtataac tattggggcc aggggaccca ggtcaccgtc    360
tcctcgg                                                               367
```

<210> SEQ ID NO 59
<211> LENGTH: 340
<212> TYPE: DNA
<213> ORGANISM: Lama glama

<400> SEQUENCE: 59

```
caggtcaagc tgcagcagtc aggggagagc ttggtgcagc ctgggggtc tctgagactc      60
acctgtgcag cctctggatt cccttcagt acctatgcca tacgctgggt ccggcgacct    120
ccaggaaagg ggctcgagtg ggtctcgacg attcatcctg attttaccac aaactatgca    180
gactccgtga gccgccgatt caccatctcc agagacaacg ccaagaacac ggtatatctg    240
caaatgaaca gcctgaaacc tgaagacacg gccgtgtatt attgttcaag aggggtgtcc    300
ggagaaaggg gccagggac ccaggtcacc gtctcctcgg                            340
```

<210> SEQ ID NO 60
<211> LENGTH: 364
<212> TYPE: DNA
<213> ORGANISM: Lama glama

<400> SEQUENCE: 60

```
caggtccagc tgcagcagtc tggggggaggc ttggtgcagc ctggggggtc tctgagactc    60
tcctgtgcag cctctggaag catcttcagt atccatacca tgggctggta ccgccaggct   120
ccagggaagc agcgcgagtt ggtcacaact attactactg gtggtaccac aaactatgca   180
gactccgtga agggccgatt caccatctcc agagacgacg ccaagaatac ggtttatctg   240
caaatgaaca acctgaaacc tgaggacacg ccgtctatt actgttatgc cctcatacag   300
actgccagta ctacttggta ccgccagtac tggggccagg ggacccaggt caccgtctcc   360
tcag                                                                364
```

<210> SEQ ID NO 61
<211> LENGTH: 346
<212> TYPE: DNA
<213> ORGANISM: Lama glama

<400> SEQUENCE: 61

```
caggtcaaac tgcaggagtc tggggggaggc ttggtgcagc ctggggggtc tctgagactc    60
tcctgtacag cctctagaag catcttcact cgcgccatgg cctggtaccg ccaggctcca   120
gggaagcagc gcgagttggt cgcggctatt gatagtggtg atagaactca ctatgcagac   180
tccgtgaagg gccgattcac catctccaga aacaacgcca aggacacgtt gtatctgcaa   240
atgaacagcc tgaaatctga ggacacggcc gtctattact gtaatgccaa cctaggtgcc   300
ctccttgact actggggcca ggggacccag gtcaccgtct cctcag                  346
```

<210> SEQ ID NO 62
<211> LENGTH: 355
<212> TYPE: DNA
<213> ORGANISM: Lama glama

<400> SEQUENCE: 62

```
caggtgaagc tgcaggagtc agggggaggc ttggtgcagg ctggggggtc tctgagactc    60
tcctgtgcag cctctggatt caccttcgct acctatgcca tggcctggta ccgtcaggct   120
ccagggaagc agcgtgagtt ggtcgcaagt atcagtaatt ttggtagtac agcttatgga   180
gactccgtga agggccgatt caccatctcc agagacaacg ccaagaacac ggtgtatctg   240
gaaatgaaca gcctcaaatc tgaggacacg ccgtctatt actgtaaacg cgtccgcgat   300
gtgattggtc gccctgagtt atggggccag gggacccagg tcaccgtctc ctcag       355
```

<210> SEQ ID NO 63
<211> LENGTH: 364
<212> TYPE: DNA
<213> ORGANISM: Lama glama

<400> SEQUENCE: 63

```
caggtcaagc tgcagcagtc tggggggaggt ttggtgcagc ctggggggtc tctgagactc    60
tcctgtctac cctctataaa catcttcagc ctcgctgcca tgggctggta ccgccaggct   120
ccagggaagc agcgcgagtt ggtcgcaagc attagtagtg gtggtaccgc aaactatgca   180
gactcctatg cagactccgt gaagggccga ttcaccatct ccagagacat cgccaagaac   240
```

```
acggtggatc tacaaatgaa cagcctgaaa ccggaggaca cggccgtcta ttactgtaag    300
gtagattcct atacatacgg cacggacatc tggggcaaag gggtcctggt caccgtctcc    360
tcag                                                                 364

<210> SEQ ID NO 64
<211> LENGTH: 385
<212> TYPE: DNA
<213> ORGANISM: Lama glama

<400> SEQUENCE: 64
caggtcaaac tgcagcagtc aggggggagga ttggtgcagg ctgggggctc tctgagactc     60
tcctgtgcag cctctggaac cttcagtagg tatgccatgg gctggttccg ccaggctcca    120
gggaaggagc gtgagtttgt agcagcgatt aactggactg gtggtagcac atactatgca    180
gactccgtga agggccgatt caccatctcc ggagacaacg ccaagaacac ggtgtatctg    240
caaatgaaca gcctgaaacc tggggacacg gccgtttatt actgtgcagc agaggtccat    300
cccggggact acgggttgac gtatatgcaa agtcagtatg agtatgacta ctggggccag    360
gggacccagg tcaccgtctc ctcag                                          385

<210> SEQ ID NO 65
<211> LENGTH: 358
<212> TYPE: DNA
<213> ORGANISM: Lama glama

<400> SEQUENCE: 65
gatgtgcagc tgcaggcgtc tgggggaggc ttggtgcagg ctggggggtc tctgagactc     60
tcctgtgcag cctctacaag tcgtttcagt agctatgcca tgggctggtc ccgccaggct    120
ccagggaagg agcgtgagtt ggtcgcaagt attagtagta gtggtttgac cactaactac    180
gcagactccg tgaagggccg attcaccatc tccagagaca tgccaagaa caccgtgtat    240 ctgcaaatga acagcctgaa acctgaggat acggccgtct attactgtaa ggcagacggt    300
cgaaggtaca gtctaaatga atactggggc caggggaccc aggtcaccgt ctcctcag    358

<210> SEQ ID NO 66
<211> LENGTH: 370
<212> TYPE: DNA
<213> ORGANISM: Lama glama

<400> SEQUENCE: 66
gatgtgcagc tgcaggcgtc tgggggaggc ttggtgcagg ctggggggtc tctgagactc     60
tcatgtgcag cctctggaag caccatcagt agctatgcca tggcgtggta tcgccaggct    120
ccagggaagc ggcgtgagtt ggtcgcacat attagtagtg gtggtagcac aaactatgca    180
gactccgtga agggccgatt caccatctcc agagacaacg ccaagaacac ggtgtatctg    240
caaatgaaca gcctgaaacc tgaggacacg gccgtctatt actgtaatat atattatggt    300
ggtgattact actacaccgg tgtaaagccc aatccatggg gccaggggac ccaggtcacc    360
gtctcctcag                                                          370

<210> SEQ ID NO 67
<211> LENGTH: 379
<212> TYPE: DNA
<213> ORGANISM: Lama glama

<400> SEQUENCE: 67
caggtcaaac tgcaggagtc aggggggagga tgggtgcagg ctgggggctc tctgagactc     60
```

```
tcctgtgcag cctctgcact taccgccagt ataacgacca tgggctggtt ccgccagact      120
ccagagaagg agcgtgagtt cctagcagct attaactgga ctggtgatta caaatattat      180
gcagactccg tgaagggccg attcaccatc tccagagaca acgccaagaa tacggtagat      240
ctgcaaatga atcaactgaa acctgaggac acggccgttt attactgtgc agcttccaaa      300
attagaaacg atatctacct taacgactat acttggtatc agtattgggg ccaggggacc      360
caggtcaccg tctcctcag                                                   379

<210> SEQ ID NO 68
<211> LENGTH: 397
<212> TYPE: DNA
<213> ORGANISM: Lama glama

<400> SEQUENCE: 68
gatgtgcagc tgcaggcgtc tggaggagga ttggtgcagg ctgggggctc tctgagactc       60
tcctgtgtag cctctgcacg caccttcagt agttatgcaa tgggctggtt ccgccaggct      120
ccagggaagg agcgtgagtt tgtagcggct attagctgga gtggtgctag tactgactat      180
gcagactcgg tgaagggccg attcaccatc tccagagaca acgccaagaa gacggtgtat      240
ctgcaaatga acactttgaa acctgaggac acggccgttt attactgtgc agcacatcat      300
attaccccta ctggtagtta ctactacagc gaacctctac cagtcgatat ggtgtatgac      360
tactggggcc aggggaccca ggtcaccgtc tcctcag                               397
```